United States Patent
Bachlava et al.

(10) Patent No.: US 11,019,777 B2
(45) Date of Patent: *Jun. 1, 2021

(54) MULTIPLE-VIRUS-RESISTANT MELON

(71) Applicant: Seminis Vegetable Seeds, Inc., St. Louis, MO (US)

(72) Inventors: Eleni Bachlava, Vallejo, CA (US); Francois P. M. Bertrand, Aubord (FR); Jeroen S. de Vries, St. Louis, MO (US); Tarek Joobeur, Sacramento, CA (US); Joseph J. King, Davis, CA (US); Petrus J. Kraakman, Aguadulce (ES)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/814,233

(22) Filed: Nov. 15, 2017

(65) Prior Publication Data

US 2020/0060112 A1    Feb. 27, 2020

Related U.S. Application Data

(62) Division of application No. 13/972,702, filed on Aug. 21, 2013, now Pat. No. 9,913,439.

(60) Provisional application No. 61/692,643, filed on Aug. 23, 2012.

(51) Int. Cl.
| | |
|---|---|
| *A01H 5/08* | (2018.01) |
| *C12Q 1/6895* | (2018.01) |
| *G01N 33/50* | (2006.01) |
| *C12N 15/82* | (2006.01) |
| *A01G 22/00* | (2018.01) |
| *A01H 1/04* | (2006.01) |

(52) U.S. Cl.
CPC ............... *A01H 5/08* (2013.01); *A01G 22/00* (2018.02); *A01H 1/04* (2013.01); *C12N 15/8241* (2013.01); *C12Q 1/6895* (2013.01); *G01N 33/5091* (2013.01); *C12Q 2600/13* (2013.01)

(58) Field of Classification Search
None
See application file for complete search history.

(56) References Cited

U.S. PATENT DOCUMENTS

| | | | |
|---|---|---|---|
| 8,026,414 B2 | 9/2011 | Kim et al. | |
| 9,913,439 B2 * | 3/2018 | Bachlava | A01G 22/00 |
| 2011/0138493 A1 | 6/2011 | Copes et al. | |

FOREIGN PATENT DOCUMENTS

| | | |
|---|---|---|
| EP | 1800535 A1 | 6/2007 |
| EP | 1816202 A2 | 8/2007 |
| EP | 1962578 B1 | 5/2011 |
| WO | WO 1990/02185 A1 | 3/1990 |
| WO | WO 2003/066900 A1 | 8/2003 |
| WO | WO 2005/040426 A1 | 5/2005 |
| WO | WO 2005/068637 A1 | 7/2005 |
| WO | WO 2007/030356 A2 | 3/2007 |
| WO | WO 2010/025747 A1 | 3/2010 |
| WO | WO 2011/101855 A2 | 8/2011 |

OTHER PUBLICATIONS

Anagnostou et al 2000 Euphytica 116:265-270 (Year: 2000).*
Anagnostou et al., "Inheritance and linkage analysis of resistance to zucchini yellow mosaic virus, watermelon mosaic virus, papaya ringspot virus and powdery mildew in melon," *Euphytica* 116:265-270. 2000.
Brotman et al., "Molecular markers linked to papaya ring spot virus resistance and *Fusarium* race-2 resistance in melon," *Theor. Appl. Genet.* 110:337-345, 2005.
Danin-Poleg et al., "Oligogenic inheritance of resistance to zucchini yellow mosaic virus in melons," *Euphytica* 93:331-337, 1997.
Danin-Poleg et al., "Search for molecular markers associated with resistance to viruses in melon," *Acta Horticulturae* (ISHS) 510:399-404, 2000.
Danin-Poleg et al., "Construction of a genetic map of melon with molecular markers and horticultural traits, and localization of genes associated with ZYMV resistance," *Euphytica* 125:373-384, 2002.
Diaz et al., "Potential sources of resistance for melon to nonpersistently aphid-borne viruses," *Plant Disease* 87:960-964, 2003.
Diaz et al., "A consensus linkage map for molecular markers and Quantitative Trait Loci associated with economically important traits in melon (*Cucumis melo* L.)," *BMC Plant Biol.* 11:111. 2011.
Diaz-Pendon et al., "Inheritance of resistance to watermelon mosaic virus in Cucumis melo that impairs virus accumulation, symptom expression, and aphid transmission," *Phytopathology* 95:840-846, 2005.
Dogimont et al., "Identification of QTLs contributing to resistance to different strains of cucumber mosaic cucumovirus in melon," *Acta Horticulturae* (ISHS) 510:391-398, 2000.
Escribano-Martin, *Caracterizacion Etnobotanica, Agromorfologica, Sensorial, Fisico-Quimica, Nutricional y Molecular de las Variedades Locales de MelOn de Villaconejos* (Doctoral dissertation). <Retrieved from http://oa.upm.es/4748/> 2010.
Essafi et al., "Dissection ofi the oligogenic resistance to cucumber mosaic virus in the melon accession PI 161375," *Theor. Appl. Genet.* 118(2):275-284, 2009.
Gilbert et al., "Inheritance of resistance to watermelon mosaic virus in Cucumis melo L," *Hort Sci.* 29(2):107-110, 1994.

(Continued)

*Primary Examiner* — Brent T Page
(74) *Attorney, Agent, or Firm* — Dentons US LLP; Matthew Madsen

(57) ABSTRACT

The invention relates to a melon plant, and parts thereof including seeds and fruit, that is resistant to Zucchini Yellow Mosaic Virus (ZYMV) and Watermelon Mosaic Virus (WMV). The melon plant may further comprise resistance to Cucumber Mosaic Virus (CMV) and/or further display a Brix measurement of ≥9.5° Bx, orange flesh color, and/or a fruit width to length ratio of ≥0.5. Methods for producing such a plant are also provided.

18 Claims, 18 Drawing Sheets

Specification includes a Sequence Listing.

(56) References Cited

OTHER PUBLICATIONS

Henning et al., "'Hannah's Choice F1': A new muskmelon hybrid with resistance to powdery mildew, Fusarium race-2, and potyviruses," *Hort Sci.* 40(2):492-493, 2005.

Herrington et al., "Further sources of resistance to ZYMV in Cucumis melo L.," *Cucurbit Genetics Cooperative Report* 7:43-44 (article 19), 1984.

Lecoq et al., "Interaction of zucchini yellow mosaic virus strains and muskmelon lines," *Cucurbit Genetics Cooperative Report* 13:25-26 (article 9), 1990.

Lopez-Sese et al., "Resistance to cucurbit yellow stunting disorder virus (CYSDV) in Cucumis melo L," *Hort Sci.* 35:110-113, 2000.

Morales et al., "A physical map covering the nsv locus that confers resistance to Melon necrotic spot virus in melon (*Cucumis melo* L.)," *Theor. Appl. Genet.* 111:914-922, 2005.

Palomares-Rius et al., "Simple sequence repeat markers linked to QTL for resistance to Watermelon mosaic virus in melon," *Theor. Appl. Genet.* 123(7):1207-1214, 2011.

Park et al., "Comparative mapping of ZYMV resistances in cucumber (*Cucumis sativus* L.) and melon (*Cucumis melo* L.)," *Theor. Appl. Genet.* 109:707-712, 2004.

Perin et al., "A reference map of Cucumis melo based on two recombinant inbred line populations," *Theor. Appl. Genet.* 104:1017-1034, 2002.

Pitrat et al., "Inheritance of resistance to cucumber mosaic virus transmission by Aphis gossypii in Cucumis melo," *Phytopathology* 70:958-961, 1980.

Pitrat et al., "Two alleles for watermelon mosaic virus 1 resistance in melon," *Curcurbit Genetics Cooperative* Report No. 6, 1983.

Pitrat et al., "Inheritance of zucchini yellow mosaic virus resistance in Cucumis melo L.," *Euphytica* 33:57-61, 1984.

Rabelo Filho et al., "Source of resistance in melon and watermelon to viruses from genus Potyvirus," *Revista Brasileira de Ciencias Agrarias* 5(2): 187-191, 2010. (English Abstract).

Soria et al., "New source of resistance to mosaic virus transmission by Aphis gossypii in melon," *Euphytica* 133(3):313-318, 2003.

Van Leeuwen et al., "Analysis of the melon genome in regions encompassing TIR-NBS-LRR resistance genes," *Molecular Genetics and Genomics* 273(3):240-251, 2005.

Product information for "White Skin" donor pickling melon from Known-You Seed Co., Ltd., "http://www.knownyou.com/en index.jsp?bodyinclude=PRODUCTDETAIL&pid=9C8B16EC5695090B8AB8E3428C1AEBDBP197."

Escribano-Martin, *CaracterizaciOn Etnobotanica, Agro-morfolOgica, Sensorial, Ffsico-Quirnica, Nutricional y Molecular de las Variedades Locales de Mel& de Villaconejos* (Doctoral dissertation). <Retrieved from http://oa.upm.es/47488> 2010. (English abstract at pp. 389-392).

Ohashi et al., "Evaluation of Different Muskmelon (*Cucumis melo*) Cultivars and Production Systems in Oman," *International Journal of Agriculture and Biology* 11(5):596-600. 2009.

Ekbic et al., "Screening of Turkish Melon Accessions for Resistance to ZYMV, WMC and CMV," *Not Sci Biol* 2(1):55-57, 2010.

McCreight et al., "Pedigree of PI 414723 Melon," Cucurbit Genetics Cooperative Report, *NC State University* 15:51-52, 1992.

Supplementary European Search Report regarding European Application No. 13830581, dated May 18, 2016.

Horvath, "Reactions of sixty-seven accessions of twelve *Cucumis* species to seven viruses," *Acta Phytopathologica et Entomologica Hungarica* 28(2-4):403-414, 1993.

\* cited by examiner

FIG. 4

| Line | Disease Severity Score (1-10 scale) | | | | | | | | | ELISA O.D. in young leaves | | |
|---|---|---|---|---|---|---|---|---|---|---|---|---|
| | ZYMV-path 0 | ZYMV-path 1 | ZYMV-path2 | WMV-FR | WMV-C05-270 | WMV-natural (field test) | ZYMV(0)+WMV-FR | CMV-common | CMV-Song | ZYMV-path 1 | WMV-C05-270 | WMV-LL2B3 |
| ME8094 | 1.0 | 1.0 | 1.0 | 1.0 | 1.0 | 1.0 | 1.0 | 1.0 | 1.5 | 0.025 | 0.008 | 0.064 |
| Vedrantais | 9.0 | 9.0 | 9.0 | 8.8 | 9.0 | 7.2 | 9.0 | 9.0 | 9.0 | 1.097 | 0.242 | 1.454 |
| Topmark | | 9.0 | 9.0 | 6.4 | | | | 9.0 | 9.0 | 0.959 | 0.256 | |
| PMR45 | 9.0 | | | 6.5 | 9.0 | 5.0 | 9.0 | | | | | |
| PMR5 | | | | 9.0 | | | | | | | | |
| PI414723 | 1.0 | 4.4 (necr) | 9.0 | | | 4.5 | 9.0 | | | 1.532 | | |
| PI161375 | | | | | | | | n/a | 9.0 | | | |
| Freeman's cucumber | | | | | | | | 1.0 | 3.5 | | | |
| Virgos | | | | | | 7.0 | | 1.0 | 4.6 | | | |
| MR1 | | | | | | | | 9.0 | 9.0 | | | |
| TGR1551 | 9.0 | | | 3.0 | 9.0 | 1.6 | 9.0 | | | | 0.504 | 1.249 |
| Pastis-1 | | | | 5.4 | 9.0 | 3.0 | | 9.0 | 9.0 | | 0.324 | |
| Pastis-2 | | | | 2.8 | 6.3 | 2.9 | | 9.0 | 9.0 | | 0.498 | |
| Pastis-3 | | | | 2.0 | 9.0 | 2.6 | | | | | 0.425 | 1.589 |
| Healthy control | | | | | | | | | | 0.036 | 0.008 | 0.012 |

FIG. 5A

Field test : resistance at adult plant stage to 3 CMV strains, 2 reps of 4 plts per strain

| Entry# | Variety | MDI-8 | MDI-15 | MDI-30 | AUDPC | Plot | MDI-8 | MDI-15 | MDI-30 | AUDPC-1 | Plot | MDI-8 | MDI-15 | MDI-30 | AUDPC-2 |
|---|---|---|---|---|---|---|---|---|---|---|---|---|---|---|---|
| | | | | | | | CMV-1441 | | | | | Common pathotype | | | |
| 13 | HP341 (MVS line) | 8.1 | 9.0 | 9.0 | 201 | 413 | 8.5 | 9.0 | 9.0 | 204 | 428 | 7.7 | 9.0 | 9.0 | 198 |
| 1 | Vedrantais | 5.5 | 9.0 | 9.0 | 182 | 401 | 2.0 | 9.0 | 9.0 | 156 | 416 | 9.0 | 9.0 | 9.0 | 208 |
| 6 | Topmark | 4.0 | 8.0 | 9.0 | 160 | 406 | 5.0 | 9.0 | 9.0 | 178 | 421 | 3.0 | 7.0 | 9.0 | 141 |
| 15 | Pastis-1 | 1.0 | 9.0 | 9.0 | 148 | 415 | 1.0 | 9.0 | 9.0 | 148 | 430 | 1.0 | 9.0 | 9.0 | 148 |
| 9 | MR1 | 1.3 | 5.8 | 9.0 | 114 | 409 | 1.5 | 5.0 | 9.0 | 108 | 424 | 1.0 | 6.5 | 9.0 | 121 |
| 8 | Pastis-2 | 1.0 | 2.5 | 9.0 | 77 | 408 | 1.0 | 1.0 | 9.0 | 60 | 423 | 1.0 | 4.0 | 9.0 | 93 |
| 11 | Ginsen Makuwa | 1.0 | 1.5 | 2.8 | 19 | 411 | 1.0 | 1.0 | 2.5 | 11 | 426 | 1.0 | 2.0 | 3.0 | 26 |
| 2 | Paco | 1.0 | 1.0 | 1.3 | 2 | 402 | 1.0 | 1.0 | 1.0 | 0 | 417 | 1.0 | 1.0 | 1.5 | 4 |
| 12 | Nanbukin | 1.3 | 1.0 | 1.3 | 4 | 412 | 1.5 | 1.0 | 1.5 | 8 | 427 | 1.0 | 1.0 | 1.0 | 0 |
| 7 | PI255478 | 1.3 | 2.0 | 1.5 | 17 | 407 | 1.0 | 2.0 | 1.0 | 11 | 422 | 1.5 | 2.0 | 2.0 | 22 |
| 3 | Virgos | 1.0 | 1.0 | 1.0 | 0 | 403 | 1.0 | 1.0 | 1.0 | 0 | 418 | 1.0 | 1.0 | 1.0 | 0 |
| 4 | PI161375 | 1.0 | 1.5 | 1.5 | 9 | 404 | 1.0 | 1.0 | 1.0 | 0 | 419 | 1.0 | 2.0 | 2.0 | 19 |
| 10 | SVI 0091 (MVS line) | 1.0 | 1.0 | 1.0 | 0 | 410 | 1.0 | 1.0 | 1.0 | 0 | 425 | 1.0 | 1.0 | 1.0 | 0 |
| 5 | Freeman's cucumber | 2.0 | 1.0 | 1.0 | 8 | 405 | 2.0 | 1.0 | 1.0 | 8 | 420 | 2.0 | 1.0 | 1.0 | 8 |
| 14 | Mbnr992 | 1.0 | 1.0 | 1.0 | 0 | 414 | 1.0 | 1.0 | 1.0 | 0 | 429 | 1.0 | 1.0 | 1.0 | 0 | inoculation at 3 leaf stage

FIG. 5B

CMV-Song14
Song pathotype

| MDI-8 | MDI-15 | MDI-30 | AUDPC | Plot | MDI-8 | MDI-15 | MDI-30 | AUDPC-1 | Plot | MDI-8 | MDI-15 | MDI-30 |
|---|---|---|---|---|---|---|---|---|---|---|---|---|
| 9.0 | 9.0 | 9.0 | 208 | 613 | 9.0 | 9.0 | 9.0 | 208 | 628 | 9.0 | 9.0 | 9.0 |
| 7.5 | 9.0 | 9.0 | 197 | 601 | 6.0 | 9.0 | 9.0 | 186 | 616 | 9.0 | 9.0 | 9.0 |
| 4.3 | 9.0 | 9.0 | 172 | 606 | 4.0 | 9.0 | 9.0 | 171 | 621 | 4.5 | 9.0 | 9.0 |
| 5.5 | 9.0 | 9.0 | 182 | 615 | 5.0 | 9.0 | 9.0 | 178 | 630 | 6.0 | 9.0 | 9.0 |
| 3.3 | 9.0 | 9.0 | 165 | 609 | 1.0 | 9.0 | 9.0 | 148 | 624 | 5.5 | 9.0 | 9.0 |
| 1.0 | 6.0 | 6.5 | 115 | 608 | 1.0 | 5.0 | 6.0 | 104 | 623 | 1.0 | 7.0 | 9.0 |
| 3.5 | 6.5 | 9.0 | 121 | 611 | 4.0 | 5.5 | 9.0 | 110 | 626 | 3.0 | 7.5 | 7.0 |
| 1.0 | 5.3 | 6.3 | 107 | 602 | 1.0 | 7.0 | 6.5 | 126 | 617 | 1.0 | 3.5 | 9.0 |
| 3.0 | 7.5 | 7.5 | 126 | 612 | 2.5 | 7.5 | 6.5 | 124 | 627 | 3.5 | 7.5 | 6.0 |
| 2.0 | 5.3 | 6.3 | 94 | 607 | 1.0 | 4.0 | 7.0 | 74 | 622 | 3.0 | 6.5 | 6.0 |
| 1.0 | 2.0 | 7.5 | 60 | 603 | 1.0 | 1.0 | 6.0 | 45 | 618 | 1.0 | 3.0 | 8.0 |
| 1.0 | 4.3 | 6.3 | 75 | 604 | 1.0 | 4.0 | 5.0 | 71 | 619 | 1.0 | 4.5 | 6.5 |
| 1.0 | 1.5 | 5.5 | 39 | 610 | 1.0 | 1.0 | 1.0 | 30 | 625 | 1.0 | 2.0 | 6.0 |
| 1.0 | 1.0 | 1.0 | 2 | 605 | 1.5 | 1.0 | 1.0 | 4 | 620 | 1.0 | 1.0 | 1.0 |
| 1.3 | 1.3 | 1.3 | 5 | 614 | 1.0 | 1.5 | 1.0 | 6 | 629 | 1.0 | 1.0 | 1.5 |

FIG. 5C

| | | | | | CMV-V33N Song pathotype | | | |
|---|---|---|---|---|---|---|---|---|
| MDI-8 | MDI-15 | MDI-30 | AUDPC | Plot | MDI-8 | MDI-15 | MDI-30 | AUDPC-1 |
| 8.8 | 9.0 | 9.0 | 206 | 513 | 8.5 | 9.0 | 9.0 | 204 |
| 8.3 | 9.0 | 9.0 | 202 | 501 | 7.5 | 9.0 | 9.0 | 197 |
| 6.5 | 9.0 | 9.0 | 189 | 506 | 4.5 | 9.0 | 9.0 | 174 |
| 6.5 | 9.0 | 9.0 | 189 | 515 | 4.0 | 9.0 | 9.0 | 171 |
| 2.3 | 7.5 | 9.0 | 141 | 509 | 1.0 | 6.0 | 9.0 | 115 |
| 1.5 | 8.5 | 9.0 | 146 | 508 | 1.0 | 8.0 | 9.0 | 137 |
| 2.5 | 5.5 | 7.5 | 110 | 511 | 1.0 | 3.0 | 8.0 | 75 |
| 1.0 | 8.3 | 9.0 | 140 | 502 | 1.0 | 7.5 | 9.0 | 132 |
| 3.3 | 5.8 | 5.3 | 101 | 512 | 1.0 | 3.0 | 3.5 | 41 |
| 4.3 | 6.5 | 4.3 | 109 | 507 | 2.0 | 4.0 | 2.5 | 52 |
| 1.0 | 6.8 | 8.0 | 116 | 503 | 1.0 | 4.5 | 7.0 | 84 |
| 1.5 | 4.0 | 5.3 | 69 | 504 | 1.0 | 3.0 | 3.5 | 41 |
| 1.0 | 2.0 | 5.0 | 41 | 510 | 1.0 | 1.0 | 2.0 | 8 |
| 2.0 | 1.0 | 2.0 | 15 | 505 | 1.5 | 1.0 | 3.0 | 19 |
| 1.0 | 1.0 | 1.3 | 2 | 514 | 1.0 | 1.0 | 1.0 | 0 |

| chr | 11 | 11 | 11 | 11 | 11 | 11 | 11 | 11 |
|---|---|---|---|---|---|---|---|---|
| cM | 41.9 | 43.4 | 44.6 | 45.8 | 46.6 | 48.0 | 51.0 | 53.4 |
| BC2F4 Family | QTL11 | NCMEL0083076 | NCMEL0083077 | NU0218779 | NCMEL0083075 | NCMEL0083078 | NU0220333 | NU0244142 | NU0219710 |
|---|---|---|---|---|---|---|---|---|---|
| 1 | RP | AA | GG | GG | AA | AA | AA | AA | AA |
| 1 | DN | AA | GG | TT | TT | CC | AA | AA | AA |
| 2 | RP | AA | GG | GG | AA | AA | AA | AA | AA |
| 2 | DN | AA | GG | GG | TT | CC | AA | AA | AA |
| 3 | RP | AA | CC | GG | AA | AA | AA | AA | AA |
| 3 | DN | AA | GG | TT | TT | CC | GG | AA | AA |
| 4 | RP | AA | GG | GG | AA | AA | AA | AA | AA |
| 4 | DN | AA | GG | GG | TT | CC | GG | CC | AA |
| 5 | RP | AA | GG | GG | AA | AA | AA | AA | AA |
| 5 | DN | AA | GG | GG | TT | CC | GG | AA | AA |

| coded line name | generation | %RP | cM | WMV/ZyMV phenotypes | LG | 11 | 11 | 11 | 11 | 11 | 11 | 11 | 11 | 11 |
|---|---|---|---|---|---|---|---|---|---|---|---|---|---|---|
| | | | | | cM | 39.00 | 43.37 | 44.60 | 45.79 | 46.62 | 48.00 | 51.00 | 53.40 | 61.70 |
| | | | | | | NU0219106 | NCMEL0083630077 | NU0218779 | NCMEL0083830075 | NCMEL0083830078 | NU0220333 | NU0244142 | NU0219710 | NU0218204 |
| EKCZA12-0001AN | BC2F4 | 85.7 | 3.12 | R | | TT | GG | TT | TT | CC | AA | AA | AA | TT |
| EXCZA12-0002AN | BC2F4 | 90.3 | 5.95 | R | | TT | GG | GG | TT | CC | GG | CC | AA | TT |

FIG. 12A.

| Entry | LSMean_AUDPC_rep 1-5 | Std Error_rep 1-5 | LSMean_AUDPC_rep 6-10 | Std Error_rep 6-10 | LSMean_14dpi_rep 1-5 | Std Error_rep 1-5 | LSMean_14dpi_rep 6-10 | Std Error_rep 6-10 |
|---|---|---|---|---|---|---|---|---|
| BC2 recombinant | 80.64 | 2.59 | 74.17 | 2.42 | 8.86 | 0.25 | 8.80 | 0.24 |
| BC2 recombinant | 87.40 | 2.50 | 87.70 | 2.42 | 9.00 | 0.24 | 9.00 | 0.24 |
| BC2 recombinant | 83.11 | 2.59 | 83.90 | 2.80 | 8.93 | 0.25 | 8.92 | 0.28 |
| BC2 recombinant | 22.31 | 3.22 | 30.37 | 3.43 | 5.00 | 0.32 | 6.20 | 0.34 |
| BC2 recombinant | 52.72 | 2.74 | 36.32 | 2.51 | 8.59 | 0.27 | 6.86 | 0.25 |
| BC2 recombinant | 43.41 | 2.78 | 40.00 | 2.71 | 6.75 | 0.27 | 5.87 | 0.27 |
| BC2 recombinant | 61.60 | 2.85 | 39.38 | 2.60 | 7.26 | 0.28 | 7.16 | 0.26 |
| BC2 recombinant | 48.65 | 2.85 | 48.00 | 2.71 | 7.78 | 0.28 | 7.17 | 0.27 |
| BC2 recombinant | 76.08 | 2.59 | 53.36 | 2.51 | 7.85 | 0.25 | 7.00 | 0.25 |
| BC2 recombinant | 56.05 | 2.55 | 45.75 | 2.51 | 8.17 | 0.25 | 7.65 | 0.25 |
| BC2 recombinant | 86.43 | 3.41 | 84.22 | 3.80 | 8.99 | 0.34 | 8.67 | 0.38 |
| BC2 recombinant | 86.25 | 2.55 | 86.76 | 2.46 | 8.93 | 0.25 | 8.86 | 0.24 |
| BC2 recombinant | 86.08 | 2.59 | 84.13 | 2.42 | 8.99 | 0.25 | 8.87 | 0.24 |
| BC2 recombinant | 83.63 | 2.50 | 87.47 | 2.42 | 8.80 | 0.24 | 9.06 | 0.24 |
| BC2 recombinant | 85.13 | 2.64 | 83.88 | 2.46 | 8.77 | 0.26 | 8.45 | 0.24 |
| BC2 recombinant | 81.51 | 2.64 | 85.35 | 2.76 | 8.93 | 0.26 | 9.06 | 0.27 |
| BC2 recombinant | 46.02 | 2.38 | 35.61 | 2.85 | 6.33 | 0.29 | 6.12 | 0.26 |
| BC2 recombinant | 41.15 | 2.59 | 35.53 | 2.42 | 6.22 | 0.25 | 5.93 | 0.24 |
| BC2 recombinant | 60.75 | 2.55 | 56.37 | 2.42 | 8.44 | 0.25 | 7.60 | 0.24 |
| ME-9094 | 0.71 | 2.52 | 0.52 | 4.22 | 1.27 | 0.35 | 1.23 | 0.42 |
| WSH-39-1083-AN | 87.53 | 2.50 | 82.63 | 2.42 | 8.93 | 0.24 | 9.00 | 0.24 |
| MR1 | 68.48 | 2.92 | 62.73 | 3.12 | 8.74 | 0.29 | 7.78 | 0.31 |
| Pastis-1 | 61.02 | 2.68 | 67.55 | 3.32 | 7.17 | 0.26 | 7.14 | 0.33 |
| Pastis-2 | 12.07 | 2.64 | 20.45 | 2.46 | 3.69 | 0.26 | 4.53 | 0.24 |
| Paco | 3.92 | 2.74 | 5.29 | 2.55 | 1.80 | 0.27 | 2.04 | 0.25 |
| Topmark | 73.50 | 2.64 | 83.31 | 2.60 | 8.57 | 0.26 | 8.92 | 0.26 |
| Vedrantais | 87.99 | 2.79 | 87.64 | 2.76 | 9.00 | 0.27 | 9.00 | 0.27 |

FIG 12B.

| | l2 17.52 | l2 23.75 | l2 23.96 | l2 39.77 | l2 44.47 | l2 45.86 | l2 46.89 | l2 49.50 | l2 54.55 | l2 62.25 | l2 65.41 | l2 75.08 |
|---|---|---|---|---|---|---|---|---|---|---|---|---|
| | NU0018547 | NU0245767 | NU0220934 | NU0243766 | NU0218323 | NU0223980 | NU0229836 | NU0018516 | NU0220144 | NU0218796 | NU0220148 | NU0208863 |
| | GG | CC | CC | TT | GG | GG | GG | AA | CC | CC | AA | CC |
| | GG | AA | CC | TT | GG | GG | GG | AA | CC | CC | AA | CC |
| | GG | AA | TT | GG | GG | GG | GG | AA | CC | CC | AA | CC |
| | GG | AA | TT | GG | AA | GG | GG | AA | CC | CC | AA | CC |
| | GG | AA | TT | GG | AA | AA | GG | AA | CC | CC | AA | CC |
| | GG | AA | TT | GG | AA | AA | AA | AA | CC | CC | AA | CC |
| | GG | AA | TT | GG | AA | AA | AA | CC | CC | CC | AA | CC |
| | GG | AA | TT | GG | AA | AA | AA | CC | TT | CC | AA | CC |
| | GG | AA | TT | GG | AA | AA | AA | CC | TT | TT | AA | CC |
| | GG | AA | TT | GG | AA | AA | AA | CC | TT | TT | CC | CC |
| | CC | CC | CC | TT | GG | GG | GG | AA | CC | CC | AA | TT |
| | CC | CC | CC | TT | GG | GG | GG | AA | TT | TT | CC | TT |
| | CC | CC | CC | TT | GG | GG | GG | AA | TT | TT | CC | TT |
| | CC | CC | CC | TT | GG | GG | AA | CC | TT | TT | CC | TT |
| | CC | CC | CC | TT | GG | AA | AA | CC | TT | TT | CC | TT |
| | CC | CC | CC | TT | AA | AA | AA | CC | TT | TT | CC | TT |
| | CC | CC | CC | GG | AA | AA | AA | CC | TT | TT | CC | TT |
| | CC | CC | TT | GG | AA | AA | AA | CC | TT | TT | CC | TT |
| | CC | AA | TT | GG | AA | AA | AA | CC | TT | TT | CC | TT |

FIG. 13

| BC3 family | QTL12 | chr | 12 | 12 | 12 | 12 | 12 | 12 | 12 | 12 | 12 | 12 | 12 |
|---|---|---|---|---|---|---|---|---|---|---|---|---|---|
| | | cM | 29.96 | 31.74 | 39.77 | 42.24 | 43.38 | 44.47 | 44.28 | 45.88 | 46.89 | 35.48 | 48.42 |
| | | | NU0220934 | NU0219654 | NU0243358 | NU0219184 | NU0219714 | NU0218323 | NU0243527 | NU0220960 | NU0220836 | NU0219170 | NU0218164 |
| 1 | DN | | CC | AA | GG | CC | AA | AA | AA | GG | GG | GG | GG |
| 1 | RP | | CC | GG | TT | TT | GG | GG | AA | GG | GG | GG | GG |
| 2 | DN | | CC | GG | TT | TT | AA | AA | AA | GG | GG | GG | GG |
| 2 | RP | | CC | GG | TT | TT | GG | GG | AA | GG | GG | GG | GG |
| 3 | DN | | CC | GG | TT | CC | AA | AA | AA | GG | GG | GG | GG |
| 3 | RP | | CC | GG | TT | TT | GG | GG | AA | GG | GG | GG | GG |
| 4 | DN | | CC | GG | TT | CC | GG | GG | AA | GG | GG | GG | GG |
| 4 | RP | | CC | GG | TT | TT | GG | GG | AA | GG | GG | GG | GG |
| 5 | DN | | CC | GG | GG | CC | AA | AA | AA | GG | GG | GG | GG |
| 5 | RP | | CC | GG | TT | TT | GG | GG | AA | GG | GG | GG | GG |
| 6 | DN | | CC | GG | GG | TT | GG | GG | AA | GG | GG | GG | GG |
| 6 | RP | | CC | GG | TT | TT | GG | GG | AA | GG | GG | GG | GG |

FIG. 14

| coded line name | generation | %RP | cM | CMV phenotypes | LG<br>cM<br>NJ-02196554 | 12<br>31.74 | 12<br>39.77<br>NJ-02433268 | 12<br>42.34<br>NJ-02191984 | 12<br>43.38<br>NJ-02197114 | 12<br>44.47<br>NJ-02183323 | 12<br>44.36<br>NJ-02438527 | 12<br>45.88<br>NJ-02209980 | 12<br>46.89<br>NJ-02208836 | 12<br>48.42<br>NJ-02181164 |
|---|---|---|---|---|---|---|---|---|---|---|---|---|---|---|
| EXCZA12-0004AN | BC2F4 | 85.0 | 6.24 | HR | GG | | TT | CC | AA | AA | GG | AA | GG | GG |
| EXCZA12-0005AN | BC2F6 | 92.9 | 3.28 | IR | GG | | TT | CC | AA | AA | AA | GG | GG | GG |
| EXCZA12-0006AN | BC2F6 | 94.4 | 3.10 | R | GG | | GG | CC | AA | AA | AA | GG | GG | GG |

MULTIPLE-VIRUS-RESISTANT MELON

CROSS REFERENCE TO RELATED APPLICATIONS

This application claims benefit of U.S. Provisional Application No. 61/692,643, filed Aug. 23, 2012, herein incorporated by reference in its entirety.

INCORPORATION OF SEQUENCE LISTING

The Sequence Listing, which is a part of the present disclosure, includes a computer readable 12.5 KB file created on Aug. 20, 2013 entitled "SEMB006US_ST25.txt" comprising nucleotide and/or amino acid sequences of the present invention submitted via EFS-Web. The subject matter of the Sequence Listing is incorporated herein by reference in its entirety.

FIELD OF THE INVENTION

The invention relates to the field of plant breeding. More specifically, it relates to methods for producing melons resistant to multiple viruses, and plants produced therefrom.

BACKGROUND OF THE INVENTION

Melon fruits are highly appreciated worldwide and are often eaten as a fresh product. Melons are members of the gourd family (Cucurbitaceae), a class of trailing annual vines that also includes squash, pumpkin and cucumber. They have large broad leaves, stems covered in light prickles and small yellow flowers. The fruit themselves are soft fleshed with a central cavity containing seeds, surrounded by a thick protective rind.

Taxonomically, melons are broadly divided into two groups: watermelons (species *Citrullus lanatus*) and muskmelons (species *Cucumis melo* L.). *C. melo* includes a wide variety of cultivars producing fruits of different shape, external appearance and flesh color, including such melons as Canary, Cantaloupe (including Western Shipper, North American and Charentais types), Casaba, Hami, Honeydew, Navajo Yellow, Piel de Sapo, Santa Claus, Sugar melon, Ambrosia, Bailan, Galia, Ogen, Persian, and Sharlyn.

Certain viruses are capable of infecting melons and causing crop damage and loss in many varieties. Examples of viral pathogens that may impact melon cultivation include Cucumber Mosaic Virus (CMV), Watermelon Mosaic Virus (WMV), and Zucchini Yellow Mosaic Virus (ZYMV).

SUMMARY OF THE INVENTION

In a first aspect, the invention provides a melon plant comprising resistance to Zucchini Yellow Mosaic Virus (ZYMV) and Watermelon Mosaic Virus (WMV), wherein the plant further comprises at least one trait selected from the group consisting of: produces fruit with a width to length ratio of at least 0.5; produces fruit with orange flesh color, green flesh color, or white flesh color; demonstrates fruit Brix≥9.5° Bx; displays resistance to CMV; displays resistance to MNSV; displays resistance to PRSV; and displays resistance to Powdery Mildew.

In one embodiment, the invention provides such a melon plant, wherein the at least one trait is a width to length ratio of at least 0.5. In other embodiments, the melon plant comprises at least one trait selected from the group consisting of orange flesh color, green flesh color, and white flesh color. In another embodiment of the melon plant, the at least one trait is Brix≥9.5° Bx. In yet another embodiment the at least one trait is resistance to CMV. In still yet another embodiment, the at least one trait is resistance to Powdery Mildew. In other embodiments the at least one trait is resistance to MNSV, or resistance to PRSV.

The invention further provides a part of such a melon plant, wherein the plant part is selected from the group consisting of: a seed, a root, a leaf, a stem, pollen, an ovule, an anther, a pistil, and a cell. A tissue culture of regenerable cells of the melon plant is also provided by the invention. In a particular embodiment, the tissue culture may comprise cells or protoplasts from a plant part selected from the group consisting of embryo, meristem, cotyledon, pollen, leaf, anther, root, root tip, pistil, flower, and seed.

Another aspect of the invention provides such a melon plant, which is inbred. Alternatively, the melon plant may be a hybrid.

A further aspect of the invention provides a method of determining the genotype of a melon plant comprising resistance to Zucchini Yellow Mosaic Virus (ZYMV) and Watermelon Mosaic Virus (WMV), wherein the plant further comprises at least one trait selected from the group consisting of: produces fruit with a width to length ratio of at least 0.5; produces fruit with orange flesh color, green flesh color, or white flesh color; demonstrates fruit Brix≥9.5° Bx; displays resistance to CMV; displays resistance to MNSV; displays resistance to PRSV; and displays resistance to Powdery Mildew; wherein the method comprises: obtaining a sample of nucleic acids from said plant and detecting in said nucleic acids a plurality of polymorphisms.

Also provided by the invention is a method of identifying a melon plant that displays resistance to Zucchini Yellow Mosaic Virus (ZYMV) and Watermelon Mosaic Virus (WMV), the method comprising: detecting in a first melon plant at least one allele of a marker that is associated with WMV and ZYMV resistance, wherein the marker is genetically linked within 10 centiMorgans (cM) of marker NU0219106 or NU0219710 on melon chromosome 11. In one embodiment of such a method, the marker is localized within a chromosomal interval defined by and including the terminal markers NU0219106 and NU0219710 on melon chromosome 11. In another embodiment, the marker is localized within a chromosomal interval defined by and including the terminal markers NCMEL008383077 and NU0220333 on melon chromosome 11. In particular embodiments of the method, the marker is selected from the group consisting of: NU0219106, NU0218916, NU0219099, NU0218656, NCMEL008383076, NCMEL008383077, NU0218779, NCMEL008383075, NCMEL008383078, NU0220333, NU0219293, NU0218835, NU0244142, and NU0219710.

In some embodiments, the detecting comprises detecting at least one allelic form of a single nucleotide polymorphism by PCR, single strand conformational polymorphism analysis, denaturing gradient gel electrophoresis, cleavage fragment length polymorphism analysis, TaqMan assay, and/or DNA sequencing.

The invention further provides a method of identifying a melon plant that displays resistance to Zucchini Yellow Mosaic Virus (ZYMV), the method comprising: detecting in a first melon plant at least one allele of a marker which is associated with ZYMV resistance, wherein the marker is genetically linked within 2 centiMorgans (cM) of marker NU0218531 on melon chromosome 2. In certain embodiments, the marker is localized within a chromosomal interval defined by and including the terminal markers CMBR041 and NU0218531 on melon chromosome 2. In particular embodiments of the method, the marker is selected from the group consisting of CMBR041, and NU0218531.

The method may further comprise detecting at least one allele of a marker that is associated with CMV resistance, and at least one allele of a marker that is associated with WMV and ZYMV resistance. Thus, in such a method, at least one allele of a marker associated with resistance to CMV is detected in the melon plant within a chromosomal interval defined by and including the termini NU0243358 or NU0218323 on melon chromosome 12; or within a chromosomal interval defined by and including the termini NU0219184 and NU0218323 on melon chromosome 12; or within a chromosomal interval defined by and including the termini NU0220476 or NU0219006 on melon chromosome 2, or wherein the marker is genetically linked within 10 cM of markers NU0243358 or NU0219184 or NU0218323, or genetically linked within 10 cM of markers NU0220476 or NU0219006.

In certain embodiments of the methods, the resistance is assayed by exposing the plant to WMV or ZYMV, and identifying plants with reduced disease symptom expression relative to control plants.

In some embodiments of the methods, the at least one allele of a marker associated with resistance to WMV or ZYMV is found in melon line ME8094, a representative sample of seed of which has been deposited under NCIMB accession number 41653. The invention may further comprise selecting the first melon plant from a population of melon plants based on the presence of said allele of a marker which is associated with the resistance to ZYMV or WMV. In particular embodiments the method further comprises crossing a selected first melon plant with a second melon plant to obtain a progeny plant of a subsequent generation. Certain embodiments of the methods of the invention further comprise backcrossing the progeny plant of a subsequent generation and at least one further subsequent generation thereof to a recurrent parent until a backcrossed progeny plant is produced that comprises resistance to WMV or ZYMV.

Another aspect of the invention provides a method of producing a melon plant having resistance to WMV and ZYMV, comprising the steps of: (a) crossing a plant of melon line ME8094, or a progeny thereof comprising resistance to WMV and ZYMV, derived from said line ME8094, with a second melon plant having at least one desired trait, a representative sample of seed of said line having been deposited under NCIMB accession number 41653; and (b) selecting at least a first progeny melon plant resulting from the crossing that comprises resistance to WMV, and ZYMV, and at least one desired trait.

In some embodiments of such a method, the desired trait is selected from the group consisting of: a width to length ratio of at least 0.5; orange flesh color; Brix≥9.5° Bx; resistance to CMV; resistance to MNSV; resistance to PRSV; and resistance to Powdery Mildew. In other embodiments, selecting the first progeny comprises identifying the presence of at least a first genetic marker in the first progeny that is genetically linked to a locus contributing to resistance to WMV, ZYMV, or CMV; wherein the marker genetically linked to a locus contributing to WMV or ZYMV resistance maps to chromosome 11, and wherein a marker genetically linked to a locus contributing to CMV resistance maps to chromosome 2 and/or 12. In particular embodiments, selecting the first progeny further comprises selecting the progeny based on the presence of a plurality of genetic markers from the second melon plant present in the progeny. Thus, in some embodiments the invention provides a method wherein the genetic marker linked to a locus contributing to WMV or ZYMV resistance is genetically linked within 10 cM of marker NU0219106 or NU0219710 on melon linkage group 11. In further embodiments the genetic marker linked to a locus contributing to CMV resistance is genetically linked within 10 cM of marker NU0243358 or NU0218323 on melon linkage group 12 or within 10 cM of marker NU0220476 or NU0219006 on melon linkage group 2.

In certain embodiments the genetic marker is selected from the group consisting of: NU0219184, NU0219714, NU0220980, NU0243527, NU0220836, NU0218164, NU0218516, NU0218074, NU0218603, and NU0220144. In other embodiments the genetic marker linked to a locus contributing to CMV resistance is genetically linked within 10 cM of marker NU0220476 or NU0219006 on melon linkage group 2. In still other embodiments the genetic marker is selected from the group consisting of: NU0218624, NU0219047, NU0220488, and NU0220264. In particular embodiments the genetic marker linked to a locus contributing to WMV or ZYMV resistance is NU0218656 or NU0218779.

Further embodiments of such a method comprise the step of: (c) crossing the progeny plant with itself or a third plant to produce a progeny plant of a subsequent generation. Yet other embodiments further comprise the steps of: (d) crossing the progeny plant of a subsequent generation with itself or a second plant; and (e) repeating steps (c) and (d) for at least an additional 3-10 generations to produce an inbred melon plant derived from melon line ME8094, a representative sample of seed of said line having been deposited under NCIMB accession number 41653. In particular embodiments said progeny plant of a subsequent generation is selected for crossing based on the presence of resistance to WMV or ZYMV, and the desired trait. In certain embodiments the progeny plant of a subsequent generation is selected at each generation for crossing based on the presence of the resistance to WMV or ZYMV, and the desired trait. The method may further comprise selecting the progeny plant of a subsequent generation by identifying the presence of at least a first genetic marker in the first progeny that is genetically linked to a locus contributing to resistance to WMV and ZYMV. In some embodiments, selecting the progeny plant of a subsequent generation further comprises selecting the progeny based on the presence of a plurality of genetic markers from the second melon plant present in the progeny. In further embodiments step (e) is repeated a sufficient number of generations to obtain an inbred melon plant that comprises resistance to WMV, and ZYMV, and further comprises the agronomic traits of the second melon plant.

Yet another aspect of the invention relates to a melon plant, or a part thereof, produced by such a method. A part of such a melon plant, wherein the part is selected from the group consisting of: a fruit, a leaf, a root, a stem, pollen, an ovule, a cell, and a seed, is also provided, as is hybrid melon seed produced by such a method.

Thus, in certain embodiments, the invention provides a melon seed defined as produced by a method comprising: crossing variety ME8094, a representative sample of which has been deposited with the NCIMB, Aberdeen, Scotland under accession number NCIMB 41653, or a progeny thereof, with a second melon variety; detecting the genotype or virus resistance phenotype of a progeny plant of a subsequent generation; and harvesting seed thereof.

An inbred melon seed of line ME8094, a representative sample of which has been deposited with the NCIMB under accession number NCIMB 41653, is a further aspect of the invention, as is a plant grown from the seed of ME8094, and a part of the plant. In some embodiments the plant part is selected from the group consisting of: a fruit, a leaf, a root, a stem, pollen, an ovule, a cell, and a seed.

Yet another aspect of the invention provides a melon plant, or a part thereof, having all the physiological and morphological characteristics of a plant of melon line ME8094. A tissue culture of regenerable cells of the plant is also provided. In further embodiments, the plant of melon line ME8094 further comprises a single locus conversion. In other embodiments the plant comprises a transgene.

Another aspect of the invention provides a method of producing melon seed, comprising crossing the plant of melon line ME8094 with itself or a second melon plant. Thus, the invention also provides an F1 hybrid seed produced by such a method, as well as an F1 hybrid plant produced by growing such a seed.

In still another aspect, the invention provides a method of vegetatively propagating a melon plant comprising the steps of: (a) collecting tissue capable of being propagated from a plant of melon line ME8094; (b) cultivating said tissue to obtain proliferated shoots; and (c) rooting said proliferated shoots to obtain rooted plantlets. Certain embodiments of this method further comprise growing plants from said rooted plantlets.

BRIEF DESCRIPTIONS OF THE FIGURES

FIG. 1 diagrams the melon genetic map, showing relative positions of selected traits of interest on linkage groups (Chromosomes) 1-12.

FIG. 4 provides a table showing relative disease scores (1-10 scale) and ELISA scores of selected melon lines when challenged with listed pathogen(s) (i.e. viral isolate).

FIGS. 5A-5C provide disease rating scores and AUDPC for plants of melon varieties inoculated with indicated CMV strain, scored at 8, 15, and 30 days after infection. (MDI-8, -15, -30). Entry # and Variety columns in 5A apply as corresponding labels also for the FIG. 5B and FIG. 5C data columns.

Figure 6A:
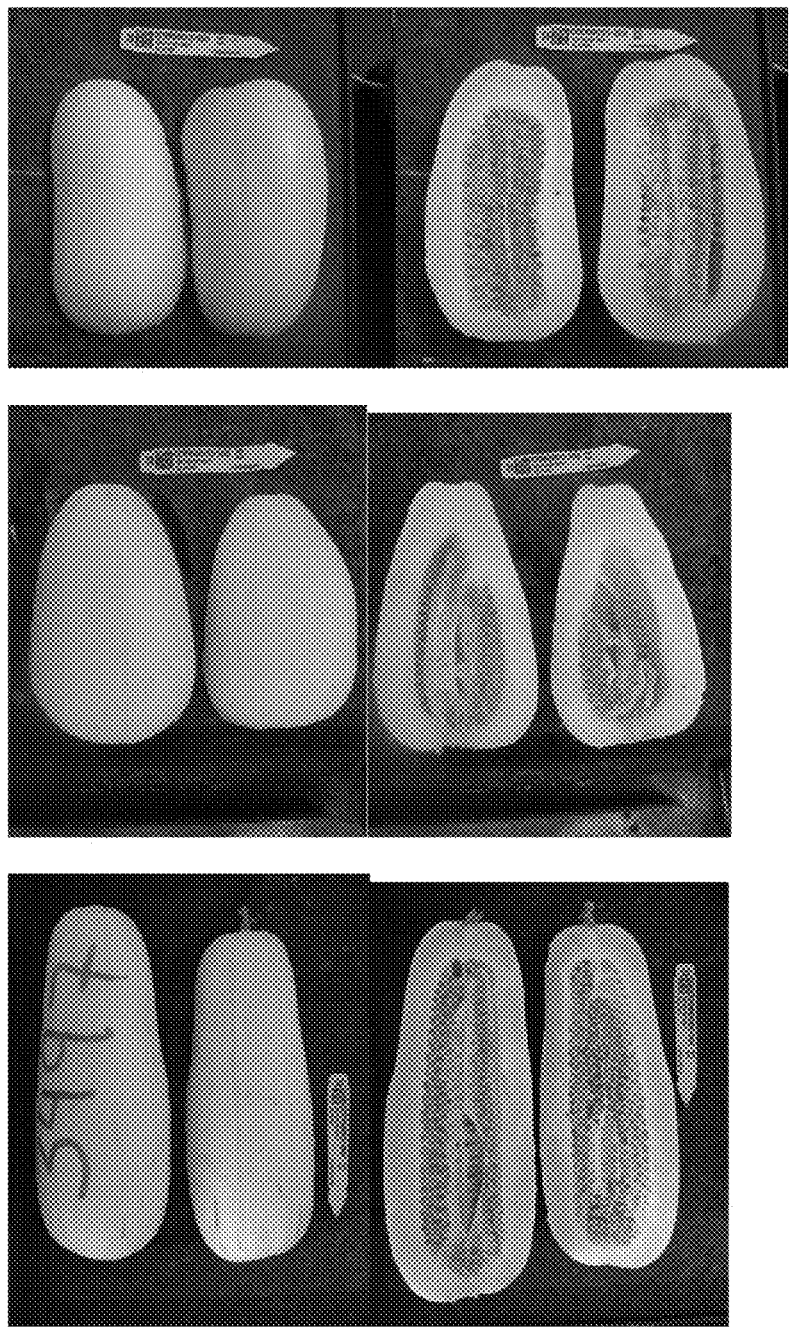
Figure 6B:
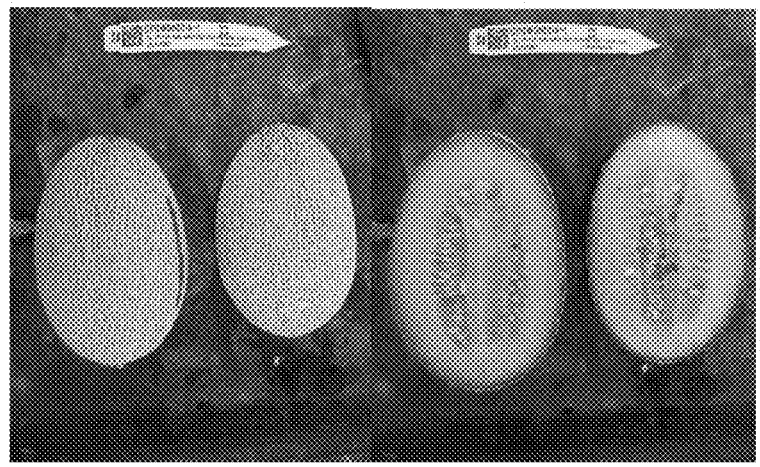
Figure 6C:
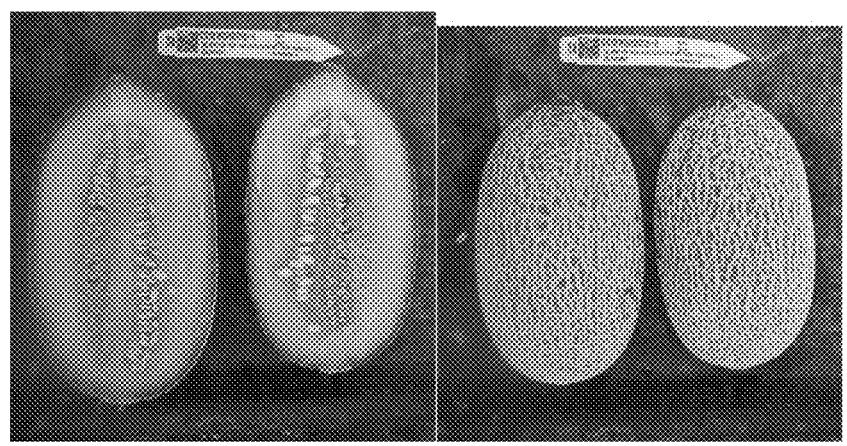
Figure 6D:
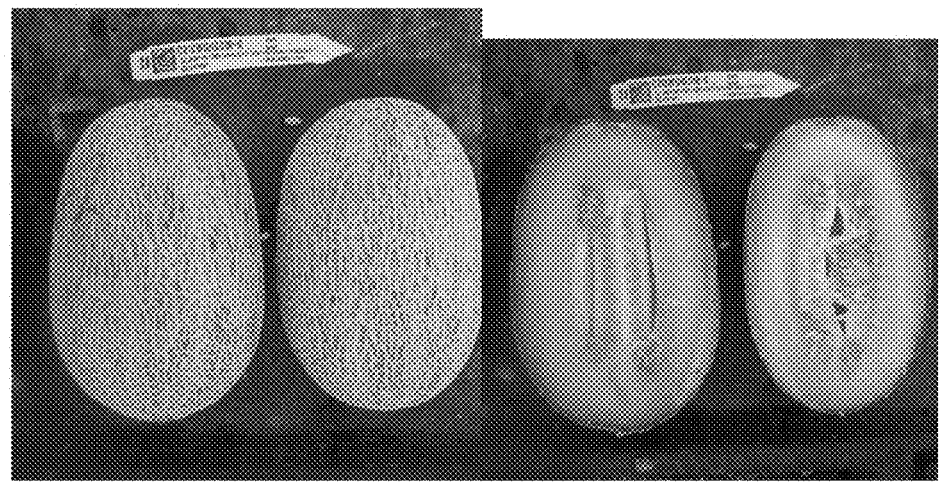
Figure 6E:
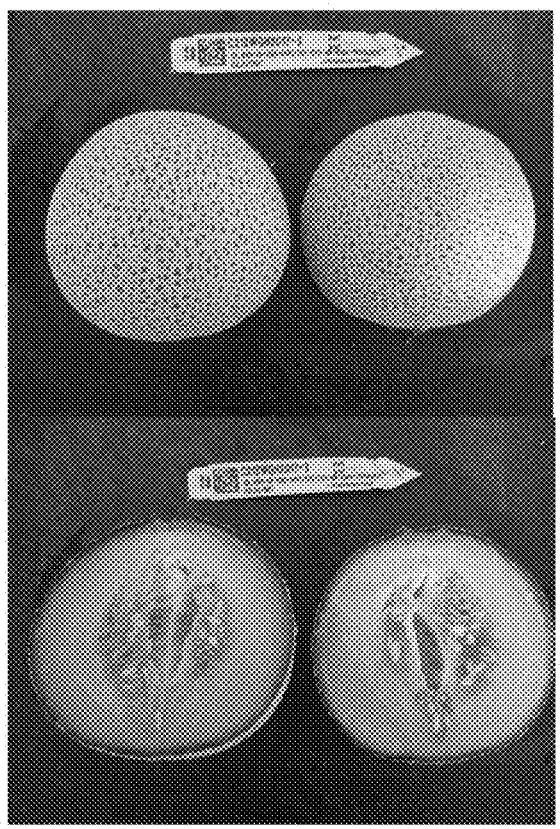

FIGS. 6A-6E provide photographs of fruit from ME8094 and BC2 lines derived therefrom. FIG. 6A: fruit of ME8094; FIG. 6B: fruit of C2_WSH-39-1083-AN*3/EXC-C210-ME-8094-1:0027.0018.0006; FIG. 6C: fruit of C2_WSH-39-1083-AN*3/EXC-C210-ME-8094-1:0080.0088.0005; FIG. 6D: fruit of C2_WSH-39-1083-AN*3/EXC-C210-ME-8094-1:0063.0007.0010.0147; FIG. 6E: fruit of C2_WSH-39-1083-AN*3/EXC-C210-ME-8094-1: 0018.0013.0002.0145.

Figure 7:
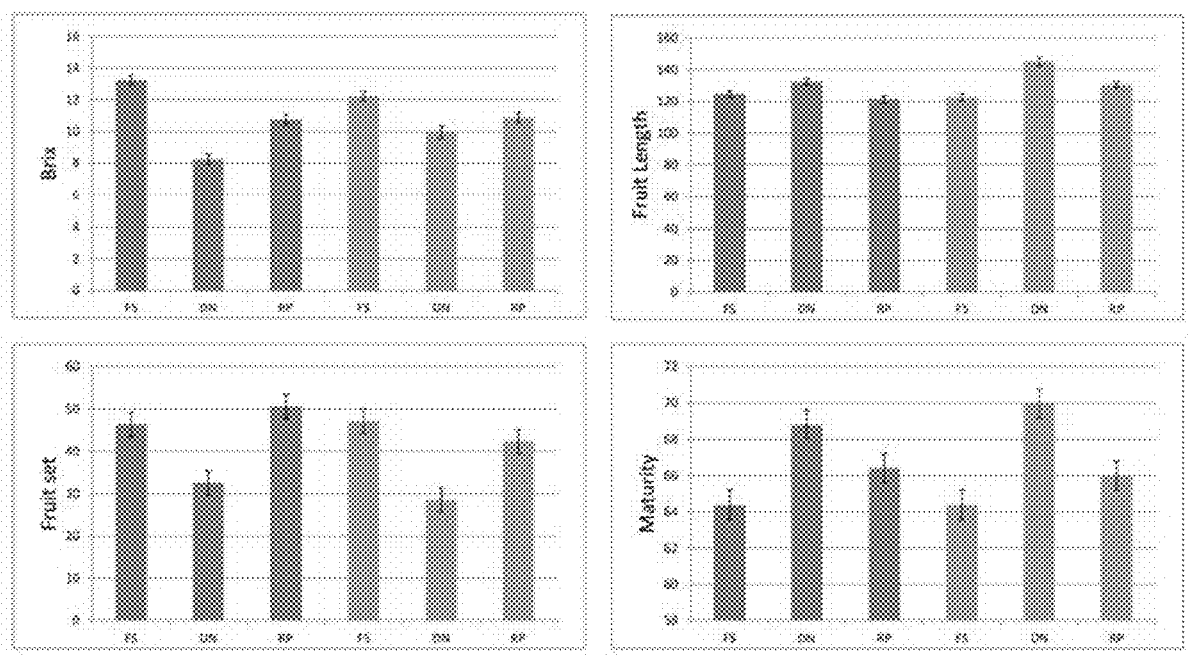

FIG. 7 illustrates additional trial results for traits of each of the two tested GAL BC3 families carrying the ZYMV/WMV QTL11 introgression (homozygous donor (DN) and recurrent parent (RP) alleles next to the unconverted inbred lines (FS)) respectively.

Figure 8:
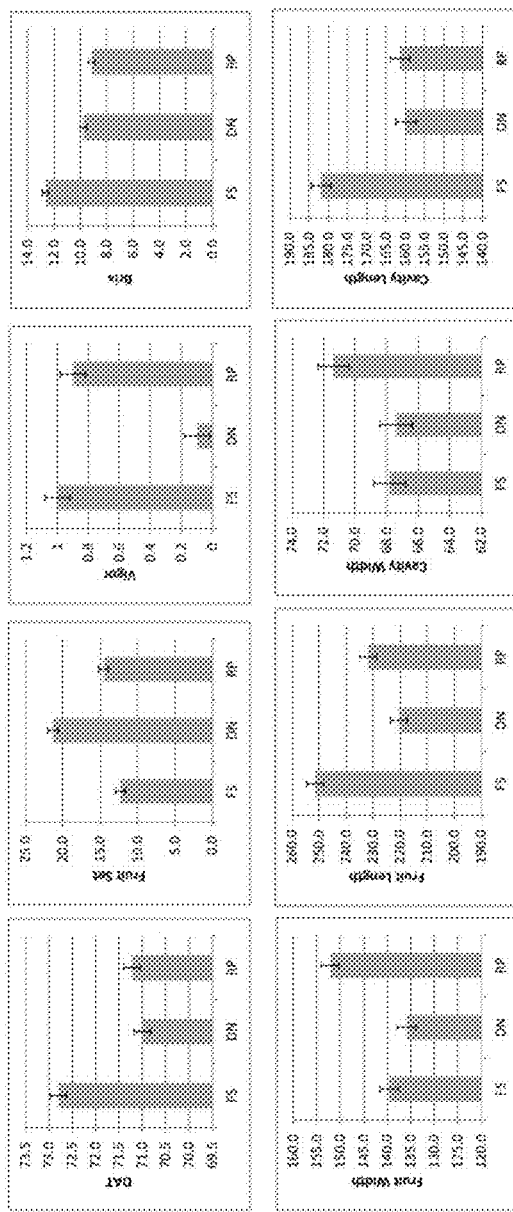

FIG. 8 illustrates data of Table 11 (trial of the AMA-188-DECO-AN MABC conversion carrying the ZYMV/WMV QTL11 introgression), in graphic form. Results from homozygous donor (DN) and recurrent parent (RP) alleles are next to the unconverted inbred lines (FS). One BC4 family was evaluated for listed phenotypic traits. Least square means and least square differences are shown.

FIG. 9. Genotypes at ZYMV/WMV QTL11 of the trialed isogenic lines: donor introgressions span 2.2 to 9.1 cM. Dark highlighted or underlined markers demonstrate the most likely interval where the trait resides.

FIG. 10. Representation of fingerprinting data and allele information from two events carrying the ME8094 introgression at the ZYMV/WMV QTL11 locus that lacked linkage drag (deleterious phenotype) and were shown to be resistant to ZYMV and WMV.

Figure 11:
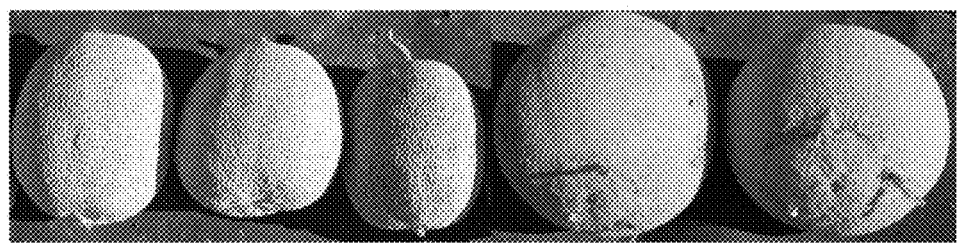

FIG. 11. Photographs showing typical size/shape and blossom end scar of melons carrying introgressions at the CMV QTL12 genomic region.

FIGS. 12A-B. Genotypes and phenotypes (lsmeans of AUDPC and 14 dpi score for each of the two timepoints described above) of available entries with recombination events in the CMV QTL12 interval and controls. In FIG. 12B, darker highlighting corresponds to ME8094 introgressions at given marker locations, and lighter highlighting to introgressions of the recurrent parent WSH-39-1083-AN. Putative location of the genetic factor controlling CMV is in the interval of NU0243358 and NU0218323.

FIG. 13. Genotypes at the CMV QTL12 of the isogenic lines trialed. The fine-mapped region of the QTL is shown within the bold lines and markers at positions 43.38 and 44.47 cM are the most closely linked to the trait.

FIG. 14. Three events carrying the ME8094 introgression at the CMV QTL12 locus that lacked linkage drag were shown to be intermediate resistant (IR), resistant (R) and highly resistant (HR) under CMV pressure.

DETAILED DESCRIPTION OF THE INVENTION

The invention provides methods and compositions for producing multiple virus resistant melon plants exhibiting resistance to Watermelon Mosaic Virus (WMV) and Zucchini Yellow Mosaic Virus (ZYMV), and Cucumber Mosaic Virus (CMV), while also exhibiting one or more agronomically acceptable traits such as high Brix content, desirable fruit flesh color (e.g. orange, green, or white), desirable fruit shape (length-width ratio), non-pentamerous fruit, and lack of andromonoecious flowers, among others. Methods of breeding and selecting multiple virus resistant melon lines are further provided, as well as plants, seeds, and fruit of such multiple virus resistant melons. Also disclosed herein are molecular markers that are linked to quantitative trait loci ("QTL") contributing to such plant virus resistance.

Surprisingly, the inventors have been able to develop methods and compositions that allow, for the first time, production of plants with multi-virus resistance while avoiding or minimizing deleterious traits that have thus far been associated with such viral resistance. Examples of deleterious traits that have been associated with attempts to obtain resistance to individual viruses include weak plants with pentamerous, flat, poorly netted fruit, poor net formation, low fruit set, foliar necrosis, and andromonoecy. In contrast, the invention provides methods and compositions that permit combination of multi-virus resistance with the ability to produce a commercially acceptable melon crop from a single line.

The ability to produce virus resistant plants is also hampered by difficulties in phenotyping and the limited repeat-ability of phenotyping for virus resistance. This includes problems associated with limited heritability of some resistance phenotypes. For instance, with regard to CMV, inconsistent disease reactions may occur in sequential tests on selected breeding lines.

The invention represents a significant advance in the art in that it provides, in certain embodiments, methods and compositions permitting introgression or resistance to selected viruses and combinations of viruses into a commercially acceptable genetic background. In specific embodiments of the invention, a QTL conferring WMV and ZYMV resistance is identified and defined by the map interval bounded by markers NU0218779 and NU0218835 (see Table 4), corresponding to 44.6-49 cM on melon chromosome 11. A QTL is also identified herein that confers resistance to CMV and is located on chromosome 12 in the interval bounded by markers NU0243358 and NU0218323, spanning the interval of 39.7-44.47 cM. Additionally, a second QTL that confers resistance to CMV is identified herein that is located on chromosome 2 in the interval bounded by markers NU0220476 and NU0219006, spanning the interval of 80.1-118.5 cM.

Further, the zym-1 gene specifying resistance to ZYMV was also mapped, and markers CMBR041 (Diaz et al., *BMC Plant Biol.* 11:111, 2011), NU0218808, NU0218497, NU0218113, NU0244013, NU0244734, NU0220855, NU0244741, NU0220997, NU0220034, NU0220178, NU0218179, NU0243740, and NU0218531, corresponding to the interval from ~3.2-5.7 cM on the genetic map of melon chromosome 2 were found to be tightly linked to this gene.

Through use of the corresponding markers provided herein and/or other markers that may be linked thereto, one of skill in the art may use genetic markers to introgress and combine ("stack") virus resistance traits in commercially relevant hybrid varieties and melon lines.

In accordance with the invention, identified QTL may be introgressed into any different melon genetic background. Thus, using the methods of the invention and starting from the genetic sources identified herein or available in the art, a melon plant of any genotype may be produced that further comprises the desired viral resistance, including WMV, ZYMV, and CMV. In addition, such plants may be prepared to comprise other desired traits, for example elite agronomic and fruit quality traits as desired.

Sources of particular resistances are known in the art, although the ability to combine such sources in a commercially relevant way as described herein has been lacking. An example is melon lines derived from the source PI 414723 having resistance to one or more of ZYMV, CMV, or WMV, such as 'Hannah's Choice F1' (Henning et al., 2005, *Hort. Sci* 40: 492-493). While the source provides viral resistance, the heritability of the viral resistance is often complex, the genetic position of resistance unknown, the resistance trait is associated with deleterious traits, and there are problems with pathogen specificity. For instance, ZYMV occurs in three pathotypes designated as 0, 1 and 2. The ZYMV resistance trait from accession PI 414723, specified by the zym-1 gene, confers resistance to pathotype 0 but does not provide any resistance against pathotype 2. Furthermore, infection with pathotype 1 may result in large scale necrosis in plants carrying the ZYMV resistance trait from accession PI 414723. The herein described WMV/ZYMV resistance locus provided on chromosome 11 is valuable as it provides resistance to two viruses, strong resistance to WMV, no or very low virus titer after mechanical viral inoculation, and a source for resistance to ZYMV which is not associated with the foliar necrosis typical of the previously identified zym-1 gene.

With respect to its underlying genetics, ZYMV resistance from accession PI 414723 is polygenic (Danin-Poleg et al., *Euphytica* 93:331-337, 1997), meaning that multiple loci are required to confer resistance. This hampers breeding efforts as only a portion of progeny plants in a breeding program will carry all or even some of the genes necessary to confer an adequate level of resistance. Additionally, ZYMV resistance in accession PI 414723 is linked to andromonoecy (plants having both hermaphrodite and male flowers). Since elite melon breeding lines are desirably monoecious lines (plants having separate male and female flowers) and monoecious parental lines do not require tedious and expensive hand emasculation to avoid self-pollination, andromonoecy is considered to be an undesirable characteristic. Also, fruit of monoecious F1 hybrids lack the undesirable blossom end, thus producing fruits of higher quality.

Another problem associated with virus resistance originating from PI 414723 is the lack of further characterization of these resistance traits regarding WMV. In contrast to the observation in Henning et al. (supra) that PI 414723-4, a resistance-selected line of PI 414723, is resistant to WMV, other researchers could not confirm the presence of WMV resistance in PI 414723 (e.g. Díaz et al. 2003, *Plant Dis.* 87:960-964). In addition, the WMV resistance trait from accession PI 414723 did not confer resistance to some isolates of WMV (Anagnostou et al., 2003, J. *Euphytica* 116:265-270), and therefore cannot serve as source for broad WMV resistance.

WMV resistance has been described, such as the recessive trait in *C. melo* accession TGR-1551 (Díaz-Pendón et al. 2005 *Phytopathology* 95:840-846; and Díaz et al. supra). Like the WMV resistance originating from PI 414723, the WMV resistance from TGR-1551 does not confer resistance to some isolates of WMV (see FIG. 4). Hence, *C. melo* accession TGR-1551 is less desirable as a donor of the trait "WMV resistance" in breeding programs. Incorporating a previously known source for CMV resistance may be problematic in breeding for such resistance as well, in that it is linked to an undesirable trait that results in pentamerous fruit, as further discussed below. Thus the newly disclosed QTL for CMV resistance is also of great benefit for melon breeding.

Genetic Mapping of Loci Controlling Virus Resistance

Viruses of interest, sources (donors) for resistance, and mapping populations used to identify loci controlling virus resistance are listed in Table 1. A summary of genetic parameters relating to identified virus resistance traits is found in Table 2. Genetic parameters listed in Table 2 include the linkage group and projected location on the chromosome of the resistance loci; the additive (Add. Effect) and dominance (Dom. Effect) effects of the favorable allele at each locus; the percent of phenotypic variance ("Model $R^2$") accounted for by genotype at each locus; and the mean phenotypes of families in the mapping populations with genotypes homozygous for the unfavorable allele (Pheno. Homoz. Unfav), heterozygous (Pheno. Het), and homozygous for the favorable allele (Pheno. Homoz. Fav). The phenotypic rating scales used for each virus are 1 to 3=resistant; 4 to 6=intermediate resistant; 7 to 9=susceptible. The specific phenotypes associated with each numerical score differ per virus based on specific manifestations of the diseases, but the three general categories of resistant; intermediate resistant; susceptible are consistent.

TABLE 1

Virus resistance traits, sources, and allele information used to identify loci controlling resistance to viruses in melon. ("Generation" refers to the progeny generation of a given mapping population.

| Trait | Source of Favorable Allele | Gene/ QTL ID | Unfavorable Allele Parent | Favorable Allele Parent | Generation |
|---|---|---|---|---|---|
| CMV | Mbnr992 | QTL12 | GA35Pmt | Mbnr992 | F6 |
| CMV | PI161375 | QTL12 | Vedrantais | PI161375 | F6 |
| WMV | Mbnr992 | W/z | GA35Pmt | Mbnr992 | F6 |
| ZYMV | Mbnr992 | W/z | GA35Pmt | Mbnr992 | F6 |
| ZYMV | PI414723 | zym-1 | Vedrantais | PI414723 | F6 |

CMV, WMV and ZYMV resistance was mapped from source Mbnr992 (Table 1), which was developed by self-pollination of ME8094. Mbnr992 carries resistances to CMV, WMV, and ZYMV. Inheritance of the CMV and ZYMV resistances from Mbnr992 is recessive. Inheritance of WMV resistance from Mbnr992 is mainly dominant, although heterozygotes may show intermediate resistance depending on weather conditions and the level of virus pressure. When using Mbnr992 as the resistance donor for breeding, segregating populations demonstrated high correlation of resistance to both WMV and ZYMV. This suggested tight linkage of loci (or a single locus) controlling resistance to these two viruses, which was confirmed by additional mapping studies.

CMV resistance was mapped from two sources, Mbnr992 and PI161375 (see Table 1). Mbnr992 is discussed above. An F6 RIL population from the cross Mbnr992×GA35Pmt was phenotyped and genotyped to map the genetic location of the resistance trait. The parent line GA35Pmt is susceptible to CMV, WMV, and ZYMV. PI161375 is resistant to CMV and MNSV (MNSV resistance is conferred by the nsv locus). An F6 RIL population from the cross PI161375× Vedrantais was phenotyped and genotyped. The parent line Vedrantais is a Charentais type, inbred line susceptible to CMV and MNSV.

QTL for CMV resistance in Mbnr992×GA35Pmt and in PI161375×Vedrantais populations were identified. Both populations carry a QTL on chromosome 12. An allelism test including >1000 F2 plants from Mbnr992×Virgos (a CMV-resistant derivative of PI161375×Vedrantais) supported allelism of the major effect(s) for CMV resistance from the two sources (Mbnr992 and PI161375). The mapping and allelism test support a common QTL on chromosome 12. A second CMV resistance QTL was also identified on chromosome 2 in the Mbnr992 cross (Table 2).

of interest, including multiple (stacked) virus resistance. "PM" denotes a source for resistance to Powdery Mildew of melon. Likewise, WMV, ZYMV, and CMV denote the corresponding virus resistance traits. For instance, "CMV12" indicates the presence in a parent plant of a genetic trait conferring CMV resistance, and which is localized on melon Linkage Group 12. Other desirable agronomic traits such as additional disease resistance(s), orange or green fruit flesh color, rounded fruit, and enhanced Brix, among others, may also be contemplated for inclusion in the resulting F1 hybrid plants. A skilled worker may adjust the breeding strategy as needed, for instance in view of disease resistance and other traits desired for a given market or melon growing geographic region.

TABLE 3

Exemplary breeding strategy for traits that may be combined to produce an F1 hybrid multiple virus resistant melon.

| Female parent | | | Male parent | | |
|---|---|---|---|---|---|
| PM | WMV/ ZYMV | CMV12 | CMV02 | PM | WMV/ ZYMV | CMV12 |
| PM | WMV/ ZYMV | CMV12 | | PM or increased Brix | WMV/ ZYMV | CMV12 |

Improved Melon Lines with Multi-Virus Resistance

Resistance to particular pathogens such as CMV, WMV, and ZYMV have been described. For ZYMV and WMV, resistant accession PI 414723 was reported by Pitrat and Lecoq (1984, *Euphytica* 33: 57) and Anagnostou et al., 2003 (*J. Euphytica* 116: 265-270). The resistance is heritable but associated with andromonoecy, which is undesirable in melon lines used for breeding (Pitrat et al., *Phytopathol.* 70:958-961, 1980). Additionally, PI 414723 displayed a necrotic phenotype upon infection with ZYMV pathotype 1. Necrosis is often associated with disease resistance; thus, heavy infection with pathotype 1 could lead to reduction of plant development and yield loss.

In contrast to the previous problems, ZYMV resistance is provided by the present invention not linked to the andromonoecious characteristic. This finding thus facilitates the production of a homozygous ZYMV resistant, monoecious line that can be used as donor in breeding programmes for introgression of these traits into new cultivars.

In contrast to PI414723, the melon line ME8094 described herein was found to be fully resistant to ZYMV

TABLE 2

Genetic parameters of selected loci controlling resistance to viruses in melon.

| Trait | Source of Favorable Allele | Gene/ QTL ID | Linkage Group | Projected position on Chrom. | Add. Effect | Dom. Effect | Model R^2 | Pheno. Homoz. Unfav. | Pheno. Het. | Pheno. Homoz. Fav. |
|---|---|---|---|---|---|---|---|---|---|---|
| CMV | Mbnr992 | QTL12 | 12 | 35-47 | -2.00 | -0.09 | 0.52 | 6.1 | | 2.1 |
| CMV | Mbnr992 | QTL02 | 2 | 97-107 | -0.74 | -0.74 | 0.10 | 4.6 | 3.1 | 3.1 |
| CMV | PI161375 | QTL12 | 12 | 35-47 | -1.50 | NA | 0.41 | 7.8 | NA | 4.6 |
| WMV | Mbnr992 | W/z | 11 | 44-53 | 0.00 | Complete | na | Sus. | Res. | Res. |
| ZYMV | Mbnr992 | W/z | 11 | 44-53 | 0.00 | 0.00 | na | Sus. | Sus. | Res. |
| ZYMV | PI414723 | zym-1 | 2 | 3.2-5.7 | 0.00 | 0.00 | na | Sus. | Sus. | Res. |

Table 3 shows exemplary contemplated breeding strategies with certain representative embodiments for production of F1 hybrid elite melon plants comprising agronomic traits pathotype 1 and not display necrosis. ME8094 did not display symptoms upon infection, nor contain ZYMV virus titer, as evidenced by ELISA.

Additionally, ZYMV resistance was found to be closely linked to WMV resistance in ME8094. An F2 population was developed from ME8094 crossed with a susceptible inbred line. The population consisted of 255 individuals that were propagated in the absence of selection. Phenotypes of ZYMV and WMV resistance in F3 progeny derived from this population were determined. A subset of 56 F3 families was fully resistant to ZYMV, consistent with a single, recessive locus. This is a significant advance in that melon has 12 chromosomes and if resistance traits reside on different chromosomes many descendants of a cross will not inherit the resistance alleles. The invention thus provides, in one embodiment, plants with ZYMV resistance closely linked to WMV resistance. This renders it easier to fix such traits by selfing, backcrossing and selection. It is also easier to stack traits in this way. Hence, plants provided by the invention comprising such resistance, including ME8094 and any progeny thereof, can be used as a universal donor line for resistance to ZYMV, WMV, and/or CMV. Advantageously, a plant of the present invention may be characterized by the fact that the ZYMV and WMV traits are linked so closely that the genetic distance between the two loci is less than 6 cM, 5 cM, 4 cM, 3 cM, 2 cM, 1 cM, 0.1 cM, or 0.01 cM, or the genetic distance is essentially equal to 0 cM.

Unexpectedly, the WMV resistance produced according to the invention provided other advantages in addition to linkage to ZYMV resistance. Resistance to WMV from accession PI 414723 (Anagnostou et al., 2003, *J. Euphytica* 116:265-270) did not confer resistance to some isolates of WMV, and therefore cannot serve as a broad source of resistance for this resistance trait. Similarly, it appears from the work by Diaz-Pendon et al. (2005, *Phytopathol.* 95:840-846) that TGR1551 still may carry virus particles, even if it does not show pathological effects relating to WMV, and in work reported here does not appear to display broad spectrum resistance. In contrast to plants comprising such virus resistance traits from PI414723 and TGR1551, it was found that melon plants could be produced such as ME8094 that gave broader spectrum resistance and did not display symptoms upon infection, nor contain WMV virus-titer as evidenced by ELISA. Furthermore, heritability of virus resistances for ZYMV, WMV and CMV from Line ME8094 was shown to be advantageously high. The trait can thus be introgressed in a desired genetic background as described herein. Successful introgression of, for instance, the ZYMV and WMV virus resistance markers from ME8094, accompanied by desirable agronomic traits including fruit length and width, cavity size, firmness, Brix, and rind and flesh color, is described in Example 4 and FIG. 6.

Thus, the viral resistance provided herein represents a significant advance over the art. For instance, resistance to ZYMV is not linked to the unfavourable andromonoecy trait. Also, resistance was demonstrated against all known isolates of ZYMV. Additionally, ZYMV resistance is linked to WMV resistance. This results in increased speed and cost reduction in the development of plants carrying both resistance specificities. Fourth, resistance was conferred, and the presence of the virus was not detectable.

The present inventors now have provided melon plants wherein the sources for resistances to ZYMV and WMV, as well as CMV, have been successfully combined. An example is the inbred line ME8094, which has been demonstrated to have high resistance to CMV (shown by DAS-ELISA by the α-CMV isolate V6; e.g. see FIGS. 3-4), resulting in a mean disease index which is even lower than the index of the 'resistant' line TIGR 1551. With respect to the resistance to ZYMV it has been shown that ME8094 is not affected by infection with ZYMV pathotype 1 (e.g. see FIGS. 2-4), in contrast to all other varieties tested. In a field test with virus field populations of ZYMV, WMV and CMV, no susceptible plants were found in accession ME8094. No other variety is known to harbor a resistance to all these viruses.

The identified resistance displayed a distinct mode of inheritance for each resistance specificity. The resistance to ZYMV was localized on one recessive locus and the resistance to WMV localized on one dominant locus. The resistance to CMV was localized on two additive loci. Additional disease resistance traits may be bred into plant comprising such resistance, including progeny lines of ME8094, particularly given the high heritability of the virus resistance. This includes resistance to CYSDV (Cucurbit Yellow Stunting Disorder Virus; e.g. EP 1800535; EP 1962578), CVYV (Cucurbit Vein Yellowing Virus; e.g. WO 2010/025747), PRSV(Papaya Ring Spot Virus; e.g. Brotman et al., *TAG* 110:337-345, 2005), MNSV (Melon Necrotic Spot Virus; e.g. WO 2003/066900), and/or Powdery Mildew, among others A QTL analysis with respect to the viral resistance loci found that the resistance to WMV and to ZYMV co-located on the same linkage group, while the resistance to CMV was spread over 2 loci in different linkage groups. Hence, the traits could be localized to several specific quantitative trait loci (QTL). Further, it was established that ZYMV resistance is not linked to andromonoecy, which enabled the possibility of obtaining monoecious resistant plants, while the CMV QTL12 resistance trait was not closely linked to the undesirable pentamerous fruit trait.

These experimental data demonstrate that traits of resistance to ZYMV and WMV, and CMV, may be transferred to other melon varieties using melon accession ME8094 as a donor of a specific genetic region or regions, independent of andromonoecy. Thus, in certain embodiments, the present invention provides a melon plant of line ME8094 and seed thereof, and progeny of ME8094 and seed thereof, comprising such ZYMV and WMV resistance as is found in ME8094, as well as associated markers and methods for such marker-assisted breeding.

The skilled person will understand that individually inherited traits are observed in the entire population only after producing a segregating population (e.g. F2), and that fixing traits typically requires backcrossing and selfing.

Based on the above findings, the present inventors were able to develop melon plants comprising the above resistance loci, wherein said loci are not in their natural genetic background.

Producing Multiple-Resistant Melon Varieties

The present inventors have identified certain plant disease resistance traits located, for instance as follows:
1. a locus for CMV resistance on linkage group 12.
2. a locus for CMV resistance on linkage group 2.
3. a locus for WMV resistance on linkage group 11.
4. a locus for ZYMV resistance on linkage group 11.

In one embodiment of a method for producing a multiple-virus-resistant melon variety, one may provide a first inbred melon line with the alleles for CMV (and optionally PM), and a second inbred melon line with the alleles for WMV and ZYMV. Crossing of the two lines results in a hybrid and expression of the recessive alleles can be achieved by selfing, which also results in a successful fixation of the combination of resistance traits. Additional disease resistance traits, for instance conferring resistance to one or more other viruses, such as CYSDV, may also be bred into a ZYMV, WMV, and CMV resistant line.

In additional embodiments, desirable agronomic traits relating to fruit flesh color, Brix level, and length to width ratio, among others, may also be incorporated in progeny lines derived from a plant provided herein and/or by the methods herein described.

Definitive chromosome numbers have not yet been assigned to the melon chromosomes on which several of the resistance-conferring loci are located. However, the chromosomes may be designated by reference to the linkage groups (e.g. LG 12, 2, and 11) on which these and other genomic regions are located. The term linkage group is used herein to refer to a calculated genomic unit based on recombinational genetic mapping, on which the resistance alleles are located, and which has the same hierarchical level as a chromosome. Some traits that have been studied in the public domain were found to be contained in these linkage groups. LG 12, harboring the major locus for CMV resistance, was found to be linked to the traits PM, and pentamerous. Finally LG 11, harboring the loci for both WMV and ZYMV resistance, was found to be linked to the trait Fom-2, but not to andromonoecious. The Fom-2 trait can be used as a marker and thus may also be used to assist in the selection of plants comprising the introgression of interest.

In addition to plants, the invention further provides seeds of the plants of the invention. These seeds are characterized in that they develop into plants of the invention. Said seeds can be obtained after selfing, crossing, or backcrossing the plant of the invention. The invention further provides plants, or plant parts, originating from said seeds. The invention further provides fruit, or fruit parts, originating from the plant originating from said seeds.

The invention further provides a method to transfer the genetic loci associated with resistance to novel melons without conferring deleterious traits such as andromonoecy.

The present invention further provides a method of producing plants of a melon line resistant to ZYMV, WMV, and/or CMV. In one embodiment, the method comprises the steps of;
  a) crossing a plant of a recipient melon breeding line not harboring the desired resistance with a plant of a donor melon breeding line harboring the desired resistance;
  b) collecting the seeds resulting from the cross in step (a),
  c) regenerating the seeds into plants;
  d) providing one or more backcross generations by crossing the plants of step (c) or (optionally selfed) offspring thereof with one or more plants of said recipient melon breeding line to provide backcross plants;
  e) selfing plants of step (d) and growing the selfed seed into plants;
  f) optionally repeating said steps of backcrossing and selfing of steps (d) and/or (e);
  (g) identifying and selecting from the plants grown in step (e) or (f) plants that show the desired resistance.

In one embodiment, the identification and selection of plants in step (g) is performed according to the methods listed below.

Determination of Resistance

Resistant plants can be detected by screening for the presence of virus in plant material. Viruses can be detected by ELISA, using standard methods with commercially available antibodies for the various viruses and molds, such as obtainable from Plant Research International (PRI, Wageningen, the Netherlands), Agdia Inc. (Elkhart, Ind., USA), Neogen Europe Ltd. (Auchincruive, Ayr, Scotland), Monogram Biosciences Inc. (f.k.a. ViroLogic Inc., South San Francisco, Calif., USA). Usually a double antibody sandwich ELISA (DAS-ELISA) protocol is suitable. Alternatively bioassays can be performed for the various diseases.

CMV resistance or susceptibility for instance may be detected by germinating melon seeds and growing the seedlings under standard conditions in a greenhouse on a test table. Susceptible controls may for instance include Vedrantais and PMR5, whereas as resistant controls Freemans cucumber, ME8094, and Virgos may be used. Mock-inoculated plants may be generally included. A day temperature of 20° C. and a night temperature of 18° C. is typically maintained. During periods with low light intensity, seedlings may be grown under artificial light for 16:8 hours day and night, respectively. Maintenance of the correct temperature is important to the success of the assay. Especially high temperatures should be avoided, and during inoculation and during the assay the temperature is generally maintained below 20° C. As an inoculum, susceptible Vedrantais or PMR5 plants with severe mosaic on leaves can be used. Preparation of the inoculum is generally performed on ice in order to maintain virus virulence. Infected leaves are suitably crushed in tap water or in a suitable buffer using a (generally cooled) mortar and pestle and ½ tea spoon carborundum powder per 10 ml of plant suspension. The plants are suitably inoculated 2 or 3 days after transplanting of the seedlings when the first true leaf is observed with full extension of the cotyledons. Between 8 and 10 days after the first inoculation a reinoculation can be performed. The inoculation may entail the rubbing of the inoculation mixture on both cotyledons/first leaf of the plant using a piece of sponge or with the thumb and index finger. Results may be scored 8 days post inoculation (DPI) when plants show adequate symptoms, optionally 12 DPI if desired, and finally 14 DPI. First symptoms of CMV susceptibility are lesions which can be seen on the cotyledons. Furthermore between 6 to 10 days DPI top leaves show clear mosaic and/or chlorosis and plant growth of infected plants will be reduced. It may be desired that at least 90% of the susceptible control plants should be infected for susceptible scores. It may be beneficial that at least 90% of the resistant control plants show no symptoms. Multiple plants can be scored individually, during multiple repeats in multiple environments (geographic regions) to determine the phenotype of given line.

WMV can be detected by germinating melon seeds and growing the seedlings under standard conditions in a greenhouse on a test table. Susceptible controls may for instance include Vedrantais and PMR5, whereas as resistant controls TGR 1551, ME8094 and PI124112 may be used. Seedlings are generally grown at 22° C./20° C. day/night. Assay conditions include a temperature of 25° C. day and night. During periods with low light intensity, seedlings are generally under artificial light 16:8 hours day and night, respectively. Susceptible plants with severe mosaic on leaves can be used for inoculation. Preparation of the inoculum is generally performed on ice in order to maintain virus virulence. Infected leaves are suitably crushed in tap water or in a suitable buffer using a (generally cooled) mortar and pestle and ½ tea spoon carborundum powder per 10 ml of plant suspension. The plants are suitably inoculated 2 or 3 days after transplanting of the seedlings when the first true leaf is observed with full extension of the cotyledons. Between 8 and 10 days after the first inoculation a reinoculation can be performed. The inoculation may entail the rubbing of the inoculation mixture on both cotyledons/first leaf of the plant using a piece of sponge or with the thumb and index finger. Results may be scored 7 to 10 DPI when plants show adequate symptoms. A second observation may be performed 3 days after first monitoring and a third observation 14 DPI. Symptoms include a severe green mosaic on the leaves.

ZYMV for instance may be detected by germinating melon seeds and growing the seedlings under standard conditions in a greenhouse on a test table. Susceptible controls may for instance include Vedrantais and PMR5, whereas PI414723, ME8094, and PI175109 may be used as resistant controls. Seedlings are generally grown at 22° C./20° C. day/night. Assay conditions include a temperature of 25° C. day and night. During periods with low light intensity, seedlings are generally under artificial light 16:8 hours day and night, respectively. Susceptible plants with severe mosaic on leaves can be used for inoculation. Infected leaves are crushed in tap water or with the standard buffer using a cooled mortar and pestle. The plants may be dusted with a layer of carborundum or ½ tea spoon of carborundum powder may be added to every 10 ml of inoculum suspension. Preparation of inoculum generally takes place on ice in order to maintain virus virulence. Plant stage of first inoculation is suitably 2 or 3 days after transplanting of the seedlings when first true leaf can be seen and cotyledons have fully grown. Plant stage of reinoculation is suitably after 7 to 10 days and the 1st true leaf can be inoculated. Thereto, the inoculation mixture may be rubbed on both cotyledons/first leaf of the plant using a sponge. First observation is 7 DPI when plants show adequate symptoms; second observation is 12 DPI, if desired. The third observation is 14 DPI. First symptoms of ZYMV between 6 to 10 days DPI on top leaves show clear yellow mosaic, dark green mottling or even necrosis of the leaf and the plant growth of infected plants will be reduced. At least 90% of the susceptible control plants should be infected. At least 90% of the resistant control plants should not show symptoms.

Production of Resistant Melon Plants

A first step in the production of virus resistant melons often comprises crossing a plant of a melon line in which the virus resistance trait is present in the parent 1 ($P_1$) or an offspring plant thereof having all disease resistance characteristics, and using a plant of a melon breeding line to which the resistance traits are to be introgressed as parent 2 ($P_2$). Generally an inbred line $P_1$ is the donor parent, and $P_2$ is the recipient parent. Said crossing will result in an $F_1$ progeny or offspring population containing two sets of homologous chromosomes obtained from both parents. This first step will result in a hybrid $F_1$ population.

It is not necessary to perform a genotypic or phenotypic analysis of the progeny of this first cross in which inbreds are crossed, as all plants of the $F_1$ population have the same genotype. The resulting plant population (representing the $F_1$ hybrids) may be selfed to produce $F_2$ seeds, but may be backcrossed to produce a $BC_1$ population using a plant of line parent $P_2$ as the recurrent parent. The $BC_1$ seeds or $F_2$ seeds or the plants grown therefrom may then be screened for having the resistance trait by performing resistance bioassays as described herein. In such a segregating $BC_1$ or $F_2$, this phenotypic analysis can assist in selecting those plants that are most suited for use in further breeding. In order to avoid the necessity to await the results of a phenotypic analysis of the $BC_1$ or $F_2$, the presence of a QTL associated with the resistance of interest can suitably be established and screened using a marker linked thereto in order to follow the trait by marker assisted breeding (MAB) or marker assisted selection (MAS) methods. Such a genotypic screening for the presence of the resistance trait may greatly speed up the breeding process. If desired, the $BC_1$ or $F_2$ seeds or further progeny seed obtained by the methods of the invention, or the plants grown therefrom may be screened for the presence of the trait by both genotypic and phenotypic methods as described herein.

The transfer of the genetic loci for resistance can be brought about by crossing. During plant crossing, various introgressions will generally be observed. Alternatively, the transfer may be brought about by genetic engineering. Both methods result in a recombinant plant, wherein DNA that is originally present at a specific location within the chromosome is exchanged for DNA from another plant (i.e. maternal for paternal or vice versa).

To obtain the genetic loci in a desired background, the segment on the specific linkage group(s) associated with the resistance may be introgressed into the genome of a plant of a melon breeding line, by one or more steps of crossing and backcrossing as described above and selecting from the progeny those plants that exhibit agronomically desirable characteristics, such as, but not limited to, insect resistance, valuable fruit characteristics including Brix level, flesh color, fruit shape, yield, etc., in combination with the traits of ZYMV, WMV, and CMV resistance, and for instance optionally PM resistance. This will result in a situation wherein the resistance allele is no longer in its natural genetic background, but is introgressed in the genetic background of the melon line of interest.

In another aspect of the invention an elite line is produced by consecutive steps of backcrossing to the recurrent parent in order to make the line an increasingly pure elite and inbred (inbred line). Alternatively, or in combination, the double haploid technique is applied. Thus, the present invention also provides methods for producing elite lines having resistance to ZYMV, WMV, and/or CMV. The elite lines may be produced by the methods of the invention to comprise one or more introgression(s) conferring the desired virus resistance. One example of an introgression involves introgression of a QTL found in melon accession ME8094.

Optionally, the above described melon plants can be selfed to provide inbred lines essentially homozygous for the alleles conferring resistance. Alternatively, or in combination, the double haploid technique is applied.

The optionally inbred or double haploid, melon plants obtained by the above described methods of backcrossing and optional selfing and/or DH production, can further be used to produce hybrids, by crossing with plants of other, optionally inbred, melon lines or other elite melon lines. The invention thus further provides a method of producing hybrids by crossing a melon plant obtained by a method of the invention with a plant of a melon inbred or elite line. These hybrids can be homozygous or heterozygous for the alleles conferring ZYMV, WMV, and/or CMV resistance. The hybrid may be homozygous for the alleles conferring ZYMV, WMV, and/or CMV resistance as expression of the phenotype is then optimal. However, in the case of dominant resistance traits, homozygosity for the allele is not required.

The invention further pertains to the plants, or part of the plants, obtained by a method of the invention. Contemplated part(s) of plants may be selected from the group consisting of: a fruit, a leaf, a root, a stem, pollen, an ovule, a cell, and a seed.

These plants of the invention can be characterized in that they display ZYMV and WMV resistance, may further comprise CMV resistance, and may comprise at least one further agronomic trait selected from: desired flesh color (e.g. orange, green, or white), ≥9.5° Bx, a length (i.e. distance from peduncle to blossom end of fruit; proximal to distal) to width ratio of less than about two to one (i.e. width to length ratio of ≥0.5), such as a length to width ratio of about one to one, and resistance to Powdery Mildew (PM) caused by *Podosphaera xanthii*. These plants can be selected from the $F_1$ or $F_2$ progeny, or from the steps of backcrossing and/or selfing the $F_1$ or $F_2$ progeny or from any subsequent selfing or backcross steps. Also comprised in the invention are the seeds of the above-mentioned plants. The invention further comprises the fruits, or part of fruits, of above-mentioned plants.

The invention further pertains to the melon lines and melon inbred lines obtained by the method of the invention, via multiple steps typical of plant breeding, including, but not limited to, an initial cross of two melon plants, at least one of which contains favorable alleles for the virus resistances described herein, recurrently selecting and self-pollinating plants in sequential generations (e.g. F1, F2, F3, . . . , Fn) after the cross, or backcrossing the F1, F2, backcross 1 ("BC1"), BC2, BC3, BC4, . . . BCn progeny to the recurrent parent, and optional selfing to produce homozygous lines. Alternatively, or in combination, the double haploid technique may be applied.

The invention further pertains to the hybrids, obtained by crossing the melon inbred lines of the invention with different melon inbred lines or elite lines. Also comprised in the invention are seeds of said hybrids.

The establishment of the proper introgression in offspring plants of the invention may be monitored at several steps (of the above mentioned method) by screening the genome of the plants for the presence of the resistance alleles defined herein. The population can be screened in a number of different ways. For instance, the population can be screened using a resistance assay as described above. Such assays are known in the art. Alternatively marker assisted selection can be used.

In embodiments of methods for detecting the presence of a marker in a melon plant, the method may also comprise the steps of providing an oligonucleotide or polynucleotide capable of hybridizing under stringent hybridization conditions to a nucleic acid sequence associated with said allele, or of a marker linked to said allele, contacting said oligonucleotide or polynucleotide with optionally digested genomic nucleic acid of a melon plant, and determining the presence of specific hybridization of said oligonucleotide or polynucleotide to said genomic nucleic acid. The method may also comprise RFLP analysis and/or DNA sequencing.

The method may be performed on a nucleic acid sample obtained from said melon plant, although in situ hybridization methods may also be employed. Alternatively, and in a further embodiment, the skilled person may, once the nucleotide sequence of the allele has been determined, design specific hybridization probes or oligonucleotides capable of hybridizing under stringent hybridization conditions to the nucleic acid sequence of said allele and may use such hybridization probes in methods for detecting the presence of an allele of the invention in a melon plant.

The present invention further relates to a melon seed designated ME8094, a sample of said seed having been deposited with the NCIMB, Aberdeen, Scotland under depositors reference ME8094 and NCIMB accession number 41653 and, a melon plant, or parts thereof, produced by growing said seed, and to pollen and ovules of the plant thus grown. The invention relates to a melon plant, or parts thereof, having all of the physiological and morphological characteristics of the melon plant grown from the deposited seed, to a tissue culture, such as a culture of cells of protoplasts from a tissue selected from the group consisting of leaves, pollen, embryos, roots, root tips, anthers, flowers, fruit, and seeds of regenerable cells, of a melon plant of line ME8094, wherein the tissue regenerates plants capable of expressing all the morphological and physiological characteristics of line ME8094. The invention further relates to a melon plant regenerated from said tissue culture, capable of expressing all the morphological and physiological characteristics of line ME8094.

The present invention further relates to a method for producing a hybrid melon seed comprising crossing a first inbred parent melon plant with a second inbred parent melon plant, or with another, different melon plant, and harvesting the resultant hybrid melon seed, wherein said first or second parent melon plant is the melon plant grown from the deposited seed. The present invention further relates to a hybrid melon seed produced by this method, to a hybrid melon plant, or parts thereof, subsequently produced by growing the hybrid melon seed as produced by the method, as well as melon seed subsequently produced by growing said hybrid melon plant and to a melon plant, or parts thereof, subsequently produced from said seed.

The present invention further relates to a method for producing a ME8094-derived melon plant, comprising: a) crossing a plant of line ME8094, a sample of said seed having been deposited with the NCIMB, Aberdeen, Scotland under accession number NCIMB 41653 and depositors reference ME8094, with a second melon plant to yield progeny melon seed; b) growing said progeny melon seed, under plant growth conditions, to yield said ME8094-derived melon plant. This method may optionally further comprise the step of: c) crossing said ME8094-derived melon plant with itself or another melon plant to yield additional ME8094-derived progeny melon seed; d) growing said progeny melon seed of step (c) under plant growth conditions, to yield additional ME8094-derived melon plants; e) repeating the crossing and growing steps of (c) and (d) from 0 to 7 times to generate further ME8094-derived melon plants.

The invention also pertains to a melon plant, or parts thereof, as disclosed herein, wherein the plant or parts thereof have been transformed so that its genetic material contains one or more transgenes operably linked to one or more regulatory elements.

Definitions

The term "melon" as used herein refers to plants of the gourd family that carry large and often round fruit having pulpy flesh and many seeds that are embedded within the flesh or fill the center of the fruit, belonging to different species in the family of Cucurbitaceae such as *Cucumis melo* L. (muskmelon), *Cucumis sativus* (cucumber), and *Citrullus lanatus* (watermelon). When reference is made to "melon" as used herein, plants of these melon species are referred to. The term includes reference to *Cucumis melo* L.

*Cucumis melo* L. (*C. melo*) includes both wild accessions as well as a large number of cultivars and is generally sub-divided into the subspecies *agrestis* and *melo*. The latter is then further sub-divided in the botanical varieties *cantalupensis, chito, conomon, flexuosus, inodorus, momordica, reticulatus* and *texanus*. It is believed that melon accession ME8094, represents an oriental pickling melon.

The term "*Cucumis melo* plant" as used herein refers to a plant of any variety of muskmelon as defined above. In certain embodiments, the term refers to muskmelon plants of the varieties *Cucumis melo* var. *cantalupensis, Cucumis melo* var. *conomon, Cucumis melo* var. *reticulatus* and *Cucumis melo* var. *inodorus*, such as for instance the cultivars or commercial types 'Amarillo Oro', 'Sharlyn,' 'Cantaloupe', 'Casaba', 'Crenshaw', 'Earl's' (Japanese Melon), 'Galia', 'Honeyball', 'Honeydew', 'Jenny Lind', 'Ogen', 'Piel de Sapo', green flesh 'Rocky Ford', 'Santa Claus', 'Tendral', Easter and Western Shipper, and 'Yellow Canary'.

The term "family" indicates a taxonomic level below that of the order (i.e. the family Cucurbitaceae).

The term "firmness" indicates the force (kgf) needed to penetrate the rind using a digital handheld penetrometer.

The term "genus" indicates a taxonomic level below that of the family (i.e. the genus *Cucumis* or *Citrullus*).

The term "species" indicates a taxonomic level below that of the genus (e.g. *Cucumis melo* (muskmelon) or *Citrullus lanatus* (watermelon)).

The term "subspecies" indicates a taxonomic level below that of the species (e.g. *Cucumis melo* subsp. *melo*, or *Citrullus lanatus* subsp. *vulgaris* (watermelon)).

The term "variety", indicates a varietas and its abbreviation "var.", and refers to a botanical variety (a taxonomic level below that of the species or subspecies). As used herein, the term "variety" specifically is not equivalent with the term variety as defined in the UPOV treaty (the UPOV variety is herein equivalent to 'accession'). Within the species of *Cucumis melo*, the term "Group" is often used when referring to the different varieties, and these terms are in this context equivalent and interchangeable. The following varieties are generally recognized in *C. melo*: The chito group (mango melon); the conomon group (*Cucumis melo* var. *conomon*; oriental pickling melon); the flexuosus group (Armenian cucumber); the inodorus group (*Cucumis melo* var. *inodorus*; casaba melon or honeydew); the reticulatus group (*Cucumis melo* var. *reticulatus*; synonyms: netted melon, nutmeg melon, American cantaloupe, false cantaloupe); and the cantalupensis Group (*Cucumis melo* var. *cantalupensis*; synonym: true cantaloupe or European cantaloupe).

The term "accession" denotes (a plant representing) the lowest taxonomical rank and thus it is equivalent to the term 'variety' as defined in the UPOV treaty and according to Rule 26(4) of the European Patent Convention. The term "cultivar" denotes a cultivated accession and is used herein to denote a plant having a biological status other than a "wild" status, which wild status indicates the original non-cultivated, or natural state of a plant or accession. The term "cultivar" includes, but is not limited to, semi-natural, semi-wild, weedy, traditional cultivar, landrace, breeding material, research material, breeder's line, synthetic population, hybrid, founder stock/base population, inbred line (parent of hybrid cultivar), segregating population, mutant/genetic stock, market class and advanced/improved cultivar. Examples of cultivars include such cultivated accessions as Charentais, Italian cantaloupe (from the cantalupensis Group); Galia, Ananas (from the reticulatus Group); Amarillo, Branco, Crenshaw, Honeydew Negro, Piel de Sapo, Rochet, Tendral, (from the conomon Group) oriental pickling melon, and Yellow Canary (from the inodorus Group).

The term "Brix" ("° Bx") is used here to quantify the mass ratio of dissolved solids, such as sucrose, to water in a liquid. More specifically, a measurement of the Brix level of a melon fruit may be made according to methods well known in the art, for instance by use of a saccharimeter or refractometer. For instance, a measurement of 10° Bx corresponds to 10 grams of dissolved solids including sucrose per 100 grams of liquid.

The term "donor" is used to indicate the source of the hereditary material that confers resistance as defined herein. For instance, the ZYMV, WMV, and CMV resistance traits discussed in the present application originate from a donor melon plant designated as ME8094 (accession NCIMB 41653) or progeny thereof.

The term "crossing" as used herein refers to the fertilization of female plants (or gametes) by male plants (or gametes). The term "gamete" refers to the reproductive cell (egg or sperm) produced in plants by meiosis from a gametophyte and involved in sexual reproduction, during which two gametes of opposite sex fuse to form a zygote. The term generally includes reference to a pollen (including the sperm cell) and an ovule (including the ovum). Crossing therefore generally refers to the fertilization of ovules of one individual with pollen from another individual, whereas "selfing" refers to the fertilization of ovules of an individual with pollen from the same individual. Crossing is widely used in plant breeding and results in a mix of genomic information between the two plants equivalent to receiving homologous chromosomes from both the mother and the father. This will result in a new variety. Selfing of a homozygous plant will result in a genetically similar plant since there is no new genetic variation introduced.

When referring to crossing in the context of achieving the introgression of a genomic region or segment, the skilled person will understand that in order to achieve the introgression of only a part of a chromosome of one plant into the chromosome of another plant, it is required that random portions of the genomes of both parental lines will be recombined during the cross due to the occurrence of crossing-over events in the production of the gametes in the parent lines. Therefore, the genomes of both parents must be combined in a single cell by a cross, where after the production of gametes from said cell and their fusion in fertilization will result in an introgression event.

As used herein, the terms "introgressing", "introgress" and "introgressed" refer to both a natural and artificial process whereby individual genes, chromosomal segments, or entire chromosomes are moved from one individual, species, variety or cultivar into the genome of another individual, species, variety or cultivar, by crossing those individuals, species, varieties or cultivars. In plant breeding, the process usually involves selfing or backcrossing to the recurrent parent to provide for an increasingly homozygous plant having essentially the characteristics of the recurrent parent in addition to the introgressed gene or trait.

The term "introgression" refers to the result of an introgression event.

The term "backcross" refers to the process wherein the plant resulting from a cross between two parental lines is repeatedly crossed with one of its parental lines, wherein the parental line used in the backcross is referred to as the recurrent parent. Repeated backcrossing results in replacement of genome fragments of the donor parent with those of the recurrent. Backcrossing methods can be used with the present invention to improve or introduce a characteristic into the inbred. The parental melon plant which contributes the gene for the desired characteristic is termed the nonrecurrent or donor parent. This terminology refers to the fact that the nonrecurrent parent is used one time in the backcross protocol and therefore does not recur. The parental plant to which the gene or genes from the nonrecurrent parent are transferred is known as the recurrent parent as it is used for several rounds in the backcrossing protocol. In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

The term "selfing" refers to the process of self-fertilization wherein an individual is pollinated or fertilized with its own pollen. Repeated selfing eventually results in homozygous offspring.

As used herein, the term "homozygous" means a genetic condition existing when identical alleles reside at corresponding loci on homologous chromosomes.

As used herein, the term "heterozygous" means a genetic condition existing when different alleles reside at corresponding loci on homologous chromosomes.

The term "recombination" or "to recombine" refers to the exchange of information between two homologous chromosomes during meiosis. In a "recombinant" plant, DNA that is originally present at a specific location within the chromosome, e.g. linked to a gene/locus, is exchanged for DNA from another plant (i.e. maternal for paternal or vice versa). In order to exchange only the required material, and maintain the valuable original information on the chromosome as much as possible, two flanking crossover or recombination events will usually be required. In a double recombinant this exchange has taken place on both sides of a gene/locus. One way to find such a double recombinant, is to screen a population of F2-plants. This population has to be large, since double recombination occurs with limited frequency. Alternatively, double recombinants can be the result of subsequent backcrossing. The frequency of double recombination is the product of the frequencies of the single recombinants (e.g. a recombinant in a 10 cM area can be found with a frequency of 10%, double recombinants are found with a frequency of 10%×10%=1%).

As used herein, the term "progeny" means (a) genetic descendant(s) or offspring.

As used herein, the term "population" means a genetically heterogeneous collection of plants derived from a shared, common genitor.

A "recombination event" refers to a mitotic or meiotic crossing-over event, as well as a transgenic event.

As used herein, the color of the flesh of a melon fruit may be defined by comparison with a reference color chart, such as the RHS color chart, as is known in the art. In certain embodiments the flesh color may be termed "orange" and defined as corresponding to 9A-35B or 40A-44C as denoted by the RHS color chart.

As used herein, the term "hybrid" means any offspring of a cross between two genetically unlike individuals, more generally the term refers to the cross between two (elite or inbred) breeding lines which will reproduce true to the parent from seed.

The term "breeding line", as used herein, refers to a line of a cultivated melon having commercially valuable or agronomically desirable characteristics, as opposed to wild varieties or landraces that are the result of natural selection. The term includes reference to an elite breeding line or elite line, which represents an essentially homozygous, usually backcrossed and inbred, line of plants used to produce (commercial) $F_1$ hybrid seeds. Agronomically desirable characteristics include, but are not limited, to disease resistance, insect resistance, valuable fruit characteristics, yield, etc. A breeding line is typically an inbred line, and may be an elite line.

As used herein, the term "pure inbred" or "inbred" refers to a substantially homozygous plant or plant line obtained by repeated selfings.

As used herein, the term "allele(s)" means any of one or more alternative forms of a locus or gene, all of which alleles relate to at least one trait or characteristic. In a diploid cell or organism, the two copies of a gene occupy corresponding loci on a pair of homologous chromosomes. Each copy may be a distinct allele.

A "gene" is defined herein as a hereditary unit (often indicated by a sequence of DNA) that occupies a specific location on a chromosome and that contains the genetic instruction for a contribution to potential phenotypic characteristics or trait in a plant.

A "locus" is defined herein as the position that a given gene occupies on a chromosome of a given plant species.

Similar to the genetic unit "gene", on which the phenotypic expression depends on a large number of factors that cannot be predicted, the genetic unit "QTL" denotes a region of the genome that is related to a phenotypically quantifiable trait.

The term "natural genetic background" is used herein to indicate the original genetic background of an allele or QTL. Conversely, a method that involves the transfer of DNA comprising the allele or QTL, or a part thereof that confers the specific characteristic resident in the allele or QTL, to the same position on the corresponding chromosome of another melon line or variety, will result in that allele or QTL, or said part thereof, not being in its natural genetic background.

As used herein, the term "linkage group" refers to all of the genes or genetic traits that are located on the same chromosome. Within the linkage group, those loci that are close enough together will exhibit linkage in genetic crosses. Since the probability of crossover increases with the physical distance between genes on a chromosome, genes whose locations are far removed from each other within a linkage group may not exhibit any detectable direct linkage in genetic tests. The genes are 'indirectly linked', via intermediately positioned loci. The term "linkage group" is mostly used to refer to genetic loci that exhibit linked behavior in genetic systems where chromosomal assignments have not yet been made. Thus, in the present context, the term "linkage group" is synonymous to (the physical entity of) a chromosome.

As used herein, the terms "molecular genomic marker," "molecular marker" or "marker" refer to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion/deletion (INDEL) mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. DNA sequencing may also be employed to determine the allele present at a given marker of interest. Molecular genomic markers are used in the well known processes of MAB (marker assisted backcrossing) and MAS (marker assisted selection), wherein the speed and efficiency of the breeding process can be greatly enhanced using technical information on the position of the gene or allele of interest.

The term "transformed" is used herein as a synonym for the transfer of isolated and cloned genes into the DNA, usually the chromosomal DNA or genome, of another organism by genetic engineering techniques, usually by the aid of a vector or other genetic transformation system.

The terms "resistant" and "resistance" encompass both partial and full resistance to infection. A pathogen susceptible melon plant may either be non-resistant or have low levels of resistance to infection by the pathogen. Resistance also includes a symptomless-carrier, but generally relates to the absence, or at least a low titer, of virus particles in the plant, as for instance observable with antibodies, upon infection. In certain embodiments, plants of the invention exhibit resistance to the diseases essentially as exhibited by accession ME8094 as well as one or more other parental lines in their pedigree(s).

The term "pathogen-susceptible recipient melon plant" is used herein to indicate a melon plant that is to receive DNA obtained from a donor melon plant that comprises the pathogen-resistance allele. Said pathogen-susceptible recipient melon plant may or may not already comprise one or more alleles for (the same or other) resistance, in which case the term indicates a plant that is to receive an additional resistance allele.

As used herein, the term "plant part" indicates a part of the melon plant, including organelles, single cells and cell tissues, such as plant cells that are intact in plants, cell clumps and tissue cultures from which melon plants can be regenerated. Examples of plant parts include, but are not limited to, single cells, protoplasts, and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like.

As used herein, the term "Zucchini yellow mosaic virus" abbreviated as "ZYMV" refers to an aphid-borne potyvirus that affects all cucurbits including pumpkins, squashes, vegetable marrows, courgettes, melons, watermelons, cucumbers, gherkins and various gourds. The effects are severe leaf mosaic, yellowing and eventually "shoestring" symptoms in the leaves. The fruits are stunted, twisted and deformed by raised protuberances, which make them unmarketable. In cultivated crops plants cease producing marketable fruits within 1-2 weeks of infection and serious financial losses can occur.

As used herein, the term "Watermelon mosaic virus" abbreviated as "WMV" (formerly known as "WMV-2") is also an aphid-transmitted potyvirus that can infect and produce symptoms on all commercially grown cucurbits. This causes milder symptoms on the foliage of most infected plants like squash, and growers have seen a lessening of foliar symptoms following fertilization. Fruit distortion and color breaking are still a problem on varieties like yellow straight-neck squash. The host range for WMV-2 is not limited to cucurbits, thus opening the possible overwintering of this virus in several leguminous species such as clover. Mixed infections of cucurbits with CMV and WMV-2 are common by the end of the season.

As used herein, the term "Papaya Ringspot Virus" abbreviated as "PRSV" (formerly known as "WMV-1") is aphid transmitted, and infection is limited to cucurbits. This virus is capable of infecting all commercial cucurbit crops. The foliage of affected plants shows strong mosaic, distortion, and deep leaf serration. Fruits are also malformed with knobby overgrowth.

As used herein, the term "Cucumber mosaic virus" abbreviated as "CMV" is a plant pathogenic virus in the family Bromoviridae. It is the type member of the plant virus genus, *Cucumovirus*. This virus has a worldwide distribution and a very wide host range. In fact it has among the widest host range of any known plant virus (191 hosts in 40 families). It can be transmitted from plant to plant both mechanically by sap and by aphids in a stylet-borne fashion. It can also be transmitted in seeds and by the parasitic weeds, Cuscuta sp. (dodder). Since CMV was first recognized it has been found to infect a great variety of other plants, including other vegetables such as squash, melons, peppers, beans, tomatoes, carrots, celery, lettuce, spinach and beets, various weeds and many ornamentals and bedding plants. Symptoms seen with this virus include leaf mosaic or mottling, yellowing, ringspots, stunting, and leaf, flower and fruit distortion.

DEPOSIT INFORMATION

A deposit of *C. melo* line ME8094 which is disclosed herein above and referenced in the claims, was made with NCIMB, Ferguson Building, Craibstone Estate, Bucksburn, Aberdeen, AB21 9YA, Scotland, U.K. The date of deposit was Sep. 4, 2009 and the accession number for those deposited seeds of melon line ME8094 is NCIMB Accession No. 41653. All restrictions upon the deposit have been removed, and the deposit is intended to meet all of the requirements of 37 C.F.R. § 1.801-1.809. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

EXAMPLES

Example 1: Genetic Markers of *C. melo* Linkage Groups 02, 11, and 12

Figure 1:
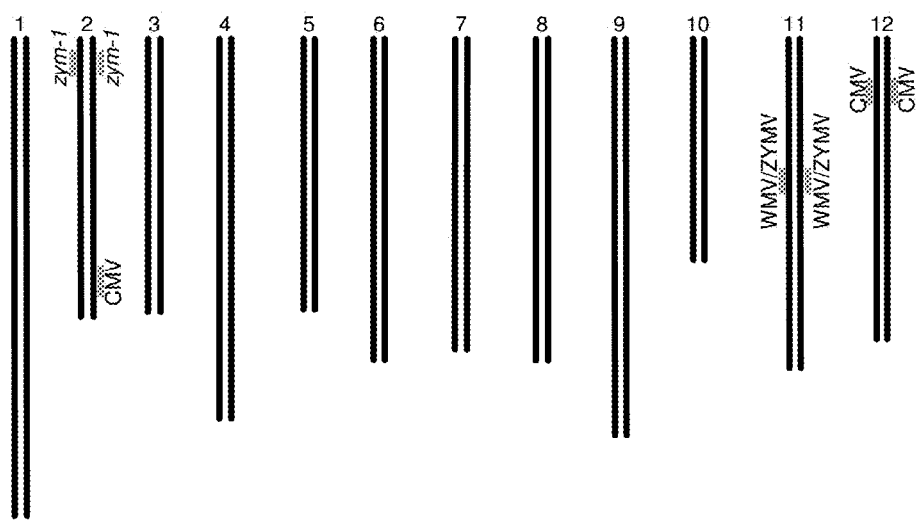

A consensus genetic map was developed for *C. melo* comprising genetic markers on chromosomes (i.e. "linkage groups") 1-12. A melon genetic map is diagrammed in FIG. 1 and markers are listed in Table 4 for chromosomes 02, 11, and 12 including those found to be linked to trait(s) conferring resistance to WMV, ZYMV, and CMV.

TABLE 4

Genetic markers on melon chromosomes linked to virus resistance traits of interest.

| Marker name | Chromosome | Map position (cM) |
|---|---|---|
| NU0218625 | 2 | 0 |
| NU0243780 | 2 | 0 |
| NU0218305 | 2 | 2.005023473 |
| NU0220431 | 2 | 2.260671264 |
| NU0218248 | 2 | 3.242407591 |
| CMBR041 | 2 | 3.264408637 |
| NU0218808 | 2 | 3.403622419 |
| NU0218497 | 2 | 3.887811556 |
| NU0218113 | 2 | 3.965525472 |
| NU0244013 | 2 | 4.04473782 |
| NU0244734 | 2 | 4.06540191 |
| NU0220855 | 2 | 4.097716126 |
| NU0244741 | 2 | 4.097716126 |
| NU0220997 | 2 | 4.262198996 |
| NU0220034 | 2 | 5.70260578 |
| NU0220178 | 2 | 5.739450718 |
| NU0218179 | 2 | 5.739450718 |

TABLE 4-continued

Genetic markers on melon chromosomes linked to virus resistance traits of interest.

| Marker name | Chromosome | Map position (cM) |
|---|---|---|
| NU0243740 | 2 | 5.739450718 |
| NU0218531 | 2 | 5.739450718 |
| NU0244228 | 2 | 6.439646176 |
| NU0219402 | 2 | 8.005689695 |
| NU0220130 | 2 | 8.201296581 |
| NU0219191 | 2 | 8.46671327 |
| NU0219483 | 2 | 8.46671327 |
| NU0220928 | 2 | 8.46671327 |
| NU0218758 | 2 | 8.870936634 |
| NU0243353 | 2 | 10.31160741 |
| NU0220646 | 2 | 10.4013544 |
| NU0220793 | 2 | 10.87913017 |
| NU0243722 | 2 | 10.87913017 |
| NU0220647 | 2 | 11.5186551 |
| NU0243479 | 2 | 13.54962773 |
| NU0218211 | 2 | 17.53850024 |
| NU0244702 | 2 | 19.26707387 |
| NU0244778 | 2 | 19.28565793 |
| NU0218156 | 2 | 22.52068613 |
| NU0219009 | 2 | 23.73349775 |
| NU0244019 | 2 | 23.90571157 |
| NU0219243 | 2 | 26.46334624 |
| NU0244631 | 2 | 26.50123545 |
| NU0218641 | 2 | 27.31597847 |
| NU0219769 | 2 | 27.31597847 |
| NU0220607 | 2 | 27.31597847 |
| NU0221028 | 2 | 27.31597847 |
| NU0244521 | 2 | 27.31597847 |
| NU0244557 | 2 | 27.35742402 |
| NU0218847 | 2 | 27.4327107 |
| NU0219284 | 2 | 29.07702559 |
| NU0220497 | 2 | 31.36395523 |
| NU0220373 | 2 | 33.319037 |
| NU0220671 | 2 | 33.319037 |
| NU0221012 | 2 | 33.319037 |
| NU0218600 | 2 | 35.34813167 |
| NU0219157 | 2 | 36.05158803 |
| NU0218325 | 2 | 37.00118133 |
| NU0220688 | 2 | 37.00118133 |
| NU0220575 | 2 | 37.00118133 |
| NU0218570 | 2 | 40.44668981 |
| NU0219353 | 2 | 40.44668981 |
| NU0218794 | 2 | 42.79509072 |
| NU0218957 | 2 | 44.3589836 |
| NU0243402 | 2 | 44.3589836 |
| NU0220299 | 2 | 44.59619893 |
| NU0219474 | 2 | 45.97152125 |
| NU0243330 | 2 | 46.16907705 |
| NU0243691 | 2 | 46.16907705 |
| NU0219497 | 2 | 47.67357163 |
| NU0220778 | 2 | 47.67357163 |
| NU0220341 | 2 | 48.78886347 |
| NU0220623 | 2 | 48.78886347 |
| NU0243559 | 2 | 48.78886347 |
| NU0243262 | 2 | 48.80075654 |
| NU0244117 | 2 | 49.69564747 |
| NU0243516 | 2 | 49.72408802 |
| NU0244258 | 2 | 49.72408802 |
| NU0218783 | 2 | 50.08465281 |
| NU0220057 | 2 | 50.15524031 |
| NU0220378 | 2 | 50.24974769 |
| NU0221022 | 2 | 51.7153129 |
| NU0243544 | 2 | 51.7153129 |
| NU0218553 | 2 | 52.34831859 |
| NU0219511 | 2 | 52.59656731 |
| NU0220230 | 2 | 52.81618911 |
| NU0220799 | 2 | 52.85478221 |
| NU0218033 | 2 | 53.16910559 |
| NU0218250 | 2 | 53.16910559 |
| NU0219019 | 2 | 53.16910559 |
| NU0219150 | 2 | 53.16910559 |
| NU0220902 | 2 | 53.16910559 |
| NU0218440 | 2 | 53.98983146 |
| NU0219260 | 2 | 53.98983146 |
| NU0243343 | 2 | 55.46780895 |
| NU0244057 | 2 | 56.41141875 |
| NU0218263 | 2 | 56.68725237 |
| NU0219294 | 2 | 56.91002694 |
| NU0218782 | 2 | 57.07230164 |
| NU0219961 | 2 | 57.07230164 |
| NU0218391 | 2 | 57.09555749 |
| NU0219210 | 2 | 57.09555749 |
| NU0219737 | 2 | 57.09555749 |
| NU0220030 | 2 | 57.09555749 |
| NU0243709 | 2 | 57.09555749 |
| NU0220988 | 2 | 57.09555749 |
| NU0219065 | 2 | 57.24368788 |
| NU0243918 | 2 | 57.24368788 |
| SE0341 | 2 | 61.42827898 |
| NU0218418 | 2 | 63.59125892 |
| NU0218939 | 2 | 63.59125892 |
| NU0219989 | 2 | 63.67652446 |
| NU0219146 | 2 | 63.8882434 |
| NU0220101 | 2 | 64.07617266 |
| NU0219616 | 2 | 64.55779844 |
| NU0218061 | 2 | 65.36267604 |
| NU0220948 | 2 | 65.64163136 |
| NU0220052 | 2 | 66.48327011 |
| NU0218189 | 2 | 68.87889185 |
| NU0218383 | 2 | 69.69643795 |
| NU0218546 | 2 | 70.10661241 |
| NU0218893 | 2 | 70.10661241 |
| NU0218721 | 2 | 77.54261021 |
| NU0220876 | 2 | 77.54261021 |
| NU0243799 | 2 | 77.54261021 |
| NU0218174 | 2 | 77.54479389 |
| NU0220375 | 2 | 77.54479389 |
| NU0219901 | 2 | 79.08012076 |
| NU0220356 | 2 | 79.08012076 |
| NU0220970 | 2 | 79.08012076 |
| NU0221047 | 2 | 79.08012076 |
| NU0243606 | 2 | 79.08012076 |
| NU0244619 | 2 | 79.08012076 |
| NU0218669 | 2 | 79.69358302 |
| NU0218746 | 2 | 79.69358302 |
| NU0219744 | 2 | 79.69358302 |
| NU0220859 | 2 | 79.69358302 |
| NU0220476 | 2 | 80.09862541 |
| NU0220355 | 2 | 80.18444824 |
| NU0218140 | 2 | 80.69070778 |
| NU0243345 | 2 | 80.69070778 |
| NU0243772 | 2 | 80.69070778 |
| NU0219030 | 2 | 80.69070778 |
| NU0243554 | 2 | 80.69070778 |
| NU0219481 | 2 | 80.76165418 |
| NU0220783 | 2 | 80.76165418 |
| NU0218199 | 2 | 80.76165418 |
| NU0218904 | 2 | 81.51930238 |
| NU0218979 | 2 | 81.52021354 |
| NU0218220 | 2 | 81.91470526 |
| NU0220314 | 2 | 83.53806571 |
| NU0243560 | 2 | 83.53806571 |
| NU0220810 | 2 | 86.05056343 |
| NU0220771 | 2 | 86.32269617 |
| NU0220659 | 2 | 86.32269617 |
| NU0219017 | 2 | 87.37190381 |
| NU0243573 | 2 | 89.62806106 |
| NU0218877 | 2 | 89.92424416 |
| NU0220936 | 2 | 89.92782739 |
| NU0218353 | 2 | 90.01309293 |
| NU0218717 | 2 | 90.20317144 |
| NU0219021 | 2 | 92.19321242 |
| SE0343299 | 2 | 92.92763465 |
| NU0220226 | 2 | 92.92763465 |
| NU0218628 | 2 | 95.16332824 |
| NU0218658 | 2 | 95.16388553 |
| NU0221096 | 2 | 95.88501249 |
| NU0220530 | 2 | 96.27853586 |

TABLE 4-continued

Genetic markers on melon chromosomes linked to virus resistance traits of interest.

| Marker name | Chromosome | Map position (cM) |
|---|---|---|
| NU0220805 | 2 | 96.28786843 |
| NU0219207 | 2 | 97.2542964 |
| NU0218356 | 2 | 97.35009928 |
| NU0220927 | 2 | 97.35009928 |
| NU0218624 | 2 | 97.51390043 |
| NU0243515 | 2 | 98.19441601 |
| NU0219540 | 2 | 98.49965899 |
| NU0219493 | 2 | 98.83192395 |
| NU0219882 | 2 | 98.87356709 |
| NU0221091 | 2 | 98.87412438 |
| NU0220994 | 2 | 98.87523896 |
| NU0243824 | 2 | 98.87523896 |
| NU0220200 | 2 | 98.91708695 |
| NU0218640 | 2 | 98.91906823 |
| NU0218505 | 2 | 98.92164782 |
| NU0218203 | 2 | 100.3382136 |
| NU0219047 | 2 | 102.664891 |
| NU0218842 | 2 | 103.622176 |
| NU0220558 | 2 | 104.2237891 |
| NU0220620 | 2 | 104.9671526 |
| NU0220993 | 2 | 105.1483269 |
| NU0218138 | 2 | 106.3776567 |
| NU0219543 | 2 | 107.0508151 |
| NU0220488 | 2 | 107.2270656 |
| NU0243788 | 2 | 107.2270656 |
| NU0219082 | 2 | 109.9694299 |
| NU0220779 | 2 | 111.6942303 |
| NU0220016 | 2 | 111.7005636 |
| NU0220087 | 2 | 111.7005636 |
| NU0220264 | 2 | 111.8560636 |
| NU0243948 | 2 | 111.8560636 |
| NU0220430 | 2 | 112.2371728 |
| NU0218830 | 2 | 114.0145725 |
| NU0219228 | 2 | 115.921417 |
| NU0218389 | 2 | 117.9810865 |
| NU0244618 | 2 | 117.9810865 |
| NU0219006 | 2 | 118.453265 |
| NU0219836 | 2 | 118.453265 |
| NU0220218 | 2 | 118.9817073 |
| NU0218169 | 2 | 121.468814 |
| NU0221058 | 2 | 122.1873339 |
| NU0243414 | 2 | 122.8824587 |
| NU0218596 | 2 | 123.0559663 |
| NU0218826 | 2 | 123.2670299 |
| NU0219966 | 2 | 123.695847 |
| NU0218446 | 2 | 125.6573116 |
| NU0243702 | 2 | 125.8159286 |
| NU0220458 | 2 | 125.9749803 |
| NU0220764 | 2 | 125.9761989 |
| NU0218720 | 2 | 126.0726332 |
| NU0220270 | 2 | 126.2916364 |
| NU0219034 | 2 | 126.2916364 |
| NU0219225 | 2 | 126.2916364 |
| NU0219249 | 2 | 126.2916364 |
| NU0220959 | 2 | 126.2916364 |
| NU0220964 | 2 | 126.2916364 |
| NU0243940 | 2 | 126.2916364 |
| NU0244513 | 2 | 126.2916364 |
| NU0244537 | 2 | 126.2916364 |
| NU0220054 | 11 | 0 |
| NU0221092 | 11 | 0.579491077 |
| NU0243725 | 11 | 0.676851956 |
| NU0243674 | 11 | 1.181352896 |
| NU0220286 | 11 | 1.251924704 |
| NU0220920 | 11 | 1.255924704 |
| NU0220069 | 11 | 1.309838516 |
| NU0243719 | 11 | 2.551786372 |
| NU0219128 | 11 | 3.280432909 |
| NU0218591 | 11 | 4.468607303 |
| NU0218714 | 11 | 5.392246359 |
| NU0220796 | 11 | 5.614301648 |
| NU0218738 | 11 | 6.025904953 |
| NU0218409 | 11 | 6.025904953 |
| NU0243450 | 11 | 7.440650256 |
| NU0219374 | 11 | 8.375428163 |
| NU0218820 | 11 | 8.64589173 |
| NU0220434 | 11 | 10.10512685 |
| NU0219761 | 11 | 13.2046766 |
| NU0219093 | 11 | 13.84374788 |
| NU0219278 | 11 | 13.95924788 |
| NU0220359 | 11 | 13.95924788 |
| NU0219222 | 11 | 15.17341133 |
| NU0218219 | 11 | 16.9324201 |
| NU0220289 | 11 | 17.00523634 |
| NU0218365 | 11 | 17.08223634 |
| NU0219403 | 11 | 17.08223634 |
| NU0219113 | 11 | 17.11473172 |
| NU0221042 | 11 | 17.97523187 |
| NU0220691 | 11 | 21.34786778 |
| NU0220165 | 11 | 21.71642696 |
| NU0218764 | 11 | 21.73355638 |
| NU0218299 | 11 | 22.4309501 |
| CmG3478 | 11 | 22.4309501 |
| NU0219414 | 11 | 22.83068043 |
| NU0219288 | 11 | 23.06973484 |
| NU0219419 | 11 | 24.15879707 |
| NU0244606 | 11 | 25.6355839 |
| NU0218483 | 11 | 26.89140175 |
| NU0218544 | 11 | 26.89578504 |
| NU0218959 | 11 | 26.89578504 |
| NU0218902 | 11 | 27.21507391 |
| NU0218954 | 11 | 27.21507391 |
| NU0220821 | 11 | 27.21507391 |
| NU0244632 | 11 | 27.21507391 |
| NU0219830 | 11 | 27.85759349 |
| NU0218768 | 11 | 28.86327875 |
| NU0221100 | 11 | 28.86327875 |
| NU0219539 | 11 | 28.87557456 |
| SE723 | 11 | 29.92114575 |
| NU0218070 | 11 | 33.40862868 |
| NU0220134 | 11 | 35.76768479 |
| NU0220967 | 11 | 35.80618479 |
| NU0220486 | 11 | 37.94141179 |
| NU0219106 | 11 | 38.96729613 |
| NU0218654 | 11 | 40.05361767 |
| NU0219300 | 11 | 40.14572756 |
| NU0218916 | 11 | 40.92381096 |
| NU0218229 | 11 | 41.07298503 |
| NU0219099 | 11 | 41.07298503 |
| NU0219188 | 11 | 41.65192069 |
| NU0219801 | 11 | 41.66548076 |
| NCMEL008383076 | 11 | 41.89 |
| NU0218433 | 11 | 42.20446289 |
| NU0220960 | 11 | 42.37048076 |
| NU0218933 | 11 | 42.41083198 |
| NCMEL008383077 | 11 | 43.437 |
| NU0218595 | 11 | 43.62110094 |
| NU0218967 | 11 | 43.63891132 |
| NU0218656 | 11 | 44.62607776 |
| NU0218779 | 11 | 44.62607776 |
| NU0220729 | 11 | 44.62607776 |
| NCMEL008383075 | 11 | 45.79 |
| NCMEL008383078 | 11 | 46.62 |
| NU0221009 | 11 | 46.99340816 |
| NU0219002 | 11 | 47.05320136 |
| NU0219293 | 11 | 47.94879191 |
| NU0220333 | 11 | 47.94879191 |
| NU0218835 | 11 | 49.00993938 |
| NU0244142 | 11 | 51.01781843 |
| NU0218132 | 11 | 52.59788198 |
| NU0218032 | 11 | 53.43954174 |
| NU0218745 | 11 | 53.43954174 |
| NU0219710 | 11 | 53.43954174 |
| NU0218951 | 11 | 53.47802543 |
| NU0218514 | 11 | 53.55499282 |
| NU0219090 | 11 | 54.60895211 |
| NU0220889 | 11 | 54.60895211 |
| NU0220093 | 11 | 56.47533558 |

TABLE 4-continued

Genetic markers on melon chromosomes linked to virus resistance traits of interest.

| Marker name | Chromosome | Map position (cM) |
|---|---|---|
| NU0219542 | 11 | 56.64158558 |
| NU0219400 | 11 | 56.64308558 |
| NU0243680 | 11 | 56.64308558 |
| NU0218709 | 11 | 58.40296509 |
| NU0218218 | 11 | 59.92977682 |
| NU0219398 | 11 | 59.92977682 |
| NU0244676 | 11 | 60.47061523 |
| NU0219055 | 11 | 60.51306833 |
| NU0243512 | 11 | 61.56346641 |
| NU0218204 | 11 | 61.68875818 |
| cc10099 | 11 | 61.68875818 |
| NU0218968 | 11 | 63.02817506 |
| NU0220157 | 11 | 64.93671828 |
| NU0219383 | 11 | 65.47470549 |
| cc10068 | 11 | 65.93661215 |
| NU0219583 | 11 | 66.28255663 |
| NU0218958 | 11 | 68.24652465 |
| NU0219810 | 11 | 68.24652465 |
| NU0218770 | 11 | 68.29128671 |
| NU0221035 | 11 | 68.67305663 |
| NU0219652 | 11 | 68.90655663 |
| SE899 | 11 | 68.90655663 |
| NU0220829 | 11 | 69.38877236 |
| NU0218382 | 11 | 69.38877236 |
| NU0219639 | 11 | 69.38877236 |
| NU0218676 | 11 | 72.90585647 |
| NU0218092 | 11 | 72.90585647 |
| NU0218924 | 11 | 74.29384966 |
| NU0244357 | 11 | 74.29384966 |
| NU0244370 | 11 | 74.32208492 |
| NU0218909 | 11 | 74.34956443 |
| NU0218784 | 11 | 74.55728442 |
| NU0219846 | 11 | 74.55728442 |
| NU0218786 | 11 | 75.10634538 |
| NU0218898 | 11 | 75.27259481 |
| NU0220496 | 11 | 76.50873929 |
| NU0220610 | 11 | 76.53636781 |
| NU0221008 | 11 | 76.64786781 |
| NU0219742 | 11 | 76.78559315 |
| NU0221014 | 11 | 76.82273929 |
| NU0220618 | 11 | 77.11334843 |
| NU0220490 | 11 | 77.17143096 |
| NU0220250 | 11 | 77.18339337 |
| NU0219563 | 11 | 77.68620247 |
| NU0218792 | 11 | 78.60068556 |
| NU0220322 | 11 | 78.61224748 |
| NU0220834 | 11 | 79.15342413 |
| NU0219586 | 11 | 79.19192413 |
| NU0219609 | 11 | 79.51510282 |
| NU0219770 | 11 | 80.30342396 |
| NU0220053 | 11 | 80.30342396 |
| NU0218381 | 11 | 85.17084048 |
| NU0218827 | 11 | 85.17084048 |
| NU0243884 | 11 | 85.17741568 |
| NU0219608 | 11 | 85.18545202 |
| NU0219718 | 11 | 85.18545202 |
| NU0218825 | 11 | 85.97190691 |
| NU0219151 | 11 | 88.05836653 |
| NU0220794 | 11 | 88.42669556 |
| NU0218117 | 11 | 88.79685958 |
| NU0219370 | 11 | 88.83425114 |
| NU0243739 | 11 | 91.54378039 |
| NU0244493 | 11 | 91.54378039 |
| NU0218536 | 11 | 92.03358083 |
| NU0220903 | 11 | 92.03358083 |
| NU0243879 | 11 | 92.03358083 |
| NU0218642 | 11 | 92.51885845 |
| NU0218304 | 11 | 92.74403775 |
| NU0220837 | 11 | 94.00804258 |
| NU0220463 | 11 | 94.31720706 |
| NU0220183 | 11 | 95.89334078 |
| NU0218510 | 11 | 96.51229354 |
| NU0220347 | 11 | 96.74184742 |
| CmCT160a + b | 11 | 98.36261107 |
| NU0218578 | 11 | 98.36261107 |
| NU0243558 | 11 | 99.1399082 |
| NU0218253 | 11 | 99.4396658 |
| NU0218270 | 11 | 99.4396658 |
| NU0243423 | 11 | 99.4396658 |
| NU0219914 | 11 | 100.3864252 |
| NU0219773 | 11 | 102.7694017 |
| NU0219778 | 11 | 102.7694017 |
| NU0219724 | 11 | 102.9062938 |
| NU0243301 | 11 | 103.6458855 |
| NU0218969 | 11 | 103.992192 |
| NU0243936 | 11 | 106.2476904 |
| NU0243959 | 11 | 106.2597459 |
| NU0219521 | 11 | 107.7868211 |
| NU0219584 | 11 | 107.9680882 |
| NU0221076 | 11 | 107.9680882 |
| NU0219407 | 11 | 108.8878396 |
| NU0219697 | 11 | 109.0170254 |
| NU0218804 | 11 | 109.0170254 |
| NU0218518 | 11 | 109.0590254 |
| NU0220203 | 11 | 109.0590254 |
| NU0218349 | 11 | 109.807591 |
| NU0219661 | 11 | 114.4052332 |
| NU0243718 | 11 | 114.5233688 |
| NU0243425 | 11 | 114.6985556 |
| NU0244342 | 11 | 116.3244118 |
| NU0219291 | 11 | 116.542881 |
| NU0218099 | 11 | 116.7661255 |
| NU0219663 | 11 | 116.8728498 |
| NU0219135 | 11 | 116.8728498 |
| NU0219731 | 11 | 116.8728498 |
| NU0218712 | 11 | 117.1195388 |
| NU0218111 | 11 | 117.1195388 |
| NU0218280 | 11 | 117.1195388 |
| NU0218707 | 11 | 117.1195388 |
| NU0219247 | 11 | 117.1195388 |
| NU0219537 | 11 | 117.1195388 |
| NU0243774 | 11 | 117.1195388 |
| NU0219487 | 11 | 119.2967146 |
| NU0218655 | 11 | 121.8943271 |
| NU0218406 | 11 | 122.2483386 |
| NU0244045 | 11 | 122.2483386 |
| NU0220139 | 11 | 122.2483386 |
| NU0218878 | 11 | 122.4091346 |
| SE927 | 11 | 122.5797701 |
| NU0243947 | 11 | 122.6028634 |
| NU0219393 | 11 | 122.8854578 |
| NU0218289 | 11 | 122.8854578 |
| NU0220614 | 11 | 124.9158327 |
| NU0244789 | 11 | 124.9158327 |
| NU0243339 | 11 | 126.5084681 |
| NU0243829 | 11 | 126.5129674 |
| NU0243988 | 11 | 126.8156232 |
| NU0219430 | 11 | 133.3776428 |
| NU0219397 | 11 | 138.027749 |
| NU0221082 | 11 | 139.4296606 |
| NU0218873 | 12 | 0 |
| NU0219732 | 12 | 0.524202775 |
| NU0243348 | 12 | 3.475832734 |
| NU0219253 | 12 | 9.612296569 |
| NU0219368 | 12 | 10.02661869 |
| NU0243273 | 12 | 10.02661869 |
| NU0218397 | 12 | 10.19352794 |
| NU0220542 | 12 | 10.19352794 |
| NU0220640 | 12 | 10.19352794 |
| NU0220164 | 12 | 11.66636775 |
| NU0220298 | 12 | 11.66636775 |
| NU0220815 | 12 | 11.66636775 |
| NU0221084 | 12 | 13.44515144 |
| NU0218338 | 12 | 13.44515144 |
| NU0218681 | 12 | 15.28711456 |
| NU0219647 | 12 | 17.52023559 |
| NU0218777 | 12 | 17.52146696 |
| NU0218921 | 12 | 19.91221103 |

TABLE 4-continued

Genetic markers on melon chromosomes linked to virus resistance traits of interest.

| Marker name | Chromosome | Map position (cM) |
|---|---|---|
| NU0218108 | 12 | 22.89123568 |
| NU0243668 | 12 | 23.7542249 |
| NU0243767 | 12 | 23.7542249 |
| NU0219517 | 12 | 28.68748661 |
| NU0219050 | 12 | 29.95460323 |
| NU0219834 | 12 | 29.96041247 |
| NU0220934 | 12 | 29.96041247 |
| NU0218053 | 12 | 29.96041247 |
| NU0244550 | 12 | 29.96041247 |
| NU0219654 | 12 | 31.74397834 |
| NU0220999 | 12 | 31.74397834 |
| NU0243817 | 12 | 31.74397834 |
| NU0218055 | 12 | 31.74397834 |
| NU0219615 | 12 | 31.74397834 |
| NU0221081 | 12 | 31.92482213 |
| NU0218605 | 12 | 32.7086158 |
| NU0218931 | 12 | 32.94779845 |
| NU0218994 | 12 | 32.94779845 |
| NU0243783 | 12 | 32.94779845 |
| NU0219820 | 12 | 33.1869811 |
| NU0218475 | 12 | 34.15754871 |
| NU0243561 | 12 | 34.46188978 |
| NU0219343 | 12 | 34.76499704 |
| NU0219170 | 12 | 35.48163568 |
| NU0218834 | 12 | 39.61066417 |
| NU0220916 | 12 | 39.6270824 |
| NU0243358 | 12 | 39.77151577 |
| NU0218362 | 12 | 39.77151577 |
| NU0218390 | 12 | 39.77151577 |
| NU0243625 | 12 | 39.77199762 |
| NU0218620 | 12 | 39.81488236 |
| NU0220929 | 12 | 39.81488236 |
| NU0218760 | 12 | 39.81488236 |
| NU0218816 | 12 | 39.81488236 |
| NU0220968 | 12 | 39.81488236 |
| NU0219743 | 12 | 39.81970087 |
| NU0243361 | 12 | 40.1855847 |
| NU0218432 | 12 | 40.34025886 |
| NU0219973 | 12 | 40.34025886 |
| NU0219324 | 12 | 40.39846406 |
| NU0219010 | 12 | 41.38733049 |
| NU0243344 | 12 | 41.38733049 |
| NU0218477 | 12 | 41.58191969 |
| NU0218928 | 12 | 41.58191969 |
| NU0219184 | 12 | 42.24060998 |
| NU0220120 | 12 | 42.24060998 |
| NU0244176 | 12 | 42.24060998 |
| NU0219714 | 12 | 43.37621994 |
| NU0219907 | 12 | 43.80825073 |
| NU0243527 | 12 | 44.25702765 |
| NU0219627 | 12 | 44.30905098 |
| NU0219686 | 12 | 44.30905098 |
| NU0220145 | 12 | 44.47221721 |
| NU0218323 | 12 | 44.47221721 |
| NU0218396 | 12 | 44.47221721 |
| NU0219827 | 12 | 44.47221721 |
| NU0243381 | 12 | 44.47221721 |
| NU0243695 | 12 | 44.47221721 |
| NU0218796 | 12 | 44.47221721 |
| NU0219332 | 12 | 44.47221721 |
| NU0220980 | 12 | 45.87976958 |
| NU0220014 | 12 | 46.05091155 |
| NU0220809 | 12 | 46.05091155 |
| NU0218617 | 12 | 46.36834089 |
| NU0219948 | 12 | 46.46036662 |
| NU0220836 | 12 | 46.88602776 |
| SE857 | 12 | 46.90401957 |
| cc10056 | 12 | 47.50653131 |
| NU0219404 | 12 | 47.50653131 |
| NU0221005 | 12 | 47.50653131 |
| NU0243365 | 12 | 47.50653131 |
| NU0243469 | 12 | 47.50653131 |
| NU0218164 | 12 | 48.4192602 |
| NU0243717 | 12 | 48.4192602 |
| NU0219382 | 12 | 49.45362973 |
| NU0219891 | 12 | 49.45362973 |
| NU0244674 | 12 | 49.45362973 |
| NU0219320 | 12 | 49.58286753 |
| NU0218516 | 12 | 49.58286753 |
| CmG3492 | 12 | 49.60712983 |
| NU0220254 | 12 | 49.64551961 |
| NU0218668 | 12 | 49.6520651 |
| CmG3822 | 12 | 49.65861059 |
| NU0218984 | 12 | 49.65861059 |
| NU0218254 | 12 | 49.65861059 |
| NU0218791 | 12 | 49.65861059 |
| NU0244060 | 12 | 49.65861059 |
| NU0218859 | 12 | 51.42643529 |
| NU0218074 | 12 | 51.87481232 |
| NU0218735 | 12 | 51.87558896 |
| NU0243397 | 12 | 51.87558896 |
| NU0244210 | 12 | 51.87558896 |
| NU0244480 | 12 | 51.87558896 |
| NU0219352 | 12 | 52.14772471 |
| NU0218603 | 12 | 53.62216566 |
| NU0220702 | 12 | 53.8257582 |
| NU0220361 | 12 | 53.86087599 |
| NU0220773 | 12 | 53.86087599 |
| NU0220144 | 12 | 54.5470543 |
| NU0220484 | 12 | 55.17212525 |
| NU0218828 | 12 | 55.17212525 |
| NU0220091 | 12 | 55.89263411 |
| NU0220249 | 12 | 56.94278853 |
| NU0218540 | 12 | 58.13043392 |
| NU0219454 | 12 | 58.13043392 |
| NU0220758 | 12 | 59.8021111 |
| NU0218771 | 12 | 59.99619355 |
| NU0221010 | 12 | 60.07641546 |
| NU0220188 | 12 | 60.21631574 |
| NU0219706 | 12 | 60.40264595 |
| NU0219704 | 12 | 60.76231733 |
| NU0243507 | 12 | 61.60966718 |
| NU0219796 | 12 | 62.24884912 |
| NU0218467 | 12 | 63.42114857 |
| NU0244654 | 12 | 63.4973667 |
| NU0220433 | 12 | 63.52405869 |
| NU0219410 | 12 | 63.53478364 |
| NU0218192 | 12 | 63.53478364 |
| NU0220148 | 12 | 65.40508157 |
| NU0218175 | 12 | 65.40508157 |
| NU0220384 | 12 | 65.56483985 |
| NU0220811 | 12 | 65.56483985 |
| NU0220184 | 12 | 66.44064295 |
| NU0218120 | 12 | 66.87160823 |
| NU0220204 | 12 | 66.87160823 |
| NU0220401 | 12 | 67.28760394 |
| NU0218344 | 12 | 67.28760394 |
| NU0219875 | 12 | 70.39184496 |
| NU0220940 | 12 | 70.47935274 |
| NU0243971 | 12 | 70.47935274 |
| NU0219723 | 12 | 70.52096181 |
| NU0220795 | 12 | 71.34158681 |
| NU0220354 | 12 | 71.81858524 |
| NU0220657 | 12 | 71.81858524 |
| NU0218296 | 12 | 74.36821732 |
| NU0218348 | 12 | 74.61584889 |
| NU0220594 | 12 | 74.61584889 |
| NU0220923 | 12 | 75.60974611 |
| NU0219896 | 12 | 75.8009085 |
| NU0219204 | 12 | 75.87585812 |
| NU0218883 | 12 | 75.88487683 |
| NU0220966 | 12 | 76.6413981 |
| NU0221040 | 12 | 77.17908761 |
| NU0218780 | 12 | 77.17908761 |
| CMBR058 | 12 | 77.43721738 |
| NU0218287 | 12 | 77.56847415 |
| NU0220734 | 12 | 77.56847415 |
| NU0220151 | 12 | 77.56847415 |

TABLE 4-continued

Genetic markers on melon chromosomes linked to virus resistance traits of interest.

| Marker name | Chromosome | Map position (cM) |
|---|---|---|
| NU0220622 | 12 | 77.56847415 |
| NU0220725 | 12 | 77.56919958 |
| NU0218705 | 12 | 77.77438134 |
| NU0220591 | 12 | 77.77438134 |
| NU0220306 | 12 | 79.29603953 |
| NU0220865 | 12 | 79.52895166 |
| NU0244700 | 12 | 79.52895166 |
| NU0221018 | 12 | 79.84326339 |
| Pm-2-con | 12 | 80.32536277 |
| Pm-2-R1 | 12 | 80.32536277 |
| Pm-2-R2 | 12 | 80.32536277 |
| Pm-2-R3 | 12 | 80.32536277 |
| NU0218345 | 12 | 81.09801162 |
| NU0219954 | 12 | 81.22002347 |
| NU0220800 | 12 | 81.59372961 |
| NU0218141 | 12 | 81.68196514 |
| NU0219431 | 12 | 82.47150128 |
| NU0220283 | 12 | 82.62014277 |
| NU0244671 | 12 | 82.62014277 |
| NU0219558 | 12 | 83.68151507 |
| CMBR150 | 12 | 84.16843971 |
| NU0218922 | 12 | 84.79950189 |
| NU0218035 | 12 | 86.03156406 |
| NU0219376 | 12 | 86.03156406 |
| NU0244678 | 12 | 86.03156406 |
| NU0219317 | 12 | 86.60269155 |
| NU0218960 | 12 | 86.62642229 |
| NU0220716 | 12 | 86.76049154 |
| NU0218619 | 12 | 89.72644298 |
| NU0219163 | 12 | 90.03826065 |
| NU0218328 | 12 | 90.36418407 |
| NU0219668 | 12 | 90.36418407 |
| cc10051 | 12 | 90.56456327 |
| NU0220141 | 12 | 90.76132908 |
| NU0219043 | 12 | 91.23766493 |
| NU0219970 | 12 | 91.23766493 |
| NU0218700 | 12 | 92.66787676 |
| NU0219185 | 12 | 93.07539745 |
| NU0220882 | 12 | 93.25619114 |
| NU0220913 | 12 | 93.80765241 |
| NU0218119 | 12 | 93.86462238 |
| NU0219459 | 12 | 94.39020904 |
| NU0243764 | 12 | 97.11606425 |
| CMBR040 | 12 | 97.96302974 |
| CMBR097 | 12 | 97.96302974 |
| NU0218666 | 12 | 98.21505968 |
| NU0243585 | 12 | 98.21505968 |
| NU0220517 | 12 | 98.29095818 |
| NU0220639 | 12 | 98.29095818 |
| CMBR077 | 12 | 98.53795852 |
| NU0244051 | 12 | 98.9983828 |
| NU0243754 | 12 | 100.2779543 |
| NU0244225 | 12 | 100.7574383 |
| NU0220872 | 12 | 100.9120098 |
| CmG4837 | 12 | 102.1735532 |
| NU0218837 | 12 | 103.9529945 |
| NU0219411 | 12 | 104.0647791 |
| NU0244425 | 12 | 104.5530428 |
| NU0219264 | 12 | 105.1400743 |
| NU0220252 | 12 | 105.5023022 |
| NU0220933 | 12 | 106.2819298 |
| NU0220802 | 12 | 106.2864188 |
| NU0218824 | 12 | 106.2889416 |
| NU0220833 | 12 | 106.6425556 |
| NU0219007 | 12 | 106.6435556 |
| NU0220146 | 12 | 106.6435556 |
| NU0220450 | 12 | 108.8459907 |
| NU0220509 | 12 | 108.8459907 |
| NU0218946 | 12 | 109.1485385 |
| NU0219131 | 12 | 109.1485385 |
| NU0218488 | 12 | 109.2086222 |
| NU0219168 | 12 | 109.2235385 |
| NU0243533 | 12 | 109.3717208 |
| NU0218464 | 12 | 109.3717208 |
| NU0219072 | 12 | 109.3717208 |
| NU0243351 | 12 | 109.6608628 |
| NU0220720 | 12 | 109.6608628 |
| NU0218136 | 12 | 110.4789252 |
| NU0219145 | 12 | 110.559225 |
| NU0218444 | 12 | 110.5675799 |
| NU0220473 | 12 | 110.6065711 |
| NU0220525 | 12 | 110.6090117 |
| NU0218637 | 12 | 111.0582739 |
| NU0219524 | 12 | 111.4939413 |
| NU0220278 | 12 | 111.5098435 |
| NU0220061 | 12 | 111.6205503 |
| NU0221056 | 12 | 111.6397884 |
| NU0218542 | 12 | 111.6397884 |
| CmG5043 | 12 | 111.6521056 |
| NU0219504 | 12 | 111.6658928 |
| NU0220893 | 12 | 111.6694187 |
| NU0220319 | 12 | 111.8025751 |
| NU0244391 | 12 | 112.0925751 |
| NU0219515 | 12 | 112.0925751 |
| NU0219390 | 12 | 112.6912168 |
| NU0219463 | 12 | 112.6912168 |

Markers listed in Table 4 may be utilized for instance via marker assisted selection (MAS) to identify melon plants comprising resistance to one or more of WMV, ZYMV, and CMV, among other viruses, for instance comprising such virus resistance trait(s) introgressed from virus resistant donor lines such as ME8094 (NCIMB 41653) or other virus resistance donor lines. Associated SNP and sequence information for selected melon virus resistance QTL is found in Table 5.

TABLE 5

SNP and sequence information for selected genetic markers linked to melon virus resistance (SEQ ID NOs: 1-39).

| Marker name | Abbreviation | Chromosome | Map Position (cM) | Allele of resistance donor source | Allele of susceptible parent | DNA Sequence |
|---|---|---|---|---|---|---|
| NU0219106 | Z/W QTL 11 | 11 | 38.96729613 | AA | TT | TTAATTTAAAATATGATCAGAACATCAATTGACAAA TTCTGAATACTATACTTGCACATT[A/T]CCTTCCATAC AAGAAAATATGTGGAACTTCACTCATGGTAGATTCA CATATATATAACTA (SEQ ID NO: 1) |
| NU0218916 | Z/W QTL 11 | 11 | 40.92381 | CC | AA | CCTGCCATGGCACCTACTCGCTGAAAGCAATGCTCC CCACAACAATGCCTTGTCATCAGG[A/C]GCTACATCC |

TABLE 5-continued

SNP and sequence information for selected genetic markers linked to melon virus resistance (SEQ ID NOs: 1-39).

| Marker name | Abbreviation | Chromosome | Map Position (cM) | Allele of resistance donor source | Allele of susceptible parent | DNA Sequence |
|---|---|---|---|---|---|---|
| | | | | | | ATCGATTTCGCTATGTCAAAGGCTTTATCTAGCTCCC CAGATCGAGCTAGC (SEQ ID NO: 2) |
| NU0219099 | Z/W QTL 11 | 11 | 41.07299 | CC | TT | GTGGCTGCAGGATTTTATTTCAGGTACAAAACAATG TCTCTTGTCTCATATACGAACTTA[T/C]GTCCAGCCTC CAAATTCGGCACAAGCCAGATTGGCTTATCAGTTAG CACCATTTAAAGAC (SEQ ID NO: 3) |
| NCMEL00 8383076 | Z/W QTL 11 | | 41.89 | CC | AA | GAGCCCATGACAAGATTCCCTCGCCAAAAGATATGT TAATAACAAAGTAAANTTAANTAC[A/C]GAAATCAT TTCTAAAGTTGAAAAACTAAAATCGATGCTTTAAA AATACCAAAATCAAAA (SEQ ID NO: 36) |
| NCMEL00 8383077 | Z/W QTL 11 | | 43.437 | CC | GG | TTNGTATGGATACAACCCATAANNTCTCAAATGGAA GAAGCAACAAAAAAACAAGAAAAA[C/G]TGGAGTA CAAACTTATCCGCAAGGTGTTCGATGAAAGTCCTCA AAGAAGTATTATTATAA (SEQ ID NO: 37) |
| NU0218656 | Z/W QTL 11 | 11 | 44.62608 | AA | GG | ATGGCTTTTGCAGTGGACCTCTTTACnAAATTCTTCA CCCGATAAACCAGAGATAGTGTT[A/G]AAGGTGAAG TCTTAAATTGTCTGGGCTTGTACAAGAAGTTCACTGA CAAGCTCTTAGTTC (SEQ ID NO: 4) |
| NU0218779 | Z/W QTL 11 | 11 | 44.62608 | TT | GG | CCAGCACAACATTGAATGnAAAACCCGATGCCTTTA CATGTCTTTTAATGTCAATTTTCA[T/G]ACTTCCAATG TCCAAACAGAAAAGGAAAAAACCAAAGAGGTCAAA AGTAGGTTTATTCAA (SEQ ID NO: 5) |
| NCMEL00 8383075 | Z/W QTL 11 | 11 | 45.79 | TT | AA | TTGAAATCTTATGGTTTGAGAATTGCCATGTCACTAT CCTTTTAGTTTGTGTAATTTTCAWGTTGCTACTTATT TGGCTCTGGTCATAGAGATCTGTAATGGTTTATTTTT AAGGGGGTAA (SEQ ID NO: 38) |
| NCMEL00 8383078 | Z/W QTL 11 | 11 | 46.62 | CC | AA | TGAAGGCCATTGATAATTCACTAAAGGTACTATAAG AGCCGTGCCTGCTAACCTGCATTC[A/C]GTTATTTTG GTCAAAGAAAGCAATAAACAACAAAGCAAATAAAT CAAATGGGAANAAAC (SEQ ID NO: 39) |
| NU0220333 | Z/W QTL 11 | 11 | 47.94879 | GG | AA | AATTCGTAGAGAGCGTCCTGAACTCCTAGAGAGCGT AAGAGGGTGAGCTACTAACTCATT[A/G]TAGGTTGTT GGTTGAGATCCATGTTAATTGGGAGAACATGGGCAT TTGCCATCAGACTAG (SEQ ID NO: 6) |
| NU0219293 | Z/W QTL 11 | 11 | 47.94879 | TT | GG | CTTGTGAAGCTCATACGAGAGAACAAGATGATGAGT CATACAAAGCCGATGTGGCTTCAT[T/G]GGATGATTT GGACCAAAGTAAACACTTCCCACGTCCCCTGCAAAA CCATATTTTATGCAA (SEQ ID NO: 7) |
| NU0218835 | Z/W QTL 11 | 11 | 49.00994 | CC | TT | TCCTAGCCCTTTATCAAGGTTATGTCTCCTATTTACC TTTAGACCGACCCATGACGGTTA[T/C]CTAGATATGT CTAGTAGCATTGCACTCTCGGAAGTCCAAACGTCAA CATTGACCTGCCTG (SEQ ID NO: 8) |
| NU0244142 | Z/W QTL 11 | 11 | 51.01782 | CC | AA | ATTGAATAAAGCGCACCACCAAGGAAAAGTATCAGT TAGAG[A/C]ATAAAACCAGGAACTAAAATCCTGGAT TTAAATGTCAATGATATGATTTCTTATAGCAAA (SEQ ID NO: 9) |
| NU0219710 | Z/W QTL 11 | 11 | 53.43954174 | GG | AA | TTTTAGTGTCAAAACCCAAAGAGATACCGAAAAGTT TATGTGATTGCAAACAGCACCACC[A/G]TTCTCTTTC CAACAGTTGGAAAATCCTCCTATTCCTCTCCCTCAAG TTTCCTAAAAAATT (SEQ ID NO: 10) |
| NU0243767 | CMV QTL 12 | 12 | 23.7542249 | AA | CC | GGAACGTTGAAGGTGCATTGGTCAGCCCAAATGGCA TAAACAAAAACTCATAGTGCCCTT[A/C]AGGTGTCCA AAAGGCTGTCTTCTCTACATCATCTGCACACATACG ATTTGATGGTAACC (SEQ ID NO: 11) |
| NU0220934 | CMV QTL 12 | 12 | 29.96041247 | TT | CC | GAAATACCAATGCAAGGATTTGAACACAGAACCTCC TAAACCACACTACTCTATTACCAT[T/C]AAAATCGC TGATTGGCCCAAAAGCTTAAACTGATAGGTGAAAGC TTATTTAAAATAATA (SEQ ID NO: 12) |

TABLE 5-continued

SNP and sequence information for selected genetic markers linked to melon virus resistance (SEQ ID NOs: 1-39).

| Marker name | Abbreviation | Chromosome | Map Position (cM) | Allele of resistance donor source | Allele of susceptible parent | DNA Sequence |
|---|---|---|---|---|---|---|
| NU0219654 | CMV QTL 12 | 12 | 31.74397834 | AA | GG | TGTATTAGTTAAAGAAATTGTTGAATGATATACTTAC GCTAAGACCACTCTAATGACGAT[A/G]ACCACCACGT TTTCATGGTAGCAAGATTTTATCCCATATTGTAGCTG CAAGTAAAAAGTA (SEQ ID NO: 13) |
| NU0219170 | CMV QTL 12 | 12 | 35.48163568 | CC | GG | TGACTTCTGTCCACAGAGCTCGCCACTTCTAATTTAC ATATCTACAAATTTCCAATGCCA[C/G]ATTGATATTG GTGTGACCTTTCTCATTCACTGATCATCAATCTCCAT TTTTCTTGCACTG (SEQ ID NO: 14) |
| NU0243358 | CMV QTL 12 | 12 | 39.77151577 | GG | TT | ATACTTTCGACGTAGCTTTATCGTTGTCAGTTCATCA CTCGCCTGTGACGATTTGAATAA[T/G]CACAGGCTTA GCTTAACCTCTCCATTAATTGGGGTTCACTTGGCTGT GACCAAAACTAAG (SEQ ID NO: 15) |
| NU0219184 | CMV QTL12 | 12 | 42.24060998 | CC | TT | ACCATCGATTTGCGTATCATTTACTAGGTGAGTTGTT TTCAATGTATTGGAATACCATTT[T/C]ATCTGCACTAT ATAGATTGATAATGAAAATTCTTTGTTTCCTCTCGTC TACCACGTTCAT (SEQ ID NO: 16) |
| NU0219714 | CMV QTL12 | 12 | 43.37621994 | AA | GG | CATAGAAGTCAAGTGATATAAAGAGAGAAACGTAA AGCATAGAGGTTTATCCTTACAGTC[A/G]CTTGTTCT CTAAAACATACATTTCCTCCACATCACCTACAAAAC ATTTAACCATATGAGA (SEQ ID NO: 17) |
| NU0218323 | CMV QTL12 | 12 | 44.47221721 | AA | GG | CTACATAAAGCCCTATCGATAGAGGTCTCCAGGTAC AATAGTTTCTAGCTAGAGTTAAGG[A/G]AAAGACAA ACATTGTGTAATTGGATAGTTAATGTGGATTAATCCC AGGTTTCATGTTCTA (SEQ ID NO: 18) |
| NU0220980 | CMV QTL12 | 12 | 45.87976958 | AA | GG | CACCACCTTTGACATCACCAAAGGCCGCTTCTCCCTC TCCCTACAAATACTATTGGCGAC[A/G]GCTTCTCCTT TTGGTTGACAAAGGTTTATGGCCCTTGCCGATACAA GGATAGGCCTACAT (SEQ ID NO: 19) |
| NU0243527 | CMV QTL12 | 12 | 44.25702765 | GG | AA | ACACAGAGTCGGCGCATCTCTTnGAAACCCTATATG ACCGTGAGAAGATGATGGTGCTTT[A/G]ATTCTCTTA CGCAGTACACATTTCCCAAGGCGAGTTAAACTTCAA AATTTAAAAACTATG (SEQ ID NO: 20) |
| NU0220836 | CMV QTL12 | 12 | 46.88602776 | AA | GG | TCTTTCCCAGATTAATGGCTAGGAATTTACTCGGATG GTTATTTCTAGAAGTTTTAGTTC[A/G]ATTCTTCCGCA GATTCCCTCCCTTTCAACGGTTGTAACAACTCCCAnA ATTACTCCAAAT (SEQ ID NO: 21) |
| NU0218164 | CMV QTL 12 | 12 | 48.4192602 | AA | GG | GTCCTGAGAAGCACAAATACAAATACAAGAAAG[A/ G]AGGATAACCTGATACAAACATGGTAGCATGTCAT ATTTAAAAATCTAGTTATGCTTCAAA (SEQ ID NO: 22) |
| NU0218516 | CMV QTL 12 | 12 | 49.58286753 | CC | AA | GAGATAGAGAAAGAAGTAGATAAAGTGATTTCCCG GATTAGAGAAGTAGGGTCAAAAGTA[A/C]GAAGCAA ATTCGACTCCGATGGTACAGTTGTTCAATCTGAGAA CTTGTTGCAnnCGGTGC (SEQ ID NO: 23) |
| NU0218074 | CMV QTL12 | 12 | 51.87481232 | TT | AA | AACAGAAAAGATCAAGAATGAAATGAAAAGGACCT TTAAAAGGGAAGCGAAGGCTCTATT[A/T]CTCTTGGA TGTAACTTAAGAAACCTCATAAACATTCAAAGTTTC AAGCTCAACCATAAAA (SEQ ID NO: 24) |
| NU0218603 | CMV QTL12 | 12 | 53.62216566 | CC | TT | CTTATGCTTGAATTAGTAATTTTTGTGTTTTCAGTTCT GTGTAGATCCATTTTTTATGCC[T/C]TTCACGTGAAA GCCATTATTAGTGGGTTnAAAATGATGTATCATTTTG CTGCTTCTTAAC (SEQ ID NO: 25) |
| NU0220144 | CMV QTL12 | 12 | 54.5470543 | TT | CC | CATACCGAAAGAAGGCAGTCCAGTCGGCCATGGTCG TTTCAGTCTAAGCGGAAACGGTGA[T/C]GGATACATT GGAAATGTTGTCAGTGGTTCAATTTCCCACAAAGAC ACTCTTGGCTGTCGT (SEQ ID NO: 26) |

TABLE 5-continued

SNP and sequence information for selected genetic markers linked to melon virus resistance (SEQ ID NOs: 1-39).

| Marker name | Abbreviation | Chromosome | Map Position (cM) | Allele of resistance donor source | Allele of susceptible parent | DNA Sequence |
|---|---|---|---|---|---|---|
| CMBR041-forward | zym-1 | 2 | 3.2644086 | — | — | GTACCGCCTAGGGTTTCTCC (SEQ ID NO: 27) |
| CMBR041-reverse | zym-1 | 2 | 3.2644086 | — | — | CGAGGAAGAGAGAGAAGGGG (SEQ ID NO: 28) |
| NU0218531 | zym-1 | 2 | 5.74 | AA | GG | TGTCCAAGGATTTTGTGTTTTCCAGATCAGGAAACC AGTGTACTTCTTCCACATTCGGCT[A/G]TTCCAGCCTT CGATTAGAGCTCGATATTGGATGTAATTANNNANNN NNNNCNNN (SEQ ID NO: 29) |
| NU0220476 | CMV QTL 2 | 2 | 80.09862541 | TT | CC | GAATGCTTCCTTTCACATATTTTCTGTGATATTCTTTT CCCTGAACAATGCTGAACCGAA[T/C]ATGGTATCATA TGGATGGATTTATTTATCATATAATTTTCAAAACTTA ATTATATAGCAT (SEQ ID NO: 30) |
| NU0218624 | CMV QTL 2 | 2 | 97.51390043 | TT | GG | TCATTGAGTTCAATCGTATGAAGTACTTCTGTGCATG ACTGGCCACTTGAGTCGGTGTTC[T/G]GGATATAACG AAGTTTCTTGAAATGCTTCTCCAATCCCCTTTCCCAA ACTTATCTAGACC (SEQ ID NO: 31) |
| NU0219047 | CMV QTL 2 | 2 | 102.664891 | GG | AA | GATCTTTTGAATTACTATTCCTCAACATATCCTTATA ATTTTCATATATCATCACCAAAC[A/G]TTCATCATTTT TCCCTCCATTCTATCAACCAATCCTTCAAACAATCAC AACTCCAAAGAG (SEQ ID NO: 32) |
| NU0220488 | CMV QTL 2 | 2 | 107.2270656 | CC | TT | CGTACAGACGGATTGCGCAATGAAGCTATCCCATTT TAACTTCAACAATGAAACGCATCT[T/C]CTCAGCGGC ATTTCATCGAACAATATGGCGAGCGTGCATTGCTAT GCACGGAGAAAnCCC (SEQ ID NO: 33) |
| NU0220264 | CMV QTL 2 | 2 | 111.8560636 | AA | TT | CAGTGATATGATAAAATACAAGAATTATGAAGGCTG AAGTTCGAATGAATCTACAATAAT[A/T]GGGTTTTGT TACATAAATCTGAAGTAAAAACTTAnTGAGGCATAC ATTTTTGCATGGAAT (SEQ ID NO: 34) |
| NU0219006 | CMV QTL 2 | 2 | 118.453265 | TT | CC | ATCAGGGGTCTGAAGCTGATAATGATGCTGTAAGAA ATAAGATAGAAGAACCTCACAGAA[T/C]GCTTGGTA CTATATCTGGAGAGCATACTACAGTTTCTGATCAGC ACGCGGTTACTAATGA (SEQ ID NO: 35) |

Example 2: Identification of Genetic Markers Linked to WMV and ZYMV Resistance Traits Genetic markers were identified on melon chromosome 11 which are linked to QTL loci conferring resistance to WMV and ZYMV. These two virus resistance traits map closely on chromosome 11. Six F2 segregating populations derived from crosses of PMR45 (a publicly available Western Shipper type melon) and five elite Charentais-type lines to ME8094 were phenotyped for ZYMV and WMV resistance as shown in Table 6 in order to identify and to validate the presence of the "W/z" QTL locus of melon chromosome 11 conferring such resistance. 120 seedlings from each of the six populations were genotyped using markers linked to the W/z locus (resulting in 6-11 polymorphic markers in different F2 populations). In addition, 172 lines of an F5 mapping population derived from a cross of Mbnr992×GA35PMT were phenotyped for ZYMV (Table 6) and the population was genotyped using 134 TaqMan markers that covered the melon genome.

TABLE 6

F2 and F5 segregating populations phenotyped for ZYMV and/or WMV and their pedigrees.

| segregating pop. | gen | pedigree | # F2 plants phenotyped for: ZYMV | # F2 plants phenotyped for: WMV | # plants for QTL mapping analysis: ZYMV | # plants for QTL mapping analysis: WMV |
|---|---|---|---|---|---|---|
| F2 PMR45 × ME8094 | F2 | PMR45/ME8094:1. | 120 | 120 | 117 | 114 |
| F2 VC1 × ME8094 | F2 | DX_404.404.3.2/ME8094:8. | 120 | 120 | 117 | 111 |
| F2 VC2 × ME8094 | F2 | DX_225.1J/ME8094:9. | 120 | 120 | 118 | 109 |
| F2 VC3 × ME8094 | F2 | DX_89.95.1.7.1.1.4.M/ME8094:7. | 120 | 120 | 105 | 109 |
| F2 VC4 × ME8094 | F2 | DX_94.94.3.16.2.3.17.10.1/ME8094:7. | 120 | 120 | 111 | 114 |

TABLE 6-continued

F2 and F5 segregating populations phenotyped for ZYMV and/or WMV and their pedigrees.

| segregating pop. | gen | pedigree | # F2 plants phenotyped for: | | # plants for QTL mapping analysis: | |
|---|---|---|---|---|---|---|
| | | | ZYMV | WMV | ZYMV | WMV |
| F2 VC5 × ME8094 | F2 | DX_1901.A1/ME8094:8. | 120 | 120 | 111 | 108 |
| F5 mapping pop | F5 | C2_Mbnr992/GA35PMT:7.3.1@.0001a. | 172 | — | 163/143* | — |

*163 individuals used for non-parametric interval mapping; 143 individuals used for binary interval mapping.

Analysis was conducted using single-marker regression, non-parametric interval mapping and/or binary interval mapping. Briefly, the F2 segregating population indicated that the most likely location of the W/z locus is in the interval of NU0218779 (or NU0218656) to NU0218835 (44.6 to 49.0 cM on linkage group 11 as shown in Table 4). Only one of the six mapping populations (VC5×ME8094) indicated association of WMV with markers upstream of this interval (NU0219106 at 39.0 cM); however, this population showed significant distortion of the expected phenotypic segregation ratios at both the F1 and F2 generations and was therefore not considered accurate. This led to a further reduction of the identified genetic interval comprising W/z, as previously the locus was mapped in the interval of 38.97 to 53.44 cM and additional breeding studies further refined the interval to 40.92 to 51.02 cM.

WMV and ZYMV resistance was mapped from the source Mbnr992 (Table 1). Mbnr992 was developed by self-pollinating ME8094. Mbnr992 carries resistances to CMV, WMV, and ZYMV. Inheritance of the ZYMV resistance from Mbnr992 is recessive. Inheritance of WMV resistance from Mbnr992 is mainly dominant, although heterozygotes can show intermediate resistance depending upon weather conditions and virus pressure.

When using Mbnr992 as the resistance donor for breeding, segregating populations demonstrated a very high correlation of resistance to both WMV and ZYMV, suggesting tight linkage of loci (or a single locus) controlling resistance to these two viruses. An F6 RIL population from Mbnr992× GA35Pmt was phenotyped for virus resistance and genotyped for markers along the melon chromosome. The parent line GA35Pmt is susceptible to WMV, ZYMV, and CMV. From this data the ZYMV resistance locus was mapped to chromosome 11, at approximately 44 to 53 cM, and a close linkage, or co-segregation of a locus controlling resistance to WMV was observed. To verify that WMV is located in this same region as ZYMV two studies were conducted. In the first experiment a selected set of individuals that were recombinant in the ZYMV region were selected from 67 lines of the RIL population Mbnr992/GA35PMT, and a WMV screen was performed. Individual plant scores were taken and Least Square Means (LSM) for WMV score based on plot averages were used to do the QTL analysis. The QTL analysis showed that the major QTL peak was on linkage group 11 in the same region in which ZYMV had previously been mapped, demonstrating that the locus for WMV resistance is co-locating with the ZYMV resistance locus.

A second experiment was then conducted to identify the location of the WMV locus. In this study a BC4F2 population was screened for WMV resistance, and ZYMV resistance was scored on the plants that survived the WMV screen. The plants were genotyped with all the polymorphic markers in the putative WMV/ZYMV region. There were a total of 276 plants, 191 of which were available to also collect the ZYMV resistance data. Markers NU021906 (p<0.01), NU0218656 (p<0.01), NU0219710 (p<0.01), and NU0219542 (p<0.05) were significantly correlated with the WMV resistance trait, while marker NU0218656 correlated with the ZYMV resistance trait (p<0.01). Two markers required follow-up analysis and were subsequently dropped from further analysis. These were NU0218779 and NU0218514. The analysis showed that the WMV resistance trait derived from Mbnr992 source (i.e. ME8094) is located in the same region as the ZYMV resistance trait. Marker NU0218656 demonstrated the tightest linkage to the WMV resistance trait, followed by NU0219710. The strongest significance for ZYMV resistance was found for the marker NU0218656. Thus the two traits co-located.

ZYMV resistance was also mapped from the source PI414723 which carries the zym-1 gene. A F6 RIL population from Vedrantais×PI414723 was phenotyped and genotyped for ZYMV resistance. The parent line Vedrantais is a Charentais type, inbred line susceptible to ZYMV. From this data, a single locus (putatively zym-1) was identified on chromosome 2, position 3.2-5.7 cM. Markers for this locus were converted to a high throughput genotyping format, validated in germplasm from breeding programs, and may also be utilized for marker assisted selection for zym-1. Inheritance of the zym-1 resistance for ZYMV is recessive.

Figure 2:
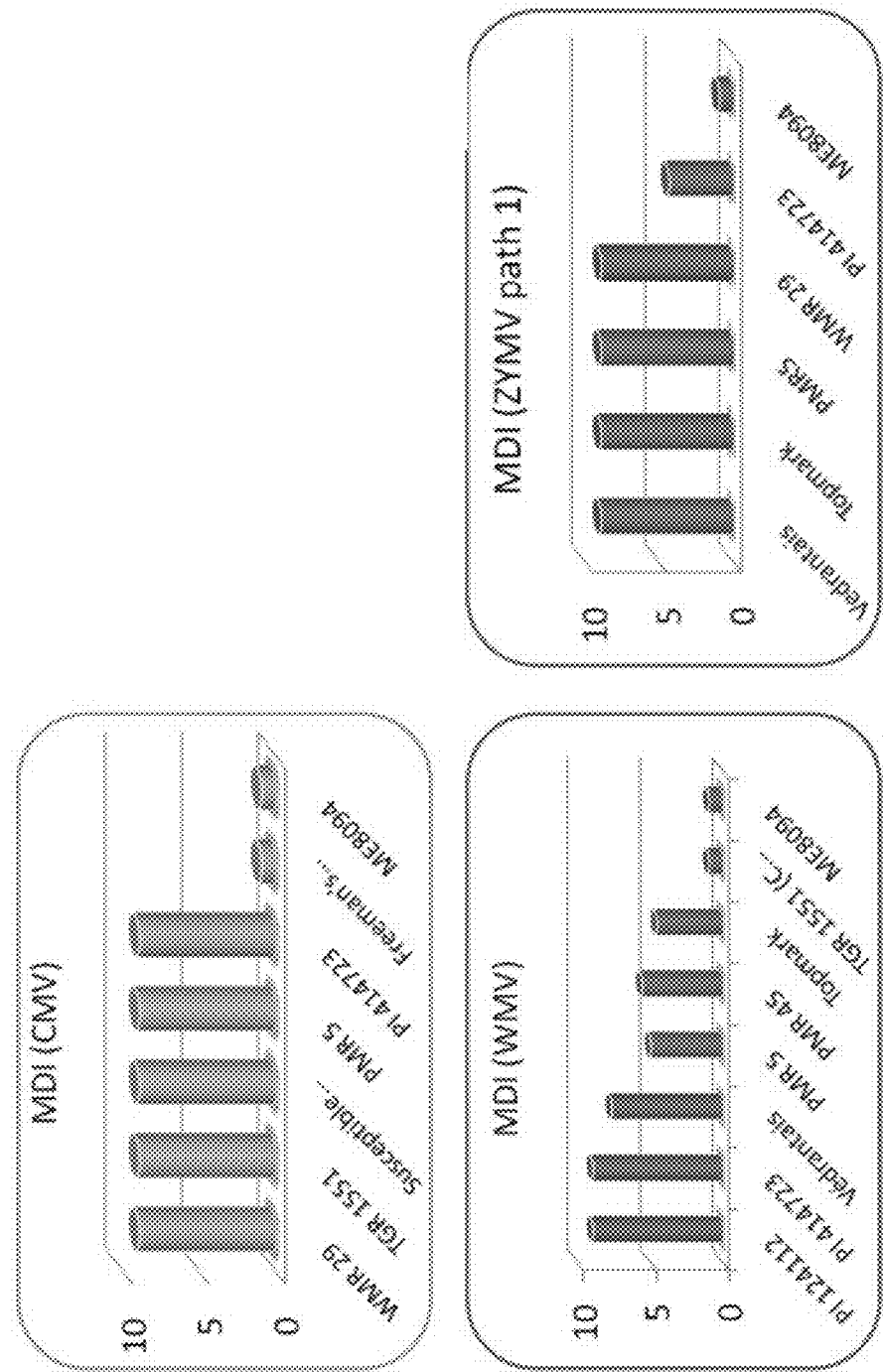
FIG. 2 illustrates the level of viral disease symptoms conferred by resistance traits present in melon line ME8094 when challenged with CMV, WMV, or ZYMV, as compared with other selected melon lines. "Y" axis is denoted by symptom rating scale (1-10).
Figure 3:
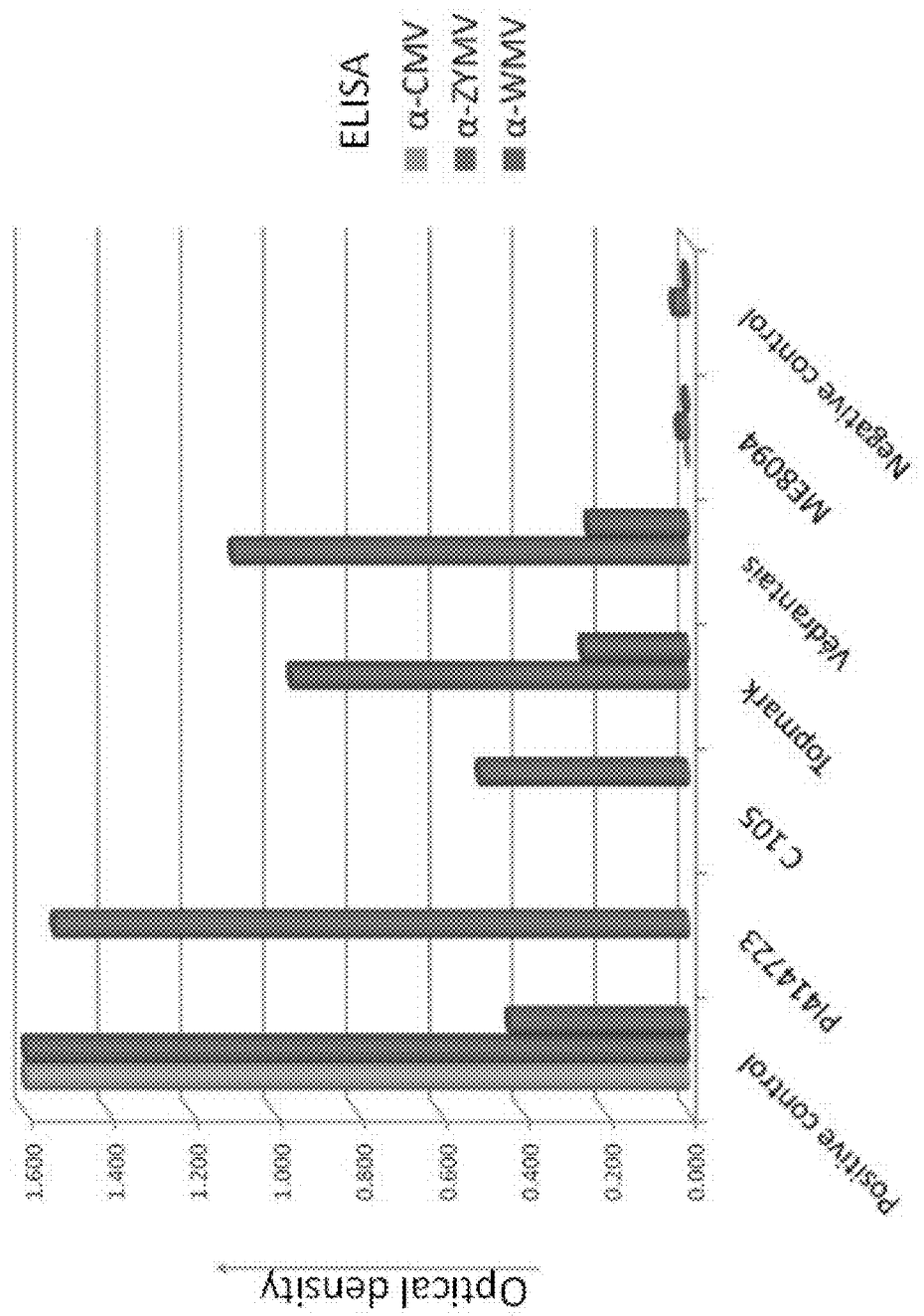
FIG. 3 illustrates the viral titer detected by ELISA in melon line ME8094, after challenge with CMV, ZYMV, or WMV, as compared with other selected melon lines.

The location of the WMV/ZYMV resistance from Mbnr992 and the zym-1 gene from PI414723 on chromosomes 11 and 2, respectively, demonstrates the independent inheritance of these two ZYMV resistance genes. The WMV/ZYMV resistance locus on chromosome 11 is particularly valuable as it provides dual resistance to two viruses, strong resistance to WMV, no or very low virus titer after mechanical viral inoculation (which has until now been unavailable in melon), and a source for resistance to ZYMV which is not associated with the foliar necrosis typical of the previously identified zym-1 gene. FIGS. 2-4 illustrate disease scores and ELISA test results further demonstrating the efficacy of the ZYMV/WMV resistance trait identified in ME8094.

An F5 mapping population from the cross Mbnr992× GA35PMT indicated that marker NU0218779 at 44.6 cM is most tightly linked to the ZYMV and WMV resistance trait, with an additive effect of a=3.83, according to the single marker regression analysis. Non-parametric and binary interval mapping analyses indicated that the QTL peak is located at 46.8 and 45.7 cM, and the 1-LOD interval is 43.25-48.75 and 44.25-48.25, respectively. These intervals are in agreement with the results reported above for five of the F2 segregating populations. Markers in the genetic map interval bounded by NU0219106 and NU0219710 (on linkage group 11 as shown in Table 4) may be utilized, among others, in MAS to identify plants carrying resistance to WMV and ZYMV. Other markers localized to this interval on the melon genetic map may similarly be utilized, such as markers publicly available (e.g. see S. E. Martín, "Caracterizatión Etnobotónica Agro-Morfológica, Sensorial, Físico-Química, Nutricional y Molecular de Las Variedades Locales de Melón de Villaconejos;" Ph.D. Thesis, Universidad Politecnica Madrid, 2010).

Example 3: Breaking Linkage of CMV QTL12 to the Pentamerous Fruit Trait

The genomic interval of CMV QTL12 flanked by the markers NU0243358-NU0220836 (39.77-46.89 cM as listed in Table 4) confers CMV resistance, however the pentamerous fruit phenotype maps to a similar location in the *C. melo* genome, and this undesirable trait is found, for instance, in melon lines comprising an introgression from certain melon lines such as PI161375 and lines derived therefrom. The genetic factor that leads to the pentamerous fruit phenotype in melon has been previously characterized and mapped on LG XII of the ICuGI melon composite map (Périn et al. TAG 104:1017-1034, 2002). Linkage drag resulting in the presence of the undesirable pentamerous fruit trait has however not been observed following introgression of the chromosomal interval from ME8094 for CMV resistance. Thus, use of the CMV resistance trait(s) derived from ME8094 in conjunction with marker assisted breeding allows introgression CMV resistance while avoiding inclusion of the pentamerous trait.

Example 4: Phenotype of ME8094 Donor Line Vs. BC2 Derived Lines Carrying Introgression of Interest Four to six plants of five pedigrees (Table 7) were planted in a greenhouse nursery. The BC2-derived lines described were derived from the cross of the elite WSH-39-1083-AN to the donor parent EXC-C210-ME-8094-1. At the BC1 generation one random line was selected that carried the donor introgression in the genomic region of interest as shown in Table 7. This line was advanced to BC2 generation and was selfed for at least one subsequent generation to allow fixing the donor introgression. Molecular markers were only used to select the donor introgression at the three indicated genomic regions; therefore, it is not known what other regions of the genome may carry donor introgressions.

Plants of the five pedigrees were arranged in order (not randomized) in two neighboring rows of the greenhouse, far from cooling pads so that temperature differences during growth were not an issue. Data were collected at harvest maturity from 2 fruits for each of the plants. Phenotypes recorded were: fruit length and width, cavity length and width, firmness, Brix (soluble solids), and rind and flesh color. Color data were recorded with a handheld colorimeter and final color phenotypes presented are lightness, chroma and hue. Four independent color measurements were collected from the rind and another four from the flesh of each melon fruit (location on the rind and flesh was consistent for all fruits). Also, two measurements of firmness and Brix were recorded for each fruit using a digital handheld penetrometer and refractometer, respectively. Representative fruit from this study are shown in FIG. 6.

TABLE 7

Summary of ME8094 and BC2 lines derived therefrom, carrying indicated introgressions at loci of interest (CMV QTL12, CMV QTL02 or WMV/ZYMV QTL11).

| Pedigree | ME8094 introgression | LG/size of introgression (cM) |
|---|---|---|
| EXC-C210-ME-8094-1 | n/a | n/a |
| C2_WSH-39-1083-AN*3/ EXC-C210-ME-8094-1:0027.0018.0006. | CMV QTL02 | LG2/80.1-118.5 cM |
| C2_WSH-39-1083-AN*3/ EXC-C210-ME-8094-1:0080.0088.0005. | CMV QTL12 | LG12/29.6-65.4 cM |
| C2_WSH-39-1083-AN*3/ EXC-C210-ME-8094-1:0063.0007.0010.0147. | ZYMV/WMV QTL11 | LG11/44.6-51.0 cM |
| C2_WSH-39-1083-AN*3/ EXC-C210-ME-8094-1:0018.0013.0002.0145. | ZYMV/WMV QTL11 | LG11/38.9-56.6 cM |

Table 8 provides phenotypic data for fruit of each pedigree. Mean and standard deviation is also shown for each genotype and trait. These data confirm that the ME8094 donor has more elongated fruit than the BC2-derived lines that carry donor introgressions. The length of the fruit of the ME8094 line was on average 221.07 mm, while that of the BC2 lines ranged from 122.08 to 174.14 mm. Similarly, the size of the cavity was larger in the ME8094 line. Melon fruits of the ME8094 line had also higher firmness (8.62 kgf) than 3 of the 4 BC2-derived lines (4.76 to 5.75 kgf). Soluble solids content (Brix) was very low for fruit of the ME8094 line (3.96° Brix) compared to fruits of the BC2-derived lines (7.94 to 9.55° Brix). FIG. 6 shows the different fruit shape and color of the ME8094 line compared to BC2-derived elite lines carrying donor introgressions at parts of the genome.

TABLE 8

Phenotypic values on a per plant basis for each of the 4 to 6 plants phenotyped for each pedigree.

| Pot number | Pedigree | Width | Length | CavW |
|---|---|---|---|---|
| C212WGH2013-3497 | EXC-C210-ME-8094-1 | 107.92 | 274.67 | 53.685 |
| C212WGH2013-3498 | EXC-C210-ME-8094-1 | 114.04 | 179.07 | 68.48 |
| C212WGH2013-3499 | EXC-C210-ME-8094-1 | 104.03 | 251.33 | 59.14 |
| C212WGH2013-3500 | EXC-C210-ME-8094-1 | 105.44 | 166.17 | 55.82 |
| C212WGH2013-3501 | EXC-C210-ME-8094-1 | 100.64 | 199.77 | 53.9 |
| C212WGH2013-3502 | EXC-C210-ME-8094-1 | 80.92 | 255.40 | 36.455 |
| Mean | | 102.16 | 221.07 | 54.58 |
| St Dev | | 11.33 | 45.16 | 10.44 |
| C212WGH2014-0001 | C2_WSH-39-1083-AN*3/EXC-C210-ME-8094-1:0027.0018.0006. | 100.06 | 149.33 | 54.495 |
| C212WGH2014-0002 | C2_WSH-39-1083-AN*3/EXC-C210-ME-8094-1:0027.0018.0006. | 90.91 | 217.16 | 46.61 |
| C212WGH2014-0003 | C2_WSH-39-1083-AN*3/EXC-C210-ME-8094-1:0027.0018.0006. | 98.23 | 179.58 | 42.89 |
| C212WGH2014-0004 | C2_WSH-39-1083-AN*3/EXC-C210-ME-8094-1:0027.0018.0006. | 111.64 | 150.51 | 54.36 |
| Mean | | 100.21 | 174.14 | 49.59 |
| St Dev | | 8.58 | 31.91 | 5.79 |
| C212WGH2015-0001 | C2_WSH-39-1083-AN*3/EXC-C210-ME-8094-1:0080.0088.0005. | 96.96 | 154.42 | 40.605 |
| C212WGH2015-0002 | C2_WSH-39-1083-AN*3/EXC-C210-ME-8094-1:0080.0088.0005. | 81.62 | 146.84 | 33.105 |

TABLE 8-continued

Phenotypic values on a per plant basis for each of the 4 to 6 plants phenotyped for each pedigree.

| | | | | |
|---|---|---|---|---|
| C212WGH2015-0003 | C2_WSH-39-1083-AN*3/EXC-C210-ME-8094-1:0080.0088.0005. | 97.14 | 141.80 | 46.015 |
| C212WGH2015-0004 | C2_WSH-39-1083-AN*3/EXC-C210-ME-8094-1:0080.0088.0005. | 94.06 | 143.84 | 44.095 |
| C212WGH2015-0005 | C2_WSH-39-1083-AN*3/EXC-C210-ME-8094-1:0080.0088.0005. | 88.62 | 140.08 | 40.64 |
| C212WGH2015-0006 | C2_WSH-39-1083-AN*3/EXC-C210-ME-8094-1:0080.0088.0005. | 95.60 | 149.74 | 48.34 |
| Mean | | 92.33 | 146.12 | 42.13 |
| St Dev | | 6.11 | 5.35 | 5.36 |
| C212WGH2016-0001 | C2_WSH-39-1083-AN*3/EXC-C210-ME-8094-1:0063.0007.0010.0147. | 109.42 | 135.20 | 57.335 |
| C212WGH2016-0002 | C2_WSH-39-1083-AN*3/EXC-C210-ME-8094-1:0063.0007.0010.0147. | 117.65 | 176.04 | 62.135 |
| C212WGH2016-0003 | C2_WSH-39-1083-AN*3/EXC-C210-ME-8094-1:0063.0007.0010.0147. | 114.19 | 153.19 | 59.125 |
| C212WGH2016-0004 | C2_WSH-39-1083-AN*3/EXC-C210-ME-8094-1:0063.0007.0010.0147. | 131.81 | 158.47 | 75.51 |
| C212WGH2016-0005 | C2_WSH-39-1083-AN*3/EXC-C210-ME-8094-1:0063.0007.0010.0147. | 98.92 | 121.32 | 51.98 |
| Mean | | 114.39 | 148.84 | 61.22 |
| St Dev | | 12.02 | 21.18 | 8.80 |
| C212WGH2017-0001 | C2_WSH-39-1083-AN*3/EXC-C210-ME-8094-1:0018.0013.0002.0145. | 104.50 | 117.97 | 32.44 |
| C212WGH2017-0002 | C2_WSH-39-1083-AN*3/EXC-C210-ME-8094-1:0018.0013.0002.0145. | 130.94 | 148.47 | 54.835 |
| C212WGH2017-0003 | C2_WSH-39-1083-AN*3/EXC-C210-ME-8094-1:0018.0013.0002.0145. | 111.63 | 111.78 | 51.35 |
| C212WGH2017-0004 | C2_WSH-39-1083-AN*3/EXC-C210-ME-8094-1:0018.0013.0002.0145. | 127.52 | 114.95 | 48.87 |
| C212WGH2017-0005 | C2_WSH-39-1083-AN*3/EXC-C210-ME-8094-1:0018.0013.0002.0145. | 118.93 | 122.00 | 59.84 |
| C212WGH2017-0006 | C2_WSH-39-1083-AN*3/EXC-C210-ME-8094-1:0018.0013.0002.0145. | 116.18 | 117.33 | 56.39 |
| Mean | | 118.28 | 122.08 | 50.62 |
| St Dev | | 9.84 | 13.36 | 9.70 |

| Pot number | CavL | Firm | Brix | Rind | | | Flesh | | |
| | | | | Lightness | Chroma | Hue | Lightness | Chroma | Hue |
|---|---|---|---|---|---|---|---|---|---|
| C212WGH2013-3497 | 217.63 | 10.54 | 3.68 | 77.45 | 13.18 | 106.90 | 63.45 | 20.25 | 110.05 |
| C212WGH2013-3498 | 127.89 | 7.83 | 4.05 | 77.38 | 13.27 | 102.98 | 63.28 | 17.22 | 104.23 |
| C212WGH2013-3499 | 197.90 | 6.22 | 4.33 | 77.94 | 14.10 | 104.28 | 63.43 | 17.41 | 104.14 |
| C212WGH2013-3500 | 122.89 | 8.21 | 3.78 | 77.19 | 13.30 | 105.57 | 60.53 | 21.93 | 108.40 |
| C212WGH2013-3501 | 148.46 | 10.02 | 3.85 | 77.09 | 12.13 | 108.80 | 63.84 | 18.66 | 110.03 |
| C212WGH2013-3502 | 210.32 | 8.92 | 4.08 | 77.44 | 16.29 | 109.59 | 68.16 | 24.03 | 111.16 |
| Mean | 170.85 | 8.62 | 3.96 | 77.41 | 13.71 | 106.36 | 63.78 | 19.92 | 108.00 |
| St Dev | 42.72 | 1.57 | 0.24 | 0.30 | 1.41 | 2.57 | 2.46 | 2.69 | 3.09 |
| C212WGH2014-0001 | 99.14 | 7.46 | 10.15 | 60.79 | 9.96 | 93.93 | 57.97 | 35.44 | 75.36 |
| C212WGH2014-0002 | 171.34 | 8.96 | 6.60 | 55.23 | 10.88 | 99.65 | 59.87 | 31.34 | 87.34 |
| C212WGH2014-0003 | 129.14 | 9.60 | 5.75 | 51.82 | 7.65 | 106.79 | 63.47 | 31.00 | 81.52 |
| C212WGH2014-0004 | 49.20 | 7.84 | 10.55 | 60.64 | 13.26 | 89.19 | 57.67 | 37.17 | 73.83 |
| Mean | 112.20 | 8.46 | 8.26 | 57.12 | 10.44 | 97.39 | 59.75 | 33.74 | 79.51 |
| St Dev | 51.39 | 0.99 | 2.44 | 4.38 | 2.32 | 7.58 | 2.67 | 3.05 | 6.18 |
| C212WGH2015-0001 | 109.67 | 6.75 | 9.73 | 61.61 | 22.44 | 96.51 | 54.69 | 43.01 | 69.06 |
| C212WGH2015-0002 | 102.03 | 5.33 | 8.15 | 61.54 | 21.09 | 95.59 | 57.12 | 43.37 | 70.30 |
| C212WGH2015-0003 | 96.82 | 6.02 | 10.38 | 56.60 | 11.91 | 100.23 | 55.50 | 43.93 | 68.52 |
| C212WGH2015-0004 | 108.66 | 5.54 | 8.78 | 61.19 | 19.71 | 90.07 | 55.10 | 38.68 | 71.64 |
| C212WGH2015-0005 | 97.74 | 7.64 | 9.85 | 59.28 | 8.85 | 95.63 | 55.61 | 42.09 | 70.64 |
| C212WGH2015-0006 | 107.51 | 3.23 | 10.40 | 65.40 | 22.22 | 97.32 | 57.55 | 35.63 | 73.36 |
| Mean | 103.74 | 5.75 | 9.55 | 60.94 | 17.70 | 95.89 | 55.93 | 41.12 | 70.59 |
| St Dev | 5.66 | 1.50 | 0.90 | 2.91 | 5.84 | 3.33 | 1.15 | 3.27 | 1.76 |
| C212WGH2016-0001 | 80.70 | 4.33 | 9.33 | 60.52 | 11.08 | 102.53 | 52.99 | 31.65 | 113.39 |
| C212WGH2016-0002 | 109.11 | 2.39 | 6.98 | 62.51 | 11.37 | 103.52 | 56.16 | 30.86 | 94.39 |
| C212WGH2016-0003 | 89.11 | 4.89 | 7.93 | 58.82 | 13.76 | 104.40 | 56.10 | 33.56 | 98.58 |
| C212WGH2016-0004 | 105.36 | 6.76 | 9.40 | 57.24 | 13.08 | 102.99 | 53.40 | 31.95 | 111.82 |
| C212WGH2016-0005 | 74.91 | 5.44 | 6.08 | 58.36 | 14.32 | 109.11 | 59.23 | 31.00 | 105.20 |
| Mean | 91.84 | 4.76 | 7.94 | 59.49 | 12.72 | 104.51 | 55.58 | 31.81 | 104.68 |
| St Dev | 14.99 | 1.61 | 1.45 | 2.06 | 1.44 | 2.67 | 2.52 | 1.08 | 8.22 |
| C212WGH2017-0001 | 71.63 | 5.64 | 7.40 | 62.71 | 8.02 | 91.09 | 53.69 | 40.85 | 69.16 |
| C212WGH2017-0002 | 97.88 | 5.32 | 7.68 | 59.67 | 6.94 | 94.76 | 57.37 | 37.58 | 73.82 |
| C212WGH2017-0003 | 78.39 | 5.36 | 9.05 | 60.23 | 7.04 | 93.77 | 54.96 | 39.03 | 74.03 |
| C212WGH2017-0004 | 78.94 | 5.22 | 9.40 | 60.55 | 7.10 | 95.77 | 57.42 | 40.70 | 72.73 |
| C212WGH2017-0005 | 81.29 | 6.13 | 8.43 | 61.49 | 7.92 | 93.16 | 51.12 | 34.88 | 76.14 |
| C212WGH2017-0006 | 70.34 | 6.13 | 6.65 | 62.75 | 8.76 | 93.96 | 54.13 | 39.80 | 71.32 |
| Mean | 79.74 | 5.63 | 8.10 | 61.23 | 7.63 | 93.75 | 54.78 | 38.81 | 72.87 |
| St Dev | 9.88 | 0.41 | 1.05 | 1.30 | 0.72 | 1.59 | 2.39 | 2.27 | 2.41 |

Example 5: Validation of QTL2 Markers in Lines with QTL12 Fixed for the ME8094 Introgression A study was conducted to validate the presence of the CMV genetic factor which was identified in the genomic region of 95.88-118.45 cM on linkage group 2 (LG2) in line ME8094. A total of 16 BC2-derived lines from the cross of WSH-39-1083-AN to ME8094 were tested. Eight entries carried the ME8094 introgression at the CMV QTL12 interval only (QTL2−/QTL12+) and 8 entries carried both CMV QTL2 and QTL12 (QTL2+/QTL12+). Twelve seedlings per replication and 12 replications of each of the 16 entries, as well as the disease control lines Virgos, Paco, Pastis-2, MR1, TopMark, Vedrantais, and the parental lines ME8094 and WSH-39-1083-AN were tested in a complete randomized block design.

Due to the large number of plants, replications 1-6 were sown and inoculated at different timepoints than replications 7-12. Disease scores (in a scale of 1 to 9, 1: resistant, 9: susceptible) were collected for all replications at 9, 15 and 22 days after inoculation. Analysis was conducted using JMP v9 (JMP Software; SAS Institute, Cary, N.C., U.S.A.);

and least square means were derived using the restricted maximum likelihood for replications 1-6 and 7-12 separately, as well as across all replications (Table 9). Mean separation groupings indicate entries with significantly different disease scores. Significant differences were observed between the two timepoints possibly due to differences in inoculation since replications 7-12 were more uniformly and severely attacked by CMV, but means of all entries were ranked similarly across all replications.

These results show that all lines carrying both CMV QTL2 and QTL12 (QTL2+/QTL12+) had significantly higher resistance to CMV at 22 days post-inoculation when compared to lines carrying the ME8094 introgression at the CMV QTL12 interval only (QTL2−/QTL12+), with the exception of entry 12. For entry 12 it is possible that other minor loci controlling CMV resistance may be segregating in the background, leading to a higher level of resistance. Entry 13 also displayed higher levels of resistance than typically observed, and in comparison to other QTL2+/QTL12+ entries in this study, which may also be due to other minor loci controlling CMV resistance derived from ME8094 that may be present in this particular BC2-family.

Thus, when QTL12 is fixed for the ME8094 donor introgression, it is possible to identify statistically significant differences among lines carrying and lines lacking the QTL2 ME8094 introgression.

sion of the ZYMV/WMV QTL of linkage group 11, and flanking donor-derived portions of linkage group 11.

Evaluation of lines that were developed through marker-assisted backcrossing demonstrated significant differences for various phenotypic traits due to linkage drag and background effects when Galia (GAL) and Amarillo (AMA) melons with large introgression at the ZYMV/WMV QTL11 region were tested.

Two of the inbred lines converted with the ZYMV/WMV QTL11 region are GAL-188-DUFFS-AN and AMA-188-DECO-AN. BC3 and BC4 seed of the GAL and AMA converted inbreds, respectively, were obtained, fixed for the ZYMV/WMV QTL11 introgression for the homozygous donor and recurrent parent alleles, and trialed next to the unconverted inbred lines. The two trials were arranged in RCBD designs with 10 replications. A number of traits were evaluated (e.g. fruit size, cavity size, fruit set, brix, firmness, vigor, powdery mildew resistance, netting, sutures, blossom end scar size, rind and flesh color), and data were collected when phenotypic variation was observed among experiment entries.

Two different BC3 families were tested in the GAL trial (6 entries total), which were both derived from the same BC2, while one BC4 family was tested in the AMA trial (3 entries). Genome-wide fingerprinting showed that the percent of recurrent parent for the AMA pedigree was 94.95%

TABLE 9

Least square means and mean separation groupings for disease scores 22 days post-inoculation for all entries and controls.

| Pedigree | Entry | JMP I-all data-22dpi_REML | | | JMP II-rep1-6_22dpi_REML | | | JMP III-rep7-12_22dpi_REML | | |
|---|---|---|---|---|---|---|---|---|---|---|
| | | LSM | Std Error | MSG | LSM | Std Error | MSG | LSM | Std Error | MSG |
| ME-8094 | 17 | 1.040972 | 0.162696 | K | 0.999098 | 0.215223 | J | 0.95292 | 0.23118 | K |
| Virgos | 18 | 1.022317 | 0.222088 | K | 0.997786 | 0.293344 | J | 0.986339 | 0.31602 | K |
| QTL2+/QTL12+ | 13 | 1.111346 | 0.11296 | K | 0.999922 | 0.159501 | J | 1.224711 | 0.148963 | K |
| Paco | 20 | 2.152872 | 0.17591 | J | 1.882778 | 0.230493 | I | 2.433454 | 0.252803 | J |
| Pastis-2 | 21 | 3.823247 | 0.18215 | H | 3.768528 | 0.263583 | G | 3.902406 | 0.234721 | I |
| QTL2+/QTL12+ | 15 | 2.930645 | 0.11626 | I | 2.18832 | 0.161796 | I | 3.699479 | 0.155587 | I |
| QTL2+/QTL12+ | 14 | 2.877832 | 0.112961 | I | 2.222418 | 0.15839 | I | 3.536354 | 0.150007 | I |
| QTL2+/QTL12+ | 4 | 3.112621 | 0.11296 | I | 2.831237 | 0.159502 | H | 3.391398 | 0.148963 | I |
| QTL2+/QTL12+ | 12 | 4.154572 | 0.112567 | GH | 3.69464 | 0.15839 | G | 4.61362 | 0.148963 | H |
| QTL2+/QTL12+ | 16 | 4.303952 | 0.115837 | G | 2.97138 | 0.161799 | H | 5.649089 | 0.154436 | G |
| QTL2+/QTL12+ | 3 | 7.173897 | 0.135083 | F | 6.827129 | 0.198179 | F | 7.476804 | 0.172011 | EF |
| QTL2+/QTL12+ | 1 | 6.964789 | 0.115833 | F | 6.790369 | 0.164203 | F | 7.150718 | 0.152175 | F |
| QTL2+/QTL12+ | 2 | 7.220696 | 0.12542 | F | 7.000267 | 0.181223 | F | 7.420786 | 0.161844 | EF |
| QTL2+/QTL12+ | 9 | 7.763623 | 0.119396 | E | 7.755379 | 0.172115 | DE | 7.77718 | 0.15442 | DE |
| QTL2+/QTL12+ | 11 | 7.880127 | 0.115831 | DE | 7.757772 | 0.165433 | DE | 7.999737 | 0.151074 | CD |
| QTL2+/QTL12+ | 8 | 8.068536 | 0.114989 | DE | 7.71644 | 0.164193 | DE | 8.410504 | 0.150008 | BC |
| QTL2+/QTL12+ | 10 | 7.757902 | 0.119877 | E | 7.542371 | 0.174971 | E | 7.976902 | 0.153291 | D |
| QTL2+/QTL12+ | 7 | 8.445322 | 0.116262 | BC | 8.453916 | 0.165441 | BC | 8.454128 | 0.152172 | B |
| QTL2+/QTL12+ | 6 | 8.710128 | 0.112567 | AB | 8.527974 | 0.15839 | B | 8.891398 | 0.148963 | A |
| QTL2+/QTL12+ | 5 | 8.139645 | 0.113357 | CD | 8.085799 | 0.160636 | CD | 8.196954 | 0.148963 | BCD |
| MR1 | 19 | 8.718684 | 0.131826 | AB | 8.499747 | 0.186377 | ABC | 8.914223 | 0.173647 | A |
| WSH-39-1083-AN | 24 | 8.987906 | 0.112567 | A | 8.973418 | 0.15839 | A | 9.002509 | 0.148963 | A |
| Top Mark | 22 | 8.920173 | 0.141613 | A | 8.859122 | 0.204988 | AB | 9.002509 | 0.182441 | A |
| Vedrantais | 23 | 8.94632 | 0.161482 | A | 8.935303 | 0.241386 | AB | 9.011631 | 0.202427 | A |

Example 6: Further Mapping of ZYMV/WMV QTL on Linkage Group 11

As shown in Example 2, the genetic map interval bounded by NU0219106 and NU0219710 on linkage group 11 of the melon genetic map (39.0-53.4 cM) carries alleles for resistance to WMV and ZYMV as in lines ME8094 and Mbnr992. Also, it was found that the marker NU0218779 at 44.6 cM is most tightly linked to the ZYMV and WMV resistance traits. This example provides further genetic mapping and phenotypic information associated with introgresand that the AMA converted BC4 line had a donor introgression at QTL11 spanning the region of 8.37-49.01 cM (40.63 cM). The percent of recurrent parent for the second GAL pedigree was 93.94% and the GAL converted BC3 line had a donor introgression at QTL11 spanning the region of 40.62-94.71 cM (54.09 cM). The donor introgressions were initially selected using two informative markers in the QTL11 interval at 38.89 and 44.63 cM, therefore spanning a 5.66 cM genomic region.

Results of the GAL trial are shown on Table 10 and FIG. 7. Significant differences among lines carrying the donor alleles and lines carrying the recurrent parent allele at QTL11 were identified for both BC3 families for fruit length, cavity length, fruit set and maturity and for one BC3 family for brix and cavity width implying that introgression of the donor allele at QTL11 may result in fruit with larger length, later maturity, lower fruit set and lower brix. For four of these eight comparisons there were no significant differences among the phenotypes of the unconverted lines and the line carrying the recurrent parent allele at QTL11, while for the other comparisons these lines differed significantly. In addition, three comparisons among lines of the second BC3 family showed no significant difference among the converted lines but significant differences versus the unconverted inbred control for brix, fruit width and cavity width, implying that the remnant donor introgressions in the background of the converted lines (~5-6% of genome as discussed above) may be responsible for differences in fruit width and brix.

the two trials (GAL: larger fruit length, later maturity, lower fruit set and lower brix; AMA: higher fruit set, lower fruit length and lower vigor) it was concluded that either these effects are dependent on melon type (although unlikely), or are due to genetic factors not very tightly linked to the ZYMV/WMV locus at QTL11. Genetic fingerprinting data showed that the donor introgressions in studied lines covered genomic regions of 54.09 cM and 40.63 cM in the GAL and AMA pedigrees respectively.

Concurrently with these evaluations, lines were developed which carry short introgressions of ZYMV/WMV QTL11, to identify optimal breeding events not leading to undesirable phenotypes. Isogenic lines were tested that carried fixed introgressions of the donor and recurrent parent alleles at the ZYMV/WMV QTL11 region from BC2-derived pedigrees of the cross WSH-39-1083-AN×ME8094 (FIG. 9). Each family comprises an introgressed region of part of the most likely QTL11 genomic region. The trial was

TABLE 10

Trial of the GAL-188-DUFFE-AN MABC conversion carrying the ZYMV/WMV QTL11 introgression (homozygous donor (DN) and recurrent parent (RP) alleles next to the unconverted inbred lines (FS). Two different BC3 families were evaluated for listed phenotypic traits. Least square means and least square differences are shown.

| Family | Entry | Brix (° Brix) LSD | LSM | Firmness (kgf) LSD | LSM | Fruit Width (mm) LSD | LSM | Fruit Length (mm) LSD | LSM | Cavity Width (mm) LSD | LSM | Cavity Length (mm) LSD | LSM | Fruit set (# fruit/plot) LSD | LSM | Maturity (DAT) LSD | LSM |
|---|---|---|---|---|---|---|---|---|---|---|---|---|---|---|---|---|---|
| 1 | FS | A | 13.3 | AB | 9.4 | BC | 124.0 | C | 124.6 | CD | 43.6 | C | 79.0 | A | 46.4 | C | 64.4 |
| 1 | DN | D | 8.2 | B | 7.4 | BCD | 123.1 | B | 132.5 | A | 51.0 | B | 85.4 | B | 32.6 | A | 68.8 |
| 1 | RP | C | 10.7 | AB | 9.4 | D | 117.2 | C | 121.2 | BC | 45.3 | C | 75.7 | A | 50.6 | B | 66.4 |
| 2 | FS | B | 12.2 | A | 9.8 | CD | 120.8 | C | 122.5 | D | 40.0 | C | 78.4 | A | 47.2 | C | 64.4 |
| 2 | DN | C | 10.0 | AB | 9.5 | A | 132.1 | A | 145.0 | A | 53.3 | A | 91.5 | B | 28.6 | A | 70.0 |
| 2 | RP | C | 10.9 | A | 10.0 | AB | 128.5 | B | 130.7 | AB | 49.0 | BC | 80.7 | A | 42.4 | BC | 66.0 |

Results of the AMA trial are shown on Table 11 and FIG. 8. Significant differences likely due to the background of converted lines were found for days after transplant, cavity length and possibly fruit width, cavity width and brix. For fruit set, fruit length and vigor, significant differences were probably due to the donor introgression at QTL11 although background differences were also clear for fruit set and fruit length. The QTL11 introgression resulted in significantly higher fruit set, lower fruit length and lower vigor. The lines carrying the donor introgression at QTL11 also appeared more susceptible to powdery mildew than lines with the RP introgression or unconverted lines, although the statistical significance of this observation was not tested.

arranged in a split plot design with 10 replications. Five fruit collected from the 10-plant plots were phenotyped for a number of relevant traits which displayed phenotypic variation among experimental entries. For this locus, data were collected for fruit size, fruit set, brix, firmness and maturity. Least square means were estimated using the appropriate mixed model in JMP and least square differences were derived using Student's t method.

Results demonstrate that significant differences were identified only for fruit length and width (Table 12) but in different families the donor allele was shown to confer increase or decrease in fruit size, and also a concomitant increase or decrease in brix. Variation is fruit size is not

TABLE 11

Trial of the AMA-188-DECO-AN MABC conversion carrying the ZYMV/WMV QTL11 introgression (homozygous donor (DN) and recurrent parent (RP) alleles next to the unconverted inbred lines (FS). One BC4 family was evaluated for listed phenotypic traits. Least square means and least square differences are shown.

| Entry | DAT (days) LSD | LSM | Fruit Set (# fruit/plot) LSD | LSM | Vigor (0-1 ratings) LSD | LSM | Firmness (kgf) LSD | LSM | Brix (° Brix) LSD | LSM | Fruit Width (mm) LSD | LSM | Fruit Length (mm) LSD | LSM | Cavity Width (mm) LSD | LSM | Cavity Length (mm) LSD | LSM |
|---|---|---|---|---|---|---|---|---|---|---|---|---|---|---|---|---|---|---|
| FS | A | 72.8 | C | 12.3 | A | 1 | A | 6.1 | A | 12.6 | B | 139.6 | A | 251.5 | B | 67.8 | A | 181.9 |
| DN | B | 71.0 | A | 21.3 | B | 0.1 | A | 6.2 | B | 9.8 | B | 135.9 | C | 220.5 | B | 67.4 | B | 159.8 |
| RP | B | 71.2 | B | 14.6 | A | 0.9 | A | 5.9 | C | 9.2 | A | 152.1 | B | 231.9 | A | 71.4 | B | 161.4 |

In summary, statistically significant differences were identified among tested lines suggesting that the QTL11 and/or flanking regions around this locus may lead to undesirable phenotypes in the GAL and AMA lines. However, since these differences correspond to different traits in unexpected in BC2 lines that likely still carry a significant amount of donor genome (ME8094 has drastically different size from elite melon lines) and heterozygous genomic regions. Overall, differences among the isogenic lines for the five families tested were inconsistent and do not reveal any trend even after taking into consideration that different events were tested for each family.

TABLE 12

Least square means and least square differences for phenotypic data collected from five BC2-derived families with the ZYMV/WMV QTL11 introgression fixed for the homozygous donor (DN) or the homozygous recurrent parent (RP) alleles.

| BC2F4 family | QTL11 | Firmness (kgf) | | Brix (° Brix) | | Fruit Width (mm) | | Fruit Length (mm) | | Fruit set (# fruit/plant) | | DAT (days) | |
|---|---|---|---|---|---|---|---|---|---|---|---|---|---|
| | | LSM | LSD | LSM | LSD | LSM | LSD | LSM | LSD | LSM | LSD | LSM | LSD |
| 1 | RP | 5.3 | BC | 9.3 | D | 121.8 | AB | 116.9 | EF | 4.2 | CD | 61.0 | CD |
| 1 | DN | 4.9 | C | 9.4 | D | 113.1 | C | 114.5 | F | 4.2 | CD | 60.6 | CD |
| 2 | RP | 4.5 | C | 7.1 | F | 121.8 | AB | 139.4 | B | 4.5 | BC | 62.9 | A |
| 2 | DN | 4.5 | C | 7.6 | E | 123.1 | A | 146.2 | A | 4.0 | CD | 62.9 | A |
| 3 | RP | 6.9 | A | 12.0 | A | 124.9 | A | 122.6 | DE | 3.0 | F | 62.6 | AB |
| 3 | DN | 6.8 | A | 11.8 | A | 117.2 | BC | 124.7 | CD | 3.4 | EF | 61.4 | BC |
| 4 | RP | 6.2 | AB | 11.0 | B | 100.8 | E | 112.5 | F | 5.2 | A | 61.1 | CD |
| 4 | DN | 5.2 | BC | 10.5 | C | 95.8 | F | 113.3 | F | 5.5 | A | 60.0 | D |
| 5 | RP | 5.2 | BC | 11.2 | B | 107.5 | D | 112.3 | F | 4.7 | B | 61.9 | ABC |
| 5 | DN | 4.7 | C | 11.2 | B | 113.2 | C | 129.5 | C | 3.8 | DE | 61.5 | BC |

These results lead to the conclusion that no undesirable phenotype is associated with these short events developed in the ZYMV/WMV QTL11 genomic region (FIG. 9). Two of these breeding events spanning 3.12 and 5.95 cM, respectively, at the ZYMV/WMV QTL11 locus (FIG. 10) were tested with the appropriate ZYMV and WMV bioassays to confirm efficacy (resistance to the two viruses). Both events were resistant to ZYMV and WMV, which implies that both events can be deployed for marker-assisted selection and backcrossing of this locus, and that the most likely region of this QTL can be narrowed down to the interval of 44.6 to 48.0 cM (between markers NU0218779 and NCMEL008383078).

Example 7: Further Mapping of CMV QTL on Linkage Group 12

As discussed for instance at Example 3, the genetic map interval between NU0243358 and NU0220836 on linkage group 12 of the melon genome (39.8-46.8 cM) controls resistance to CMV. However, lines carrying the ME8094 introgression at this genomic region were found to have irregular shape and enlarged blossom end scars (FIG. 11). Therefore, an effort was initiated to fine-map this genomic region and develop lines carrying shorter introgressions in this region.

To fine-map CMV QTL12, a study was initiated with 28 entries of which 20 were lines with recombination events in the QTL12 region (BC2-derived lines from the cross of WSH-39-1083-AN with the trait donor ME8094) and 8 were resistant and susceptible controls. The experiment was arranged in an RCBD design and had 10 replications. Replications 1-5 were sown on Jul. 5, 2011 and replications 6-10 were sown on Jul. 11, 2011; seedlings were inoculated on 7/13, 7/19 or 7/20 depending on the seed germination. Seedlings were scored for disease 6, 9 and 14 days after inoculation (dpi) and the area under the disease progress curve (AUDPC) was calculated. Replications 1-5 and replications 6-10 were treated as timepoints 1 and 2, respectively, and a mixed model was used to understand whether least square means can be derived across the 10 reps for each entry. Statistical analysis showed that the entry by timepoint interaction was highly significant; therefore, least square means were derived separately for each of the two timepoints (FIG. 12). One entry was removed due to very low germination that resulted in a large number of missing data points. Least square means of entries ranked relatively similar in comparison to controls with the exception of entry 20; therefore, results were consistent between timepoints 1 and 2.

It should be noted that the lines which scored as susceptible (e.g. rows 1-3, 9, 11-16, 21, and Vedrantais in FIG. 12A) had very consistent phenotypes with disease scores of 7 to 9 at 6, 9 and 14 dpi and, therefore, AUDPC of 79-88 for the majority of seedlings across replications. However, all the lines scored as intermediate resistant (e.g. rows 5-8, 10, 17-19 in FIG. 12A) had variable disease scoring resulting in AUDPC of 0-88 and, therefore, higher standard errors. This was primarily due to lower disease scores (resistant or intermediate resistant) during the 6 and 9 dpi and progressively higher scores (susceptible) during the 14 dpi scoring, that have been observed previously and imply the need for evaluation of the CMV material past the seedling stage. Due to the highly variable AUDPC scores that were used for calculation of least square means, least square means for the 14 dpi disease scoring were also derived, which were in agreement (FIG. 12).

Comparison of the 19 lines carrying recombination events for QTL12 leads to the conclusion that the likely region of the genetic factor conferring resistance to CMV on linkage group 12 is located between NU0243358 and NU0218323, spanning the genetic interval of 39.77 to 44.47 cM on the melon genetic map as schematically shown in FIG. 12B.

Next, melon lines comprising shorter introgressions from the resistant parent line in the fine-mapped genomic region of CMV QTL12 were developed for further breeding use, and these lines were evaluated for undesirable phenotypes. BC3-derived families of the cross WSH-39-1083-AN× ME8094 were studied after developing isogenic lines that carried fixed introgressions of the donor and recurrent parent alleles at the CMV QTL12 region (FIG. 13). Each family had undergone a unique recombination event that covered part of the most likely QTL12 genomic region (shown on FIG. 13). The trial was arranged in a split plot design with 10 replications. Five fruit collected from the 10-plant plots were phenotyped for blossom end scar size, fruit length and width since they were previously identified as putative drag due to the CMV QTL12 introgression, but additional traits were visually evaluated and brix data were collected from selected families Least square means were estimated using the appropriate mixed model in JMP and least square differences were derived using Student's t method. Significant differences were not found among isogenic lines for any trait, with only one exception (fruit length of family 6), as shown on Table 13.

TABLE 13

Least square means and least square differences for phenotypic data collected from BC3-derived families with the CMV QTL12 introgression fixed for the homozygous donor (DN) or recurrent parent (RP) alleles. The recurrent parent was also included in two entries of the trial. Phenotypes of blossom end scar size (BES), fruit length and fruit width are all presented in mm.

| BC3 family | QTL12 | BES LSD | BES LSM | Width LSD | Width LSM | Length LSD | Length LSM |
|---|---|---|---|---|---|---|---|
| 1 | DN | DEF | 37.13 | G | 114.07 | G | 115.28 |
| 1 | RP | CD | 38.96 | FG | 114.82 | G | 116.13 |
| 2 | DN | CDE | 38.52 | EFG | 116.03 | FG | 118.37 |
| 2 | RP | DEF | 36.67 | EF | 117.88 | F | 120.66 |
| 3 | DN | FG | 34.01 | E | 118.30 | E | 127.16 |
| 3 | RP | EF | 35.32 | DE | 118.97 | E | 127.60 |
| 4 | DN | GH | 31.56 | DE | 118.55 | A | 142.88 |
| 4 | RP | H | 29.58 | EFG | 116.30 | AB | 140.96 |
| 5 | DN | A | 46.46 | A | 131.37 | CD | 136.53 |
| 5 | RP | A | 45.90 | A | 132.15 | BC | 138.52 |
| 6 | DN | BC | 40.78 | B | 126.40 | ABC | 139.20 |
| 6 | RP | BC | 41.04 | BC | 124.00 | D | 132.71 |
| WSH-39-1083-AN | BC | | 40.80 | BC | 123.73 | E | 125.39 |
| WSH-39-1083-AN | AB | | 43.35 | CD | 121.62 | E | 125.10 |

It is concluded that no undesirable phenotype is associated with these "short" introgressions in the CMV QTL12 genomic region (FIG. 13). Therefore, three selected lines comprising an introgressed region spanning a 3.3-9.1 cM interval (FIG. 14) were tested with the appropriate bioassay to confirm efficacy (resistance to CMV). The events were found to be intermediate resistant, resistant and highly resistant (FIG. 14). This is likely due to the CMV QTL12 having a moderate effect and additional minor QTL conferred by ME8094 are likely present in these BC2-derived lines. Lines comprising the introgressed region, for instance as represented by these three, are efficacious and lack undesirable phenotypes.

The invention claimed is:

1. A melon plant comprising an introgressed chromosomal region conferring resistance to Zucchini Yellow Mosaic Virus (ZYMV) and Watermelon Mosaic Virus (WMV), wherein the region is defined by flanking markers NU219106 and NU219710 on melon chromosome 11, wherein the plant further comprises at least one trait selected from the group consisting of: produces fruit with a width to length ratio of at least 0.5; produces fruit with orange flesh color, green flesh color, or white flesh color; demonstrates fruit Brix≥9.5° Bx; displays resistance to CMV; displays resistance to MNSV; displays resistance to PRSV; and displays resistance to Powdery Mildew, and wherein said introgressed chromosomal region comprises marker NU0218916, marker NU0219099, marker NU0218656, marker NCMEL008383076, marker NCMEL008383077, marker NU0218779, marker NCMEL008383075, marker NCMEL008383078, marker NU0220333, marker NU0219293, marker NU0218835, or marker NU0244142.

2. The melon plant of claim 1, wherein the at least one trait is a width to length ratio of at least 0.5.

3. The melon plant of claim 1, wherein the at least one trait is selected from the group consisting of orange flesh color, green flesh color, and white flesh color.

4. The melon plant of claim 1, wherein the at least one trait is Brix≥9.5° Bx.

5. The melon plant of claim 1, wherein the at least one trait is resistance to CMV.

6. The melon plant of claim 1, wherein the at least one trait is resistance to Powdery Mildew.

7. The melon plant of claim 1, wherein the at least one trait is resistance to MNSV.

8. The melon plant of claim 1, wherein the at least one trait is resistance to PRSV.

9. A part of the melon plant of claim 1, wherein the plant part is selected from the group consisting of: a seed, a root, a leaf, a stem, pollen, an ovule, an anther, a pistil, and a cell.

10. A tissue culture of regenerable cells of the plant of claim 1.

11. The tissue culture of claim 10, comprising cells or protoplasts from a plant part selected from the group consisting of embryo, meristem, cotyledon, pollen, leaf, anther, root, root tip, pistil, flower, and seed.

12. The plant of claim 1, which is inbred.

13. The plant of claim 1, which is hybrid.

14. The melon plant of claim 1, wherein the locus is derived from line ME8094, a representative sample of seed of said line having been deposited under NCIMB accession number 41653.

15. The melon plant of claim 1, further defined as comprising a locus contributing to CMV resistance on melon linkage group 12.

16. The melon plant of claim 15, wherein the locus comprises a genetic marker selected from the group consisting of NU0243358, NU0218323, NU0219184, NU0219714, NU0220980, NU0243527, NU0220836, NU0218164, NU0218516, NU0218074, NU0218603, and NU0220144.

17. The melon plant of claim 1, further defined as comprising a locus contributing to CMV resistance on melon linkage group 2.

18. The melon plant of claim 17, wherein the locus comprises a genetic marker selected from the group consisting of NU0220476, NU0219006 NU0218624, NU0219047, NU0220488, and NU0220264.

* * * * *

UNITED STATES PATENT AND TRADEMARK OFFICE
CERTIFICATE OF CORRECTION

| | |
|---|---|
| PATENT NO. | : 11,019,777 B2 |
| APPLICATION NO. | : 15/814233 |
| DATED | : June 1, 2021 |
| INVENTOR(S) | : Bachlava et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 626 days.

Signed and Sealed this
Seventh Day of February, 2023

Katherine Kelly Vidal
*Director of the United States Patent and Trademark Office*

SEQUENCE LISTING

<160> NUMBER OF SEQ ID NOS: 39

<210> SEQ ID NO 1
<211> LENGTH: 121
<212> TYPE: DNA
<213> ORGANISM: Cucumis melo

<400> SEQUENCE: 1
ttaatttaaa atatgatcag aacatcaatt gacaaattct gaatactata cttgcacatt    60
wccttccata caagaaaata tgtggaactt cactcatggt agattcacat atataact    120 a    121

<210> SEQ ID NO 2
<211> LENGTH: 121
<212> TYPE: DNA
<213> ORGANISM: Cucumis melo

<400> SEQUENCE: 2
cctgccatgg cacctactcg ctgaaagcaa tgctccccac aacaatgcct tgtcatcagg    60
mgctacatcc atcgatttcg ctatgtcaaa ggctttatct agctccccag atcgagctag    120
c    121

<210> SEQ ID NO 3
<211> LENGTH: 121
<212> TYPE: DNA
<213> ORGANISM: Cucumis melo

<400> SEQUENCE: 3
gtggctgcag gatttattt caggtacaaa acaatgtctc ttgtctcata tacgaactta    60
ygtccagcct ccaaattcgg cacaagccag attggcttat cagttagcac catttaaaga    120
c    121

<210> SEQ ID NO 4
<211> LENGTH: 121
<212> TYPE: DNA
<213> ORGANISM: Cucumis melo
<220> FEATURE:
<221> NAME/KEY: misc_feature
<222> LOCATION: (27)..(27)
<223> OTHER INFORMATION: n is a, c, g, or t

<400> SEQUENCE: 4
atggcttttg cagtggacct ctttacnaaa ttcttcaccc gataaaccag agatagtgtt    60
raaggtgaag tcttaaattg tctgggcttg tacaagaagt tcactgacaa gctcttagtt   120
c                                                                  121

<210> SEQ ID NO 5
<211> LENGTH: 121
<212> TYPE: DNA
<213> ORGANISM: Cucumis melo
<220> FEATURE:
<221> NAME/KEY: misc_feature
<222> LOCATION: (19)..(19)
<223> OTHER INFORMATION: n is a, c, g, or t

<400> SEQUENCE: 5
ccagcacaac attgaatgna aacccgatg cctttacatg tcttttaatg tcaattttca     60
kacttccaat gtccaaacag aaaggaaaa accaaagag gtcaaaagta ggtttattca    120
a                                                                  121

<210> SEQ ID NO 6
<211> LENGTH: 121
<212> TYPE: DNA
<213> ORGANISM: Cucumis melo

<400> SEQUENCE: 6
aattcgtaga gagcgtcctg aactcctaga gagcgtaaga gggtgagcta ctaactcatt    60
rtaggttgtt ggttgagatc catgttaatt gggagaacat gggcatttgc catcagacta   120
g                                                                  121

<210> SEQ ID NO 7
<211> LENGTH: 121
<212> TYPE: DNA
<213> ORGANISM: Cucumis melo

<400> SEQUENCE: 7
cttgtgaagc tcatacgaga gaacaagatg atgagtcata caaagccgat gtggcttcat    60
kggatgattt ggaccaaagt aaacacttcc cacgtcccct gcaaaaccat attttatgca   120
a                                                                  121

<210> SEQ ID NO 8
<211> LENGTH: 121
<212> TYPE: DNA
<213> ORGANISM: Cucumis melo

<400> SEQUENCE: 8
tcctagccct ttatcaaggt tatgtctcct atttacctttt agaccgaccc atgacggtta   60
yctagatatg tctagtagca ttgcactctc ggaagtccaa acgtcaacat tgacctgcct   120
g                                                                  121

```
<210> SEQ ID NO 9
<211> LENGTH: 102
<212> TYPE: DNA
<213> ORGANISM: Cucumis melo

<400> SEQUENCE: 9
attgaataaa gcgcaccacc aaggaaaagt atcagttaga gmataaaacc aggaactaaa        60
atcctggatt taaatgtcaa tgatatgatt tcttatagca aa                         102

<210> SEQ ID NO 10
<211> LENGTH: 121
<212> TYPE: DNA
<213> ORGANISM: Cucumis melo

<400> SEQUENCE: 10
ttttagtgtc aaaacccaaa gagataccga aaagtttatg tgattgcaaa cagcaccacc        60
rttctctttc caacagttgg aaaatcctcc tattcctctc cctcaagttt cctaaaaaat       120
t                                                                      121

<210> SEQ ID NO 11
<211> LENGTH: 121
<212> TYPE: DNA
<213> ORGANISM: Cucumis melo

<400> SEQUENCE: 11
ggaacgttga aggtgcattg gtcagcccaa atggcataaa caaaaactca tagtgccctt        60
maggtgtcca aaaggctgtc ttctctacat catctgcaca catacgtatt tgatggtaac       120
c                                                                      121

<210> SEQ ID NO 12
<211> LENGTH: 121
<212> TYPE: DNA
<213> ORGANISM: Cucumis melo

<400> SEQUENCE: 12
gaaataccaa tgcaaggatt tgaacacaga acctcctaaa ccacactact ctattaccat        60
ytaaaatcgc tgattggccc aaaagcttaa actgataggt gaaagcttat ttaaaataat       120
a                                                                      121

<210> SEQ ID NO 13
<211> LENGTH: 121
<212> TYPE: DNA
<213> ORGANISM: Cucumis melo

<400> SEQUENCE: 13
tgtattagtt aaagaaattg ttgaatgata tacttacgct aagaccactc taatgacgat        60
raccaccacg ttttcatggt agcaagattt tatcccatat tgtagctgca agtaaaaagt       120
a                                                                      121

<210> SEQ ID NO 14
<211> LENGTH: 121
<212> TYPE: DNA
<213> ORGANISM: Cucumis melo

<400> SEQUENCE: 14
tgacttctgt ccacagagct cgccacttct aatttacata tctacaaatt tccaatgcca        60
sattgatatt ggtgtgacct ttctcattca ctgatcatca atctccatttt ttcttgcact     120
```

<210> SEQ ID NO 15
<211> LENGTH: 121
<212> TYPE: DNA
<213> ORGANISM: Cucumis melo

<400> SEQUENCE: 15
atactttcga cgtagcttta tcgttgtcag ttcatcactc gcctgtgacg atttgaataa      60
kcacaggctt agcttaacct ctccattaat tggggttcac ttggctgtga ccaaaactaa     120
g                                                                    121

<210> SEQ ID NO 16
<211> LENGTH: 121
<212> TYPE: DNA
<213> ORGANISM: Cucumis melo

<400> SEQUENCE: 16
accatcgatt tgcgtatcat ttactaggtg agttgttttc aatgtattgg aataccattt      60
yatctgcact atatagattg ataatgaaaa ttctttgttt cctctcgtct accacgttca     120
t                                                                    121

<210> SEQ ID NO 17
<211> LENGTH: 121
<212> TYPE: DNA
<213> ORGANISM: Cucumis melo

<400> SEQUENCE: 17
catagaagtc aagtgatata aagagagaaa cgtaaagcat agaggtttat ccttacagtc      60
rcttgttctc taaacatac atttcctcca catcacctac aaaacattta accatatgag     120
a                                                                    121

<210> SEQ ID NO 18
<211> LENGTH: 121
<212> TYPE: DNA
<213> ORGANISM: Cucumis melo

<400> SEQUENCE: 18
ctacataaag ccctatcgat agaggtctcc aggtacaata gtttctagct agagttaagg      60
raaagacaaa cattgtgtaa ttggatagtt aatgtggatt aatcccaggt ttcatgttct     120
a                                                                    121

<210> SEQ ID NO 19
<211> LENGTH: 121
<212> TYPE: DNA
<213> ORGANISM: Cucumis melo

<400> SEQUENCE: 19
caccaccttt gacatcacca aaggccgctt ctccctctcc ctacaaatac tattggcgac      60
rgcttctcct tttggttgac aaaggtttat ggcccttgcc gatacaagga taggcctaca     120
t                                                                    121

<210> SEQ ID NO 20
<211> LENGTH: 121
<212> TYPE: DNA
<213> ORGANISM: Cucumis melo
<220> FEATURE:
<221> NAME/KEY: misc_feature
<222> LOCATION: (23)..(23)
<223> OTHER INFORMATION: n is a, c, g, or t

<400> SEQUENCE: 20
acacagagtc ggcgcatctc ttngaaaccc tatatgaccg tgagaagatg atggtgcttt    60
rattctctta cgcagtacac atttcccaag gcgagttaaa cttcaaaatt taaaaactat   120
g                                                                   121

<210> SEQ ID NO 21
<211> LENGTH: 121
<212> TYPE: DNA
<213> ORGANISM: Cucumis melo
<220> FEATURE:
<221> NAME/KEY: misc_feature
<222> LOCATION: (108)..(108)
<223> OTHER INFORMATION: n is a, c, g, or t

<400> SEQUENCE: 21
tctttcccag attaatggct aggaatttac tcggatggtt atttctagaa gttttagttc    60
rattcttccg cagattccct cccttt caac ggttgtaaca actcccanaa ttactccaaa   120
t                                                                   121

<210> SEQ ID NO 22
<211> LENGTH: 94
<212> TYPE: DNA
<213> ORGANISM: Cucumis melo

<400> SEQUENCE: 22
gtcctgagaa gcacaaatac aaatacaaga aagraggata acctgataca aacatggtag    60
catgtcatat ttaaaaatct agttatgctt caaa                                94

<210> SEQ ID NO 23
<211> LENGTH: 121
<212> TYPE: DNA
<213> ORGANISM: Cucumis melo
<220> FEATURE:
<221> NAME/KEY: misc_feature
<222> LOCATION: (114)..(115)
<223> OTHER INFORMATION: n is a, c, g, or t

<400> SEQUENCE: 23
gagatagaga aagaagtaga taaagtgatt tcccggatta gagaagtagg gtcaaaagta    60
mgaagcaaat tcgactccga tggtacagtt gttcaatctg agaacttgtt gcanncggtg   120
c                                                                   121

<210> SEQ ID NO 24
<211> LENGTH: 121
<212> TYPE: DNA
<213> ORGANISM: Cucumis melo

<400> SEQUENCE: 24
aacagaaaag atcaagaatg aaatgaaaag gacctttaaa agggaagcga aggctctatt    60
wctcttggat gtaacttaag aaacctcata aacattcaaa gtttcaagct caaccataaa   120
a                                                                   121

<210> SEQ ID NO 25
<211> LENGTH: 121
<212> TYPE: DNA
<213> ORGANISM: Cucumis melo
<220> FEATURE:

```
<221> NAME/KEY: misc_feature
<222> LOCATION: (90)..(90)
<223> OTHER INFORMATION: n is a, c, g, or t

<400> SEQUENCE: 25
cttatgcttg aattagtaat ttttgtgttt tcagttctgt gtagatccat tttttatgcc    60
yttcacgtga aagccattat tagtgggttn aaaatgatgt atcattttgc tgcttcttaa   120
c                                                                   121

<210> SEQ ID NO 26
<211> LENGTH: 121
<212> TYPE: DNA
<213> ORGANISM: Cucumis melo

<400> SEQUENCE: 26
cataccgaaa gaaggcagtc cagtcggcca tggtcgtttc agtctaagcg gaaacggtga    60
yggatacatt ggaaatgttg tcagtggttc aatttcccac aaagacactc ttggctgtcg   120
t                                                                   121

<210> SEQ ID NO 27
<211> LENGTH: 20
<212> TYPE: DNA
<213> ORGANISM: Cucumis melo

<400> SEQUENCE: 27
gtaccgccta gggtttctcc                                                20

<210> SEQ ID NO 28
<211> LENGTH: 20
<212> TYPE: DNA
<213> ORGANISM: Cucumis melo

<400> SEQUENCE: 28
cgaggaagag agagaagggg                                                20

<210> SEQ ID NO 29
<211> LENGTH: 115
<212> TYPE: DNA
<213> ORGANISM: Cucumis melo
<220> FEATURE:
<221> NAME/KEY: misc_feature
<222> LOCATION: (101)..(103)
<223> OTHER INFORMATION: n is a, c, g, or t
<220> FEATURE:
<221> NAME/KEY: misc_feature
<222> LOCATION: (105)..(111)
<223> OTHER INFORMATION: n is a, c, g, or t
<220> FEATURE:
<221> NAME/KEY: misc_feature
<222> LOCATION: (113)..(115)
<223> OTHER INFORMATION: n is a, c, g, or t

<400> SEQUENCE: 29
tgtccaagga ttttgtgttt tccagatcag gaaaccagtg tacttcttcc acattcggct    60
rttccagcct tcgattagag ctcgatattg gatgtaatta nnnannnnnn ncnnn        115

<210> SEQ ID NO 30
<211> LENGTH: 121
<212> TYPE: DNA
<213> ORGANISM: Cucumis melo

<400> SEQUENCE: 30
gaatgcttcc tttcacatat tttctgtgat attcttttcc ctgaacaatg ctgaaccgaa    60
```

```
yatggtatca tatggatgga tttatttatc atataatttt caaaacttaa ttatatagca    120
t                                                                   121

<210> SEQ ID NO 31
<211> LENGTH: 121
<212> TYPE: DNA
<213> ORGANISM: Cucumis melo

<400> SEQUENCE: 31
tcattgagtt caatcgtatg aagtacttct gtgcatgact ggccacttga gtcggtgttc    60
kggatataac gaagtttctt gaaatgcttc tccaatcccc tttcccaaac ttatctagac    120
c                                                                   121

<210> SEQ ID NO 32
<211> LENGTH: 121
<212> TYPE: DNA
<213> ORGANISM: Cucumis melo

<400> SEQUENCE: 32
gatcttttga attactattc ctcaacatat ccttataatt ttcatatatc atcaccaaac    60
rttcatcatt tttccctcca ttctatcaac caatccttca aacaatcaca actccaaaga    120
g                                                                   121

<210> SEQ ID NO 33
<211> LENGTH: 121
<212> TYPE: DNA
<213> ORGANISM: Cucumis melo
<220> FEATURE:
<221> NAME/KEY: misc_feature
<222> LOCATION: (118)..(118)
<223> OTHER INFORMATION: n is a, c, g, or t

<400> SEQUENCE: 33
cgtacagacg gattgcgcaa tgaagctatc ccatttaac ttcaacaatg aaacgcatct     60
yctcagcggc atttcatcga acaatatggc gagcgtgcat tgctatgcac ggagaaancc    120
c                                                                   121

<210> SEQ ID NO 34
<211> LENGTH: 121
<212> TYPE: DNA
<213> ORGANISM: Cucumis melo
<220> FEATURE:
<221> NAME/KEY: misc_feature
<222> LOCATION: (96)..(96)
<223> OTHER INFORMATION: n is a, c, g, or t

<400> SEQUENCE: 34
cagtgatatg ataaaataca agaattatga aggctgaagt tcgaatgaat ctacaataat    60
wgggttttgt tacataaatc tgaagtaaaa acttantgag gcatacattt ttgcatggaa    120
t                                                                   121

<210> SEQ ID NO 35
<211> LENGTH: 121
<212> TYPE: DNA
<213> ORGANISM: Cucumis melo

<400> SEQUENCE: 35
atcaggggtc tgaagctgat aatgatgctg taagaaataa gatagaagaa cctcacagaa    60
```

```
ygcttggtac tatatctgga gagcatacta cagtttctga tcagcacgcg gttactaatg      120
a                                                                      121

<210> SEQ ID NO 36
<211> LENGTH: 121
<212> TYPE: DNA
<213> ORGANISM: Cucumis melo
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t

<400> SEQUENCE: 36
gagcccatga caagattccc tcgccaaaag atatgttaat aacaagtaa anttaantac      60 mgaaatcatt ttctaaagtt gaaaaactaa aatcgatgct ttaaaaatac caaaatcaaa    120
a                                                                    121

<210> SEQ ID NO 37
<211> LENGTH: 121
<212> TYPE: DNA
<213> ORGANISM: Cucumis melo
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 37
ttngtatgga tacaacccat aanntctcaa atggaagaag caacaaaaaa acaagaaaaa      60
stggagtaca aacttatccg caaggtgttc gatgaaagtc ctcaaagaag tattattata    120
a                                                                    121

<210> SEQ ID NO 38
<211> LENGTH: 121
<212> TYPE: DNA
<213> ORGANISM: Cucumis melo

<400> SEQUENCE: 38
ttgaaatctt atggtttgag aattgccatg tcactatcct tttagtttgt gtaattttca      60
wgttgctact tatttggctc tggtcataga gatctgtaat ggtttatttt taagggggta    120
a                                                                    121

<210> SEQ ID NO 39
<211> LENGTH: 121
<212> TYPE: DNA
<213> ORGANISM: Cucumis melo
<220> FEATURE:
<221> NAME/KEY: misc_feature
<222> LOCATION: (117)..(117)
<223> OTHER INFORMATION: n is a, c, g, or t
```

```
<400> SEQUENCE: 39
tgaaggccat tgataattca ctaaaggtac tataagagcc gtgcctgcta acctgcattc      60
mgttattttt ggtcaaagaa agcaataaac aacaaagcaa ataaatcaaa tgggaanaaa     120
c                                                                    121
```